(12) United States Patent
Ramesh et al.

(10) Patent No.: US 12,235,984 B1
(45) Date of Patent: Feb. 25, 2025

(54) PATIENT-EMPOWERED DATA MANAGEMENT: A SECURE BLOCKCHAIN ARCHITECTURE WITH DECENTRALIZED OWNERSHIP

(71) Applicant: MediMint, LLC, Marietta, GA (US)

(72) Inventors: Abhisri Ramesh, Washington, DC (US); Kalyani Lakshminarayanan, Marietta, GA (US)

(73) Assignee: MediMint, LLC, Washington, DC (US)

( * ) Notice: Subject to any disclaimer, the term of this patent is extended or adjusted under 35 U.S.C. 154(b) by 0 days.

(21) Appl. No.: 18/679,180

(22) Filed: May 30, 2024

Related U.S. Application Data

(60) Provisional application No. 63/469,730, filed on May 30, 2023.

(51) Int. Cl.
*G06F 21/62* (2013.01)
*G16H 10/60* (2018.01)
*H04L 9/32* (2006.01)

(52) U.S. Cl.
CPC ......... *G06F 21/6218* (2013.01); *G16H 10/60* (2018.01); *H04L 9/3213* (2013.01);
(Continued)

(58) Field of Classification Search
CPC ... H04L 9/3218; H04L 9/3213; H04L 9/3247; H04L 9/3271; H04L 9/3242; G06F 21/6218; G16H 10/60
See application file for complete search history.

(56) References Cited

U.S. PATENT DOCUMENTS 9,355,273 B2 * 5/2016 Stevens ............... G06F 21/6254
10,885,170 B1 * 1/2021 Maliani ................ H04L 9/0643
(Continued)

OTHER PUBLICATIONS

Ali et al., "A Novel Secure Blockchain Framework for Accessing Electronic Health Records Using Multiple Certificate Authority", Applied Sciences, 2021, 26 pages.
(Continued)

*Primary Examiner* — Gary S Gracia
(74) *Attorney, Agent, or Firm* — Blank Rome LLP

(57) ABSTRACT

A blockchain-based system and method for secure and auditable sharing of medical image studies between providers, patients, and authorized recipients. The system has modules for verifying identities of trusted healthcare providers as issuers of medical data, managing secure storage of medical images and metadata, minting non-fungible tokens (NFTs) representing patient ownership of studies, authenticating patient consent for data sharing, and controlling access to shared data by authorized parties. Trusted issuer registration authenticates healthcare providers permitted to submit studies by verifying credentials against authoritative sources. Secure data management employs hierarchical deterministic cryptographic wallets and smart contracts to ensure only verified issuers can create new medical data NFTs on the blockchain. Automated processing extracts image files and metadata upon upload for separate secure storage, with metadata references encrypted in the associated NFT. The system generates patient-controlled wallets for managing ownership of their medical NFTs without separate identity verification. Patient consent for sharing data is authenticated through multi-signature wallets requiring patient approval before minting study NFTs. Controlled access for other parties is gated by cryptographic proofs of authorization without exposing data. The immutable blockchain ledger records all sharing transactions initiated
(Continued)

through patient and provider wallets, providing transparency and an auditable trail of how and when medical data is shared or accessed and by whom. The decentralized architecture promotes patient control, security, and accountability in managing sensitive healthcare information.

28 Claims, 36 Drawing Sheets

(52) U.S. Cl.
CPC .......... *H04L 9/3218* (2013.01); *H04L 9/3247* (2013.01); *H04L 9/3271* (2013.01)

(56) References Cited

U.S. PATENT DOCUMENTS

| | | | |
|---|---|---|---|
| 11,443,838 B1* | 9/2022 | Cordonnier | G16H 50/20 |
| 11,657,176 B2 | 5/2023 | Bulleit et al. | |
| 11,806,241 B1* | 11/2023 | Hussain | A61F 2/30942 |
| 11,862,304 B1* | 1/2024 | Klein | G16H 40/67 |
| 12,033,120 B1* | 7/2024 | Stroke | G06Q 20/0658 |
| 2015/0242641 A1* | 8/2015 | Li | G16Z 99/00 |
| | | | 713/193 |
| 2018/0097638 A1* | 4/2018 | Haldenby | H04W 12/0433 |
| 2018/0130050 A1* | 5/2018 | Taylor | G06Q 20/065 |
| 2018/0130548 A1* | 5/2018 | Fisher | G06Q 20/3227 |
| 2019/0057763 A1* | 2/2019 | Stockert | G06F 21/31 |
| 2019/0147137 A1* | 5/2019 | Gergely | H04L 9/3226 |
| | | | 705/51 |
| 2019/0198144 A1* | 6/2019 | Blackley | G16H 50/20 |
| 2020/0226285 A1* | 7/2020 | Bulleit | G06F 21/33 |
| 2020/0273578 A1* | 8/2020 | Kutzko | H04L 9/0637 |
| 2021/0005292 A1* | 1/2021 | McFarlane | G06F 16/27 |
| 2021/0005296 A1* | 1/2021 | McFarlane | G16H 10/60 |
| 2021/0005299 A1* | 1/2021 | McFarlane | G16H 20/00 |
| 2021/0012326 A1* | 1/2021 | Maxwell Zelocchi | |
| | | | G06Q 20/3827 |
| 2021/0035246 A1* | 2/2021 | Schouppe | H04L 9/50 |
| 2021/0057060 A1* | 2/2021 | Hussam | G06F 21/6254 |
| 2021/0098096 A1* | 4/2021 | Gergely | H04L 63/083 |
| 2021/0174972 A1* | 6/2021 | Pavlatos | G16H 10/60 |
| 2022/0188940 A1* | 6/2022 | McFarlane | G16H 15/00 |
| 2022/0239481 A1* | 7/2022 | Komiyama | H04L 9/30 |
| 2022/0344012 A1* | 10/2022 | Austr?ng | H04L 9/50 |
| 2022/0354440 A1* | 11/2022 | Grajales | G16H 50/30 |
| 2022/0392628 A1* | 12/2022 | Grajales | H04M 1/72412 |
| 2023/0108369 A1* | 4/2023 | Bachoura | G06Q 20/102 |
| | | | 705/50 |
| 2023/0153874 A1* | 5/2023 | Randazzo | G16H 50/70 |
| | | | 705/3 |
| 2023/0177209 A1* | 6/2023 | Goel | H04L 9/3066 |
| | | | 713/171 |
| 2023/0196471 A1* | 6/2023 | Mendell | G06Q 40/08 |
| | | | 705/4 |
| 2023/0270389 A1* | 8/2023 | Randall | G16H 80/00 |
| | | | 600/586 |
| 2023/0277246 A1* | 9/2023 | Casey | G16H 40/20 |
| 2023/0317224 A1* | 10/2023 | Prajapati | G06Q 20/363 |
| | | | 705/51 |
| 2023/0410965 A1* | 12/2023 | Goldberg | G06F 21/6245 |
| 2024/0013199 A1* | 1/2024 | Marshall | G06Q 20/367 |
| 2024/0013202 A1* | 1/2024 | Bacon | G06F 21/64 |
| 2024/0015030 A1* | 1/2024 | Cameron | H04L 9/50 |
| 2024/0020683 A1* | 1/2024 | Bacon | G06Q 20/3674 |
| 2024/0046318 A1* | 2/2024 | Muriqi | G06Q 20/389 |
| 2024/0070627 A1* | 2/2024 | Galterio | G06Q 20/36 |
| 2024/0078537 A1* | 3/2024 | Sandford | G06Q 20/38215 |
| 2024/0095720 A1* | 3/2024 | Binder | H04L 67/02 |
| 2024/0225531 A1* | 7/2024 | Casey | G06T 7/0012 |
| 2024/0235840 A1* | 7/2024 | Osborn | H04L 9/50 |
| 2024/0249277 A1* | 7/2024 | Hwang | G06Q 20/3678 |
| 2024/0256691 A1* | 8/2024 | Hwang | G06F 16/2255 |

OTHER PUBLICATIONS

Solix Technologies, "How a Private Blockchain for Healthcare Could Revolutionize the Industry", retrieved from https://www.solix.com/blog/blockchain-for-healthcare/, retrieved on Sep. 10, 2024, 6 pages.

Kavitha et al., "Transaction of Healthcare Records using Blockchain", International Research Journal of Engineering and Technology (IRJET), vol. 6, No. 4, Apr. 2019, pp. 32-35.

* cited by examiner

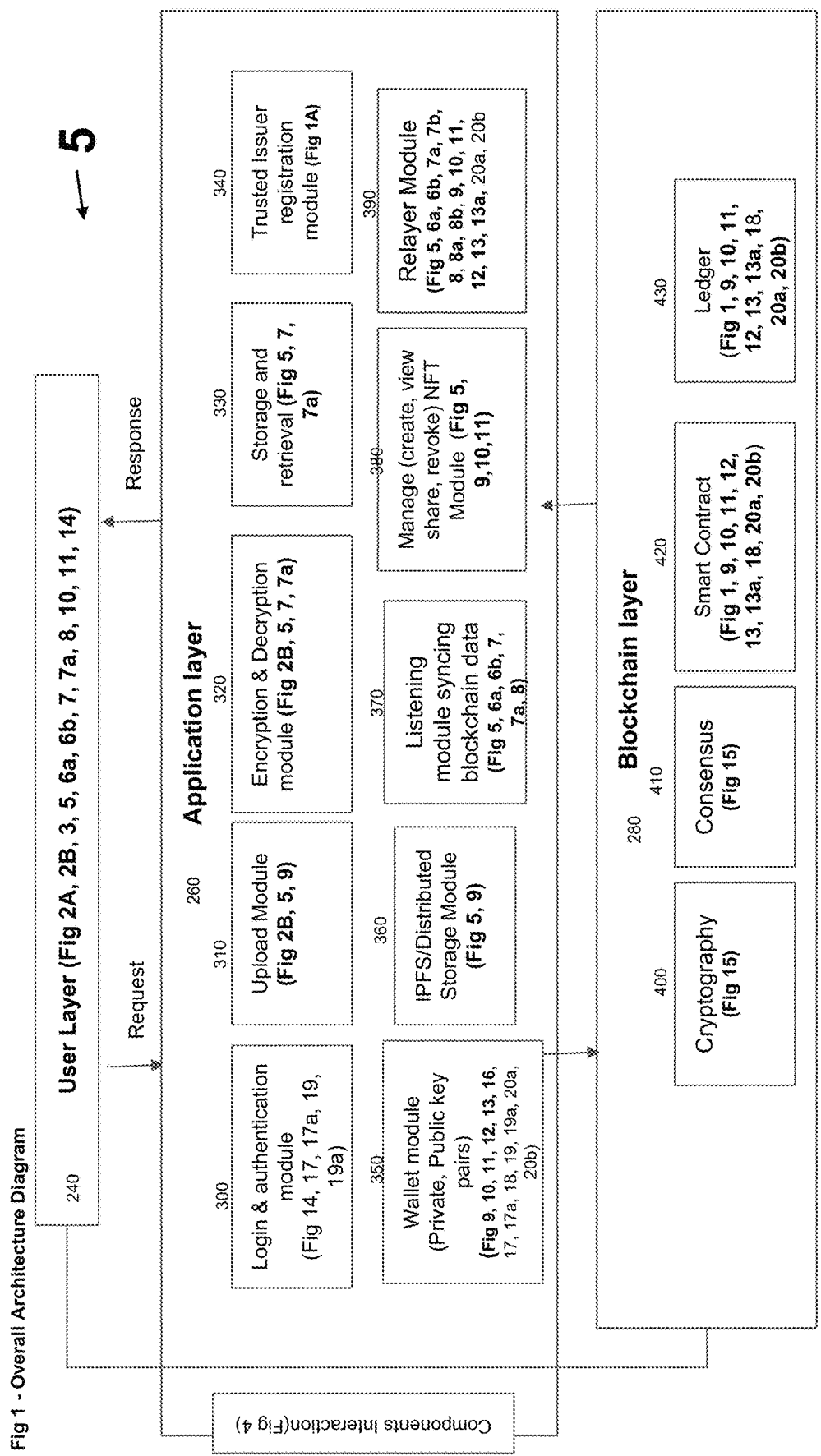
Fig 1 - Overall Architecture Diagram

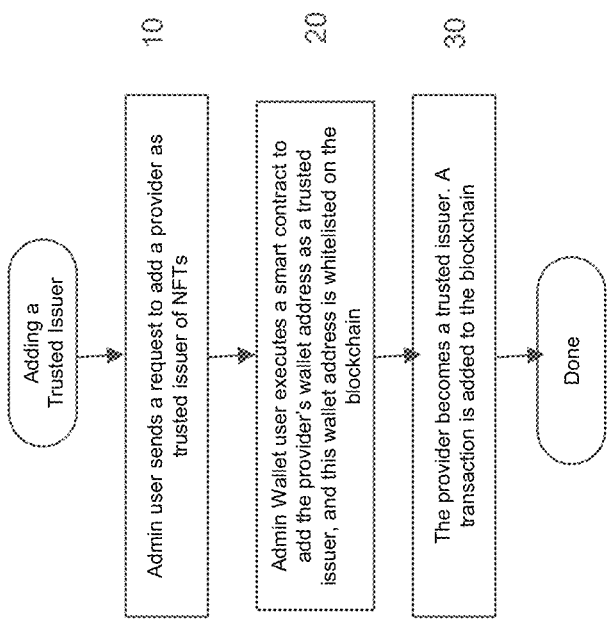
Fig 1A - Adding a Provider as a Trusted Issuer

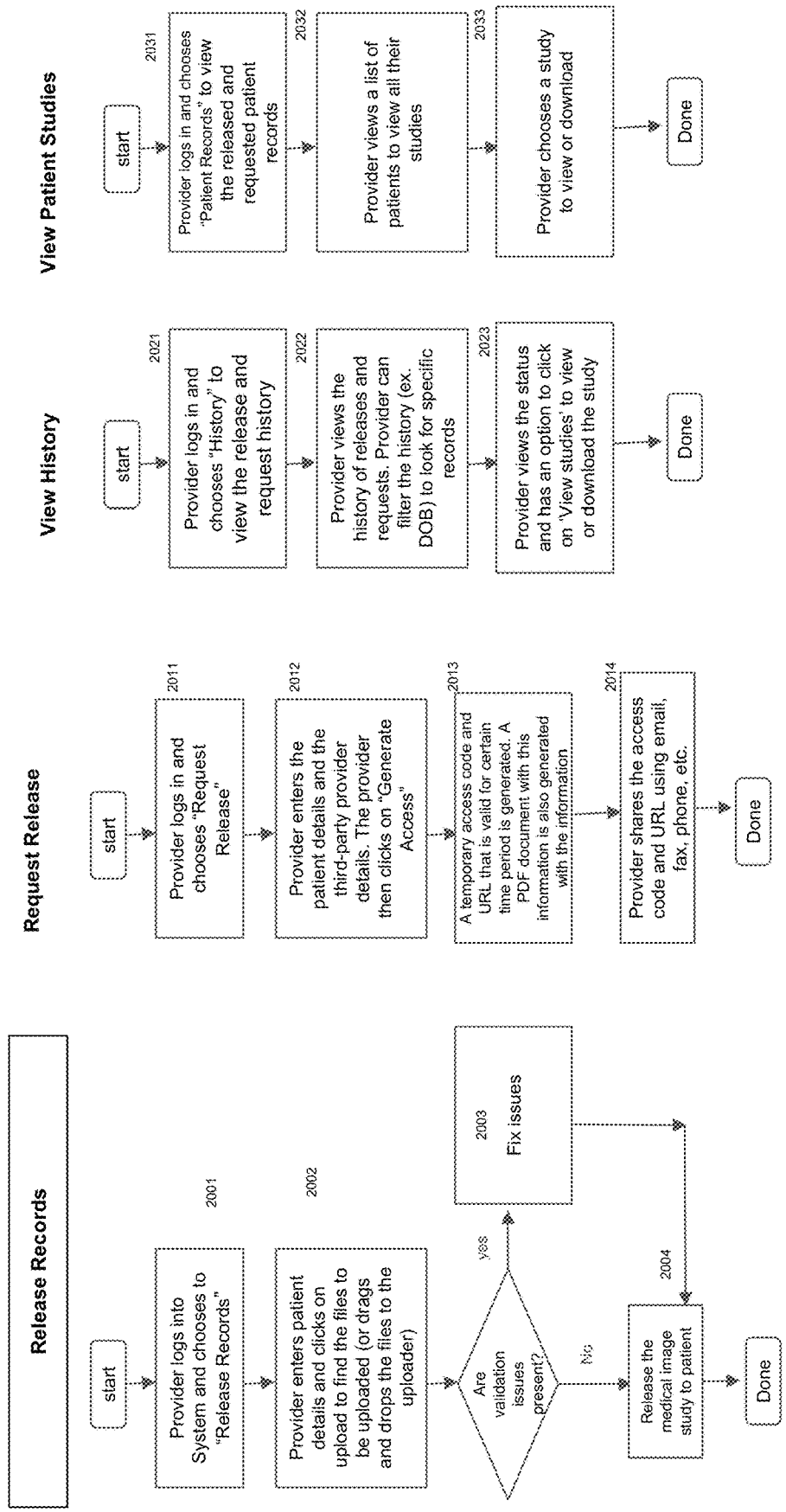

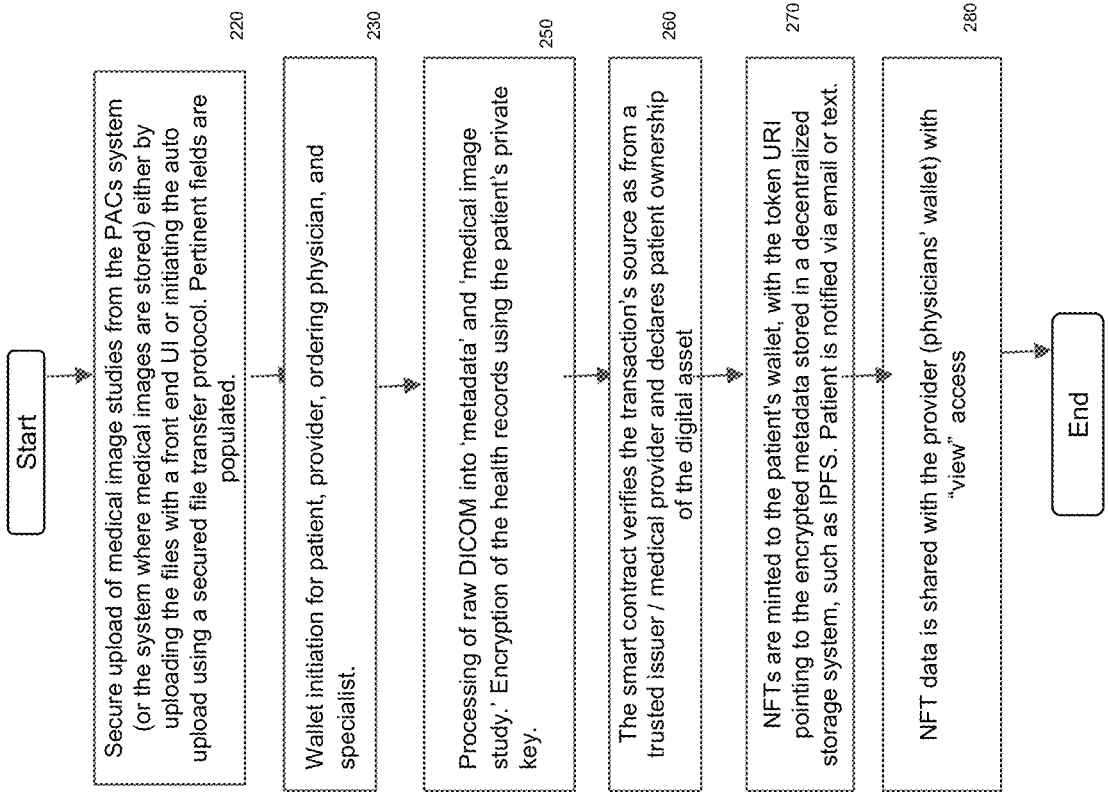
Fig 2B - Medical Imaging Provider User Flow Implementation

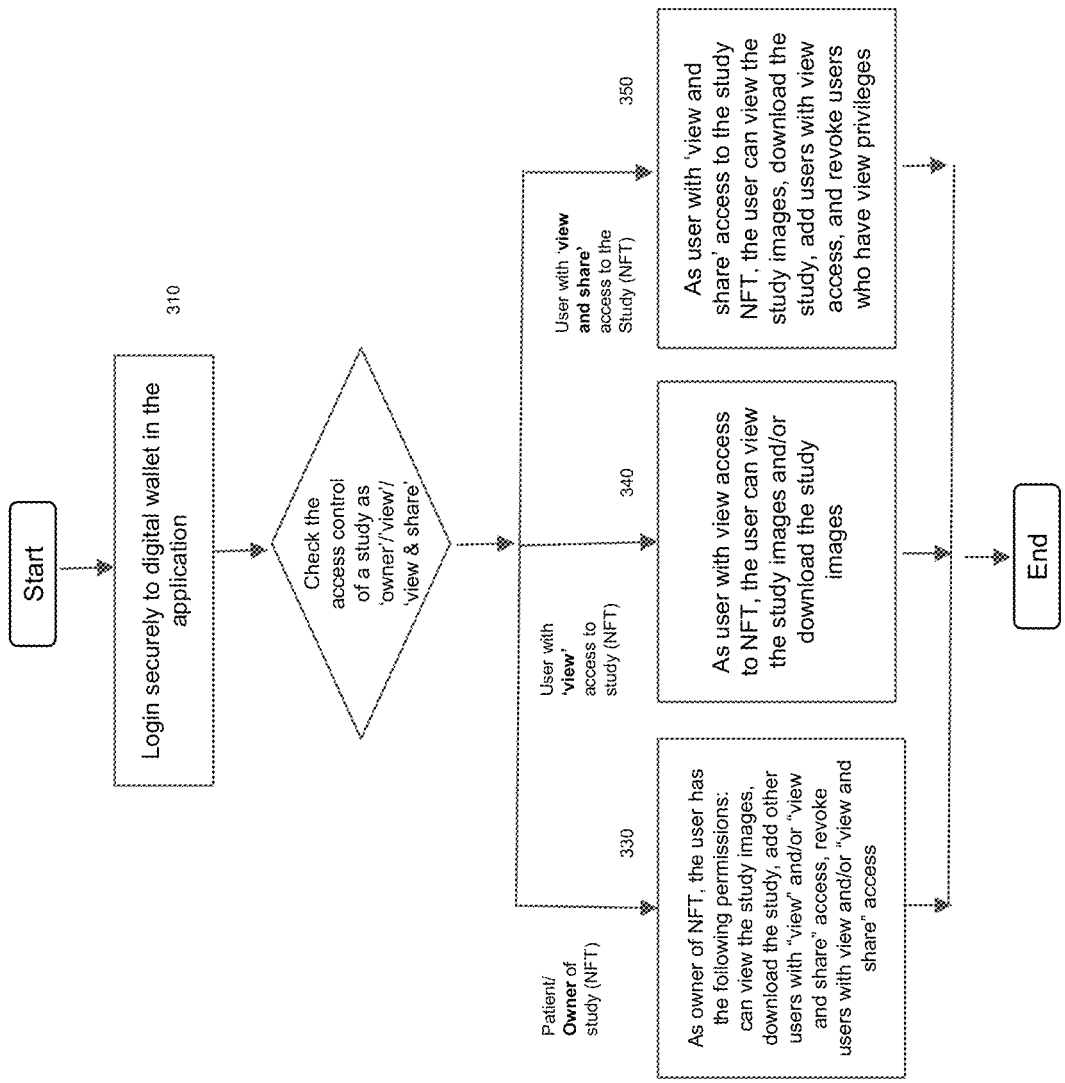
Fig 3 - User flows

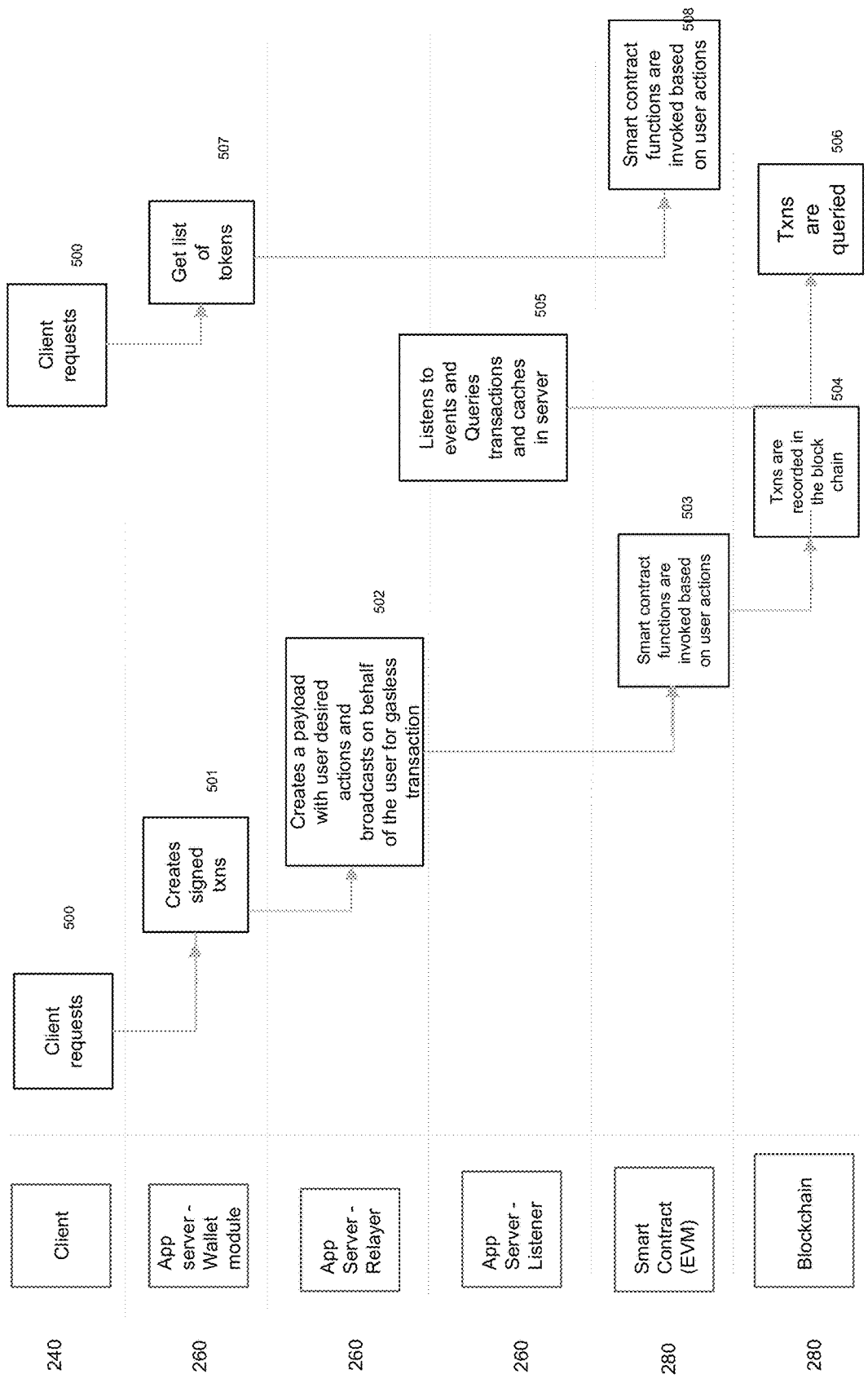
Fig 4 - Components Interaction

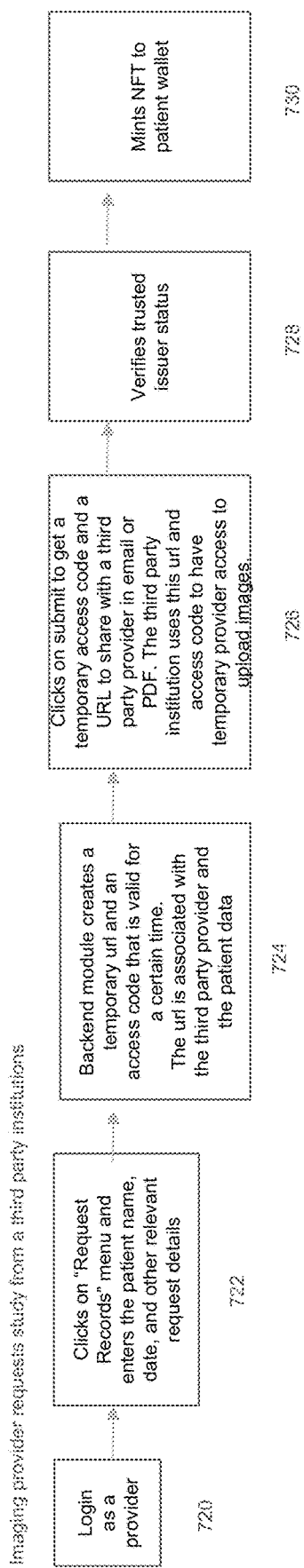

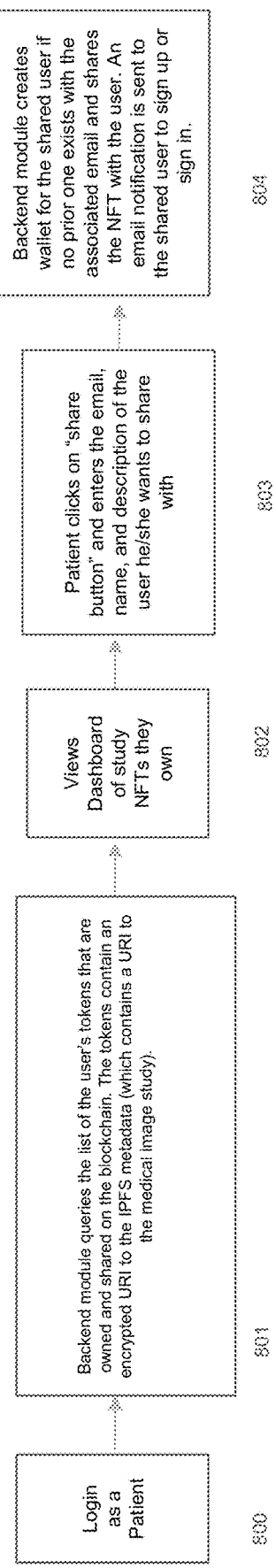
Fig 6a - Sample Implementation for Patient/owner journeys

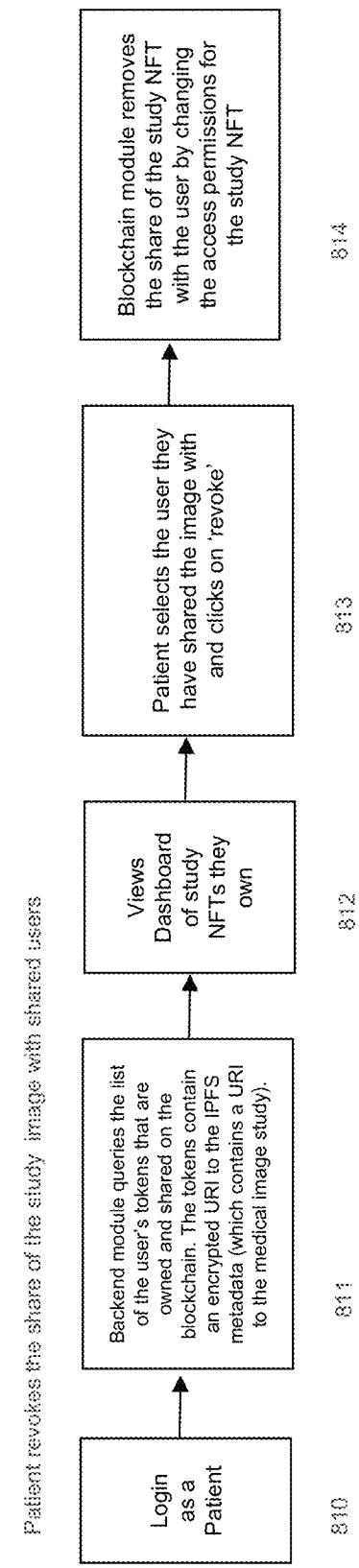
Fig 6b - Sample Implementation for Patient/owner journeys

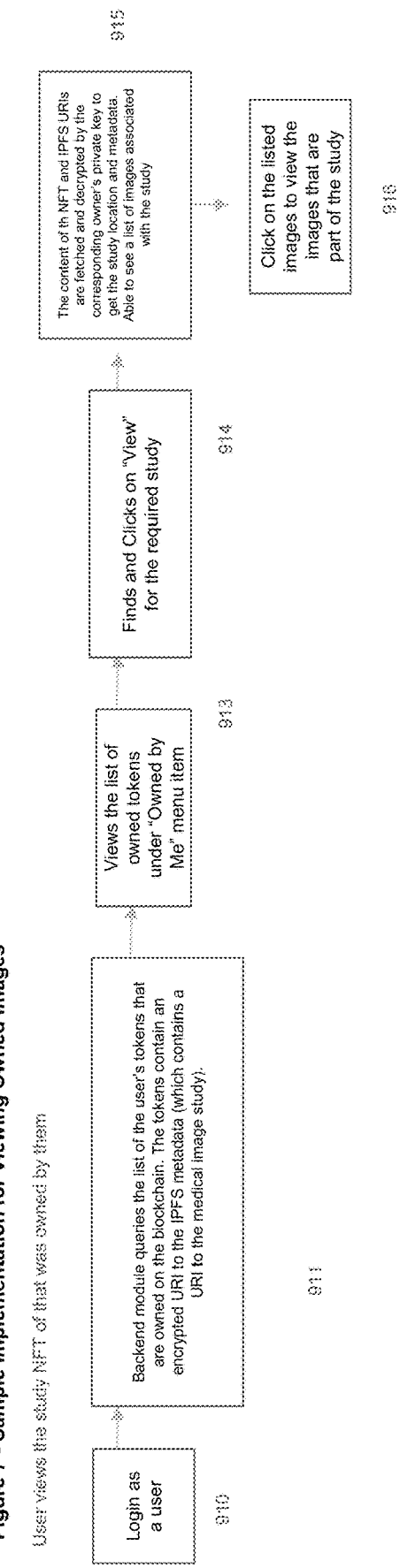

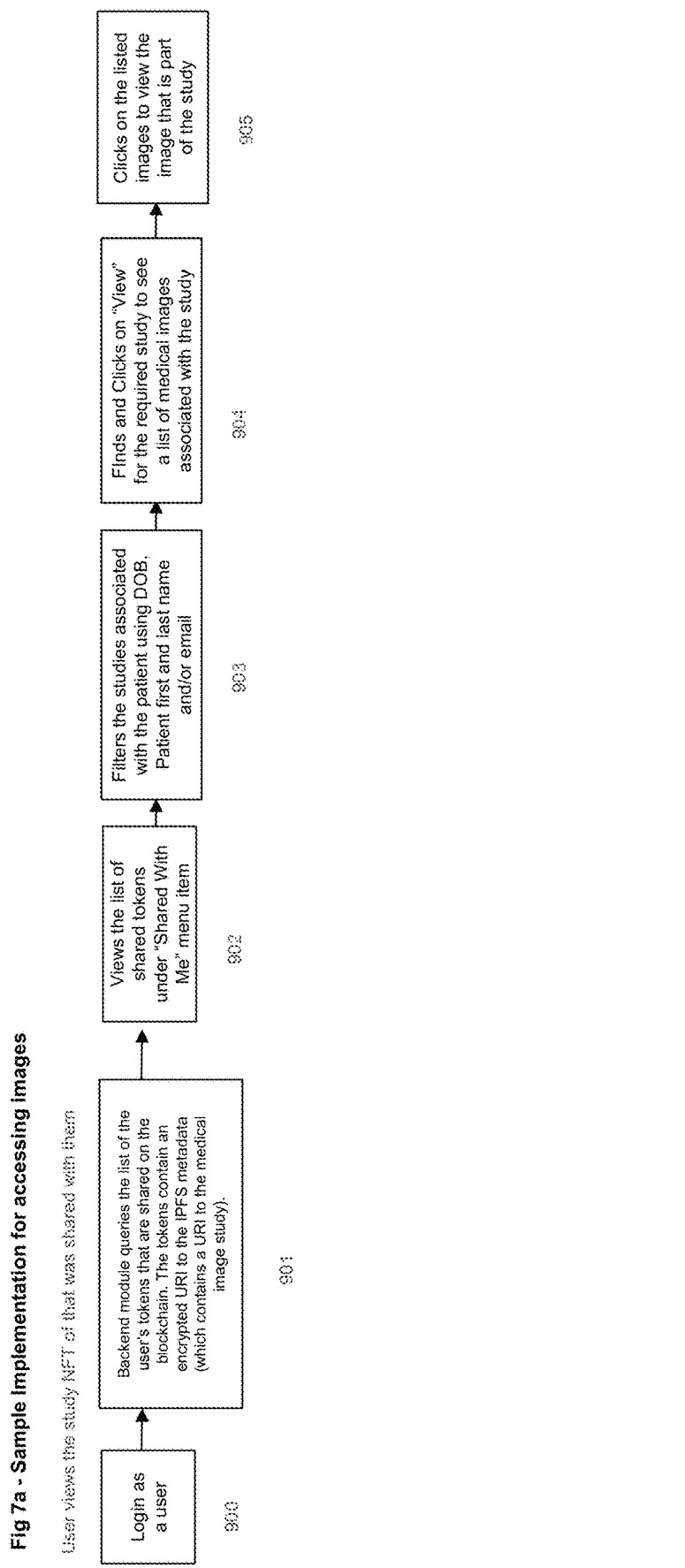
Fig 7a - Sample Implementation for accessing images

Fig 8 - Sample Implementation for automating the patient consent flow
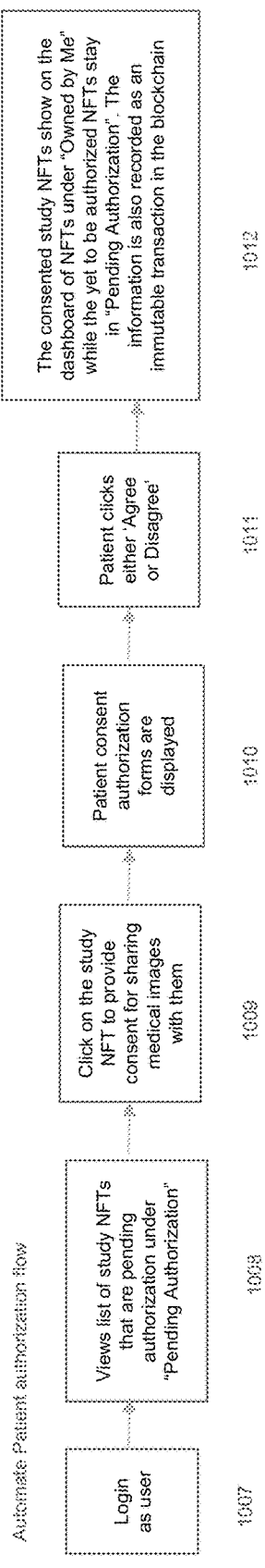
Fig 8a - Sample Implementation for recording consent on blockchain
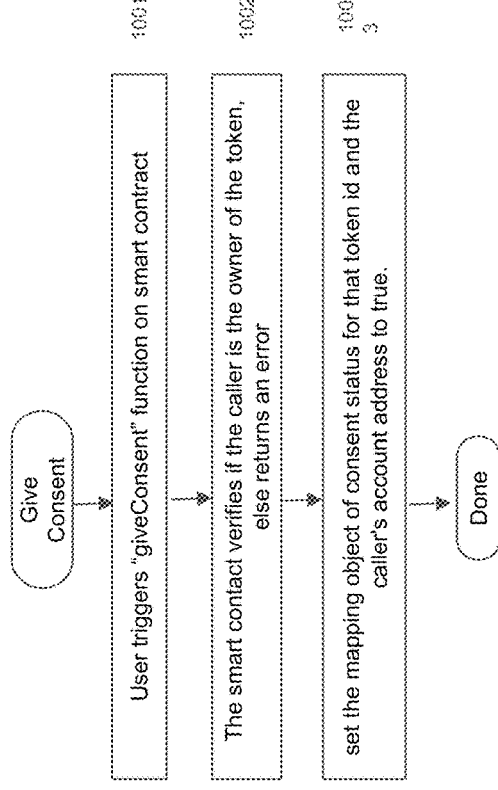
Fig 8b - Sample Implementation for querying the consent status on blockchain
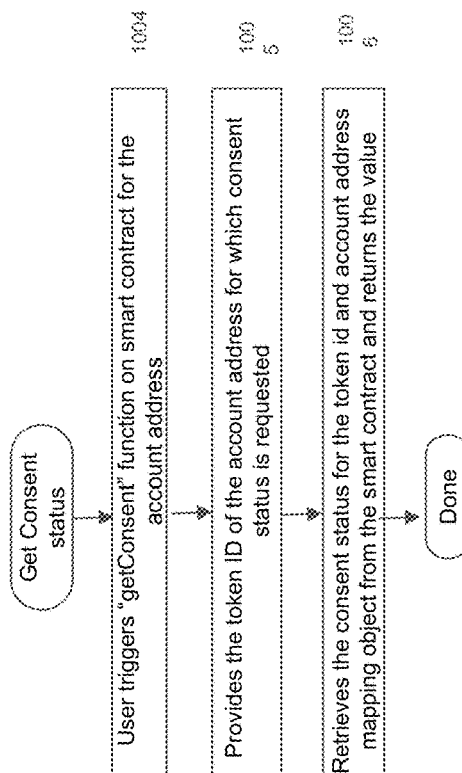

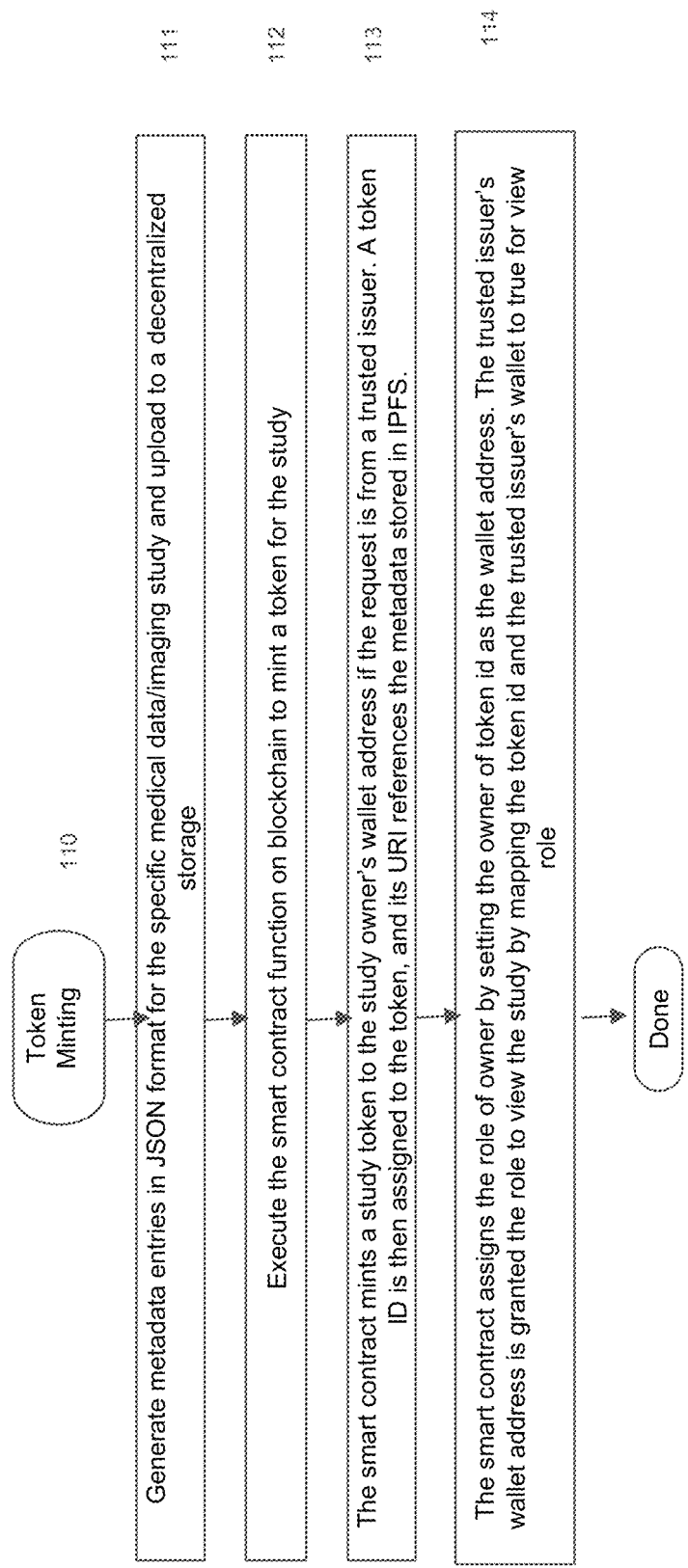

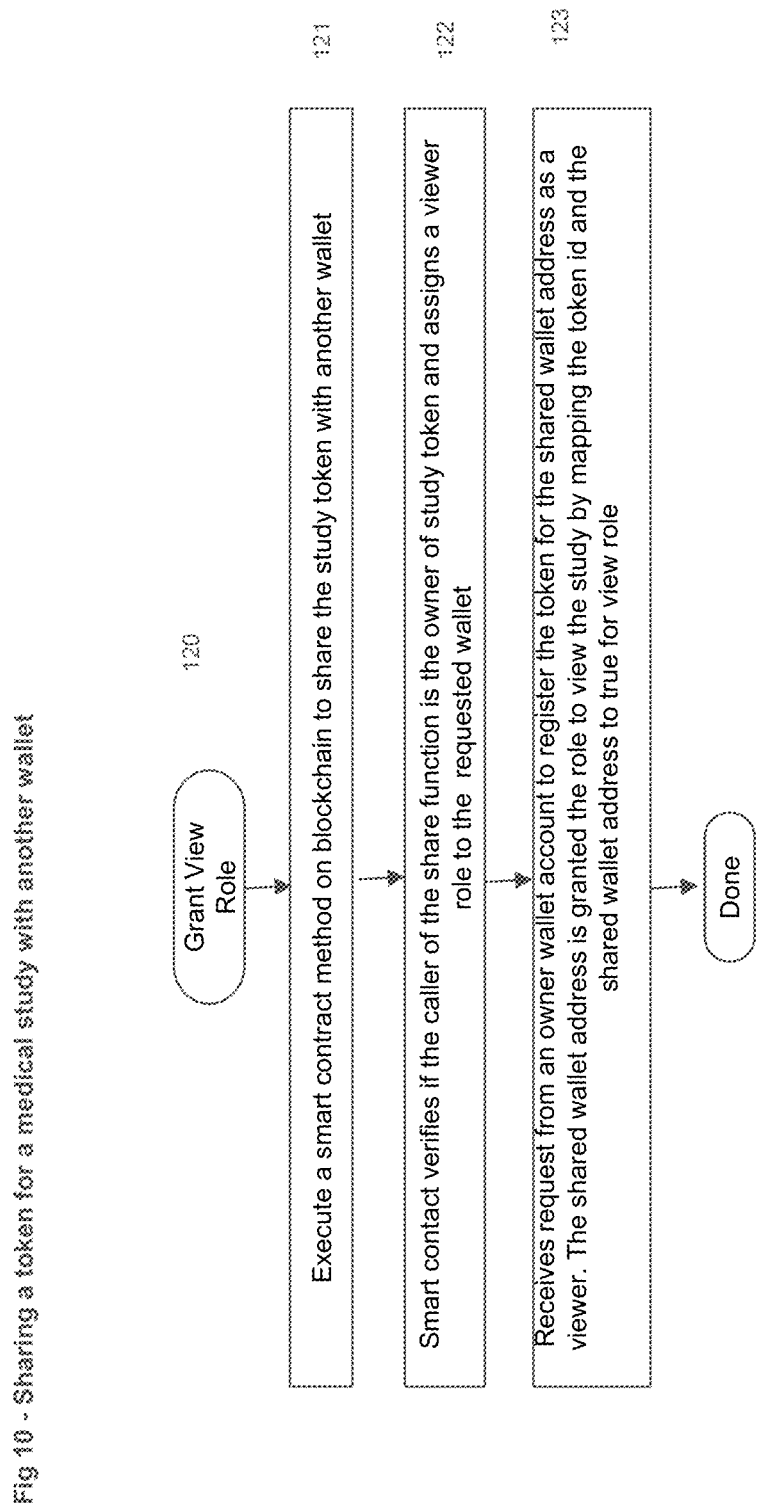

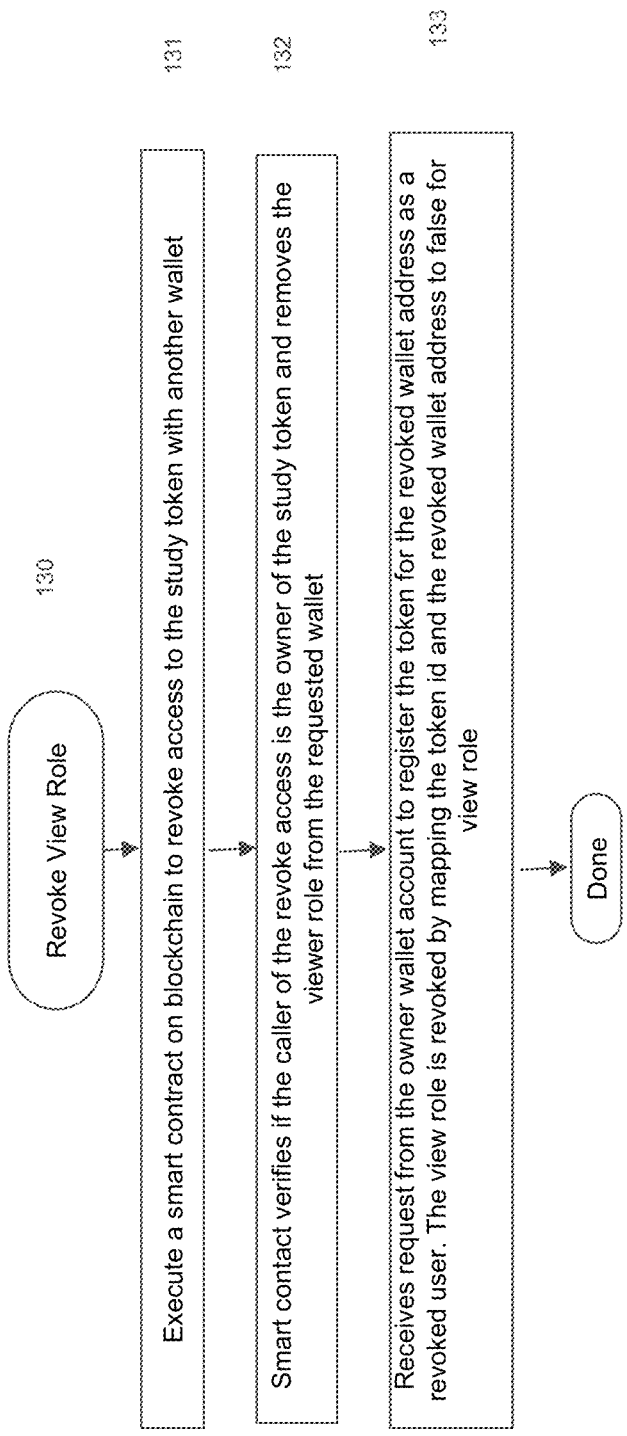

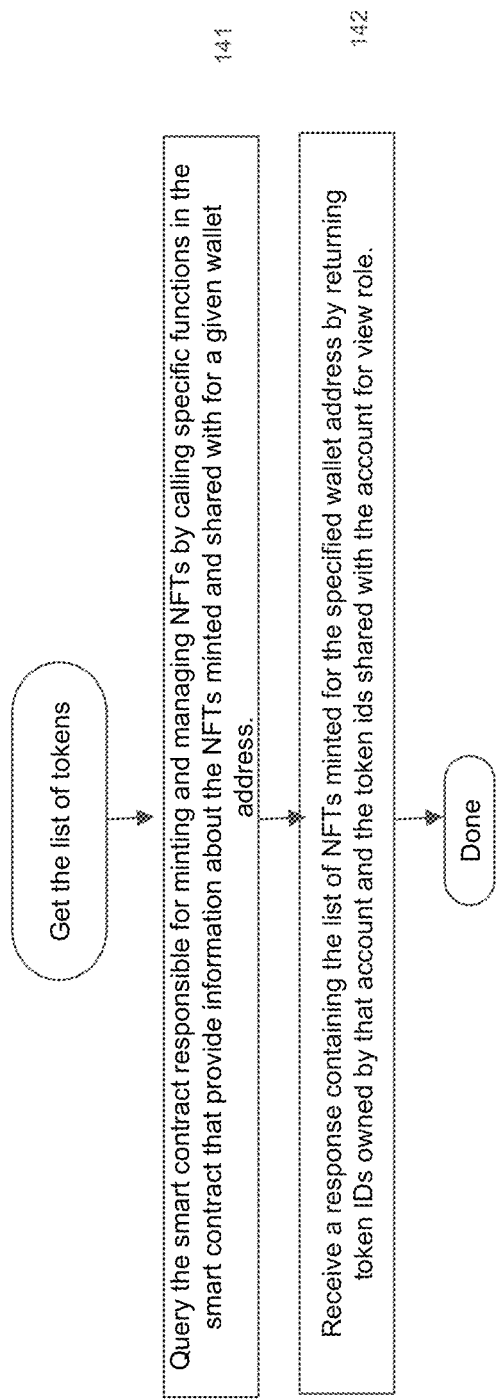
Fig 12 - Get a list of tokens that belongs to a wallet address

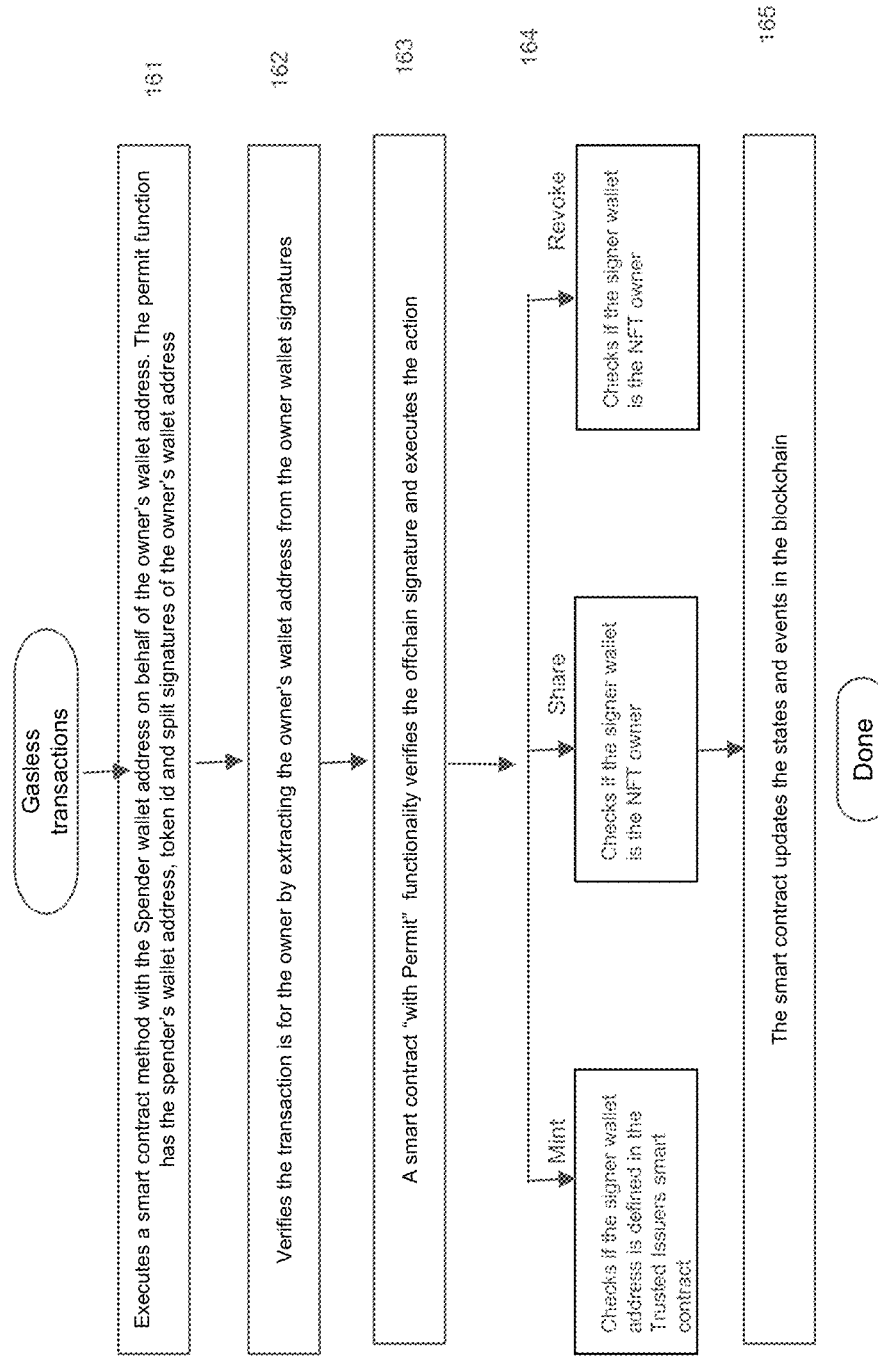

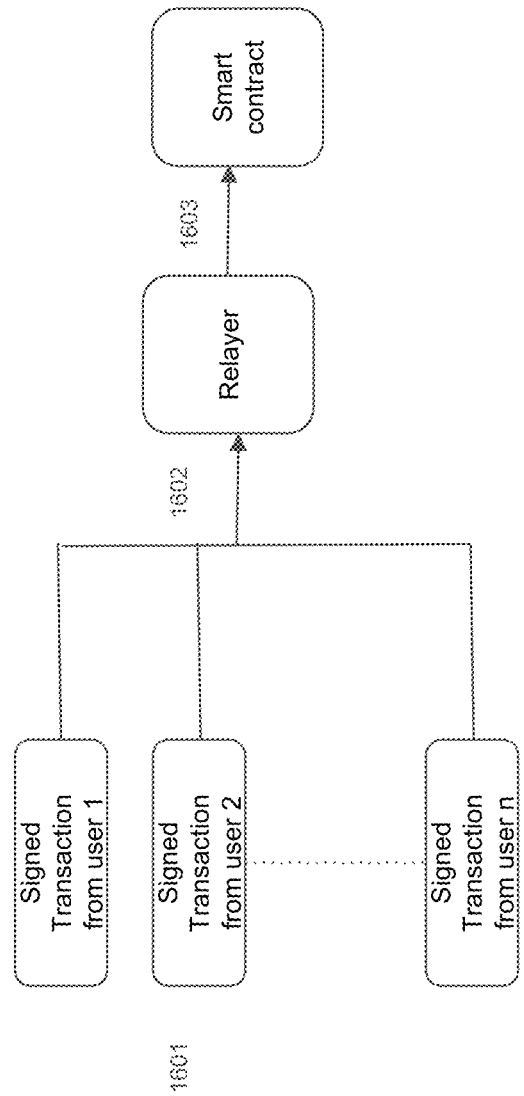
Fig 13a - Gasless Transaction

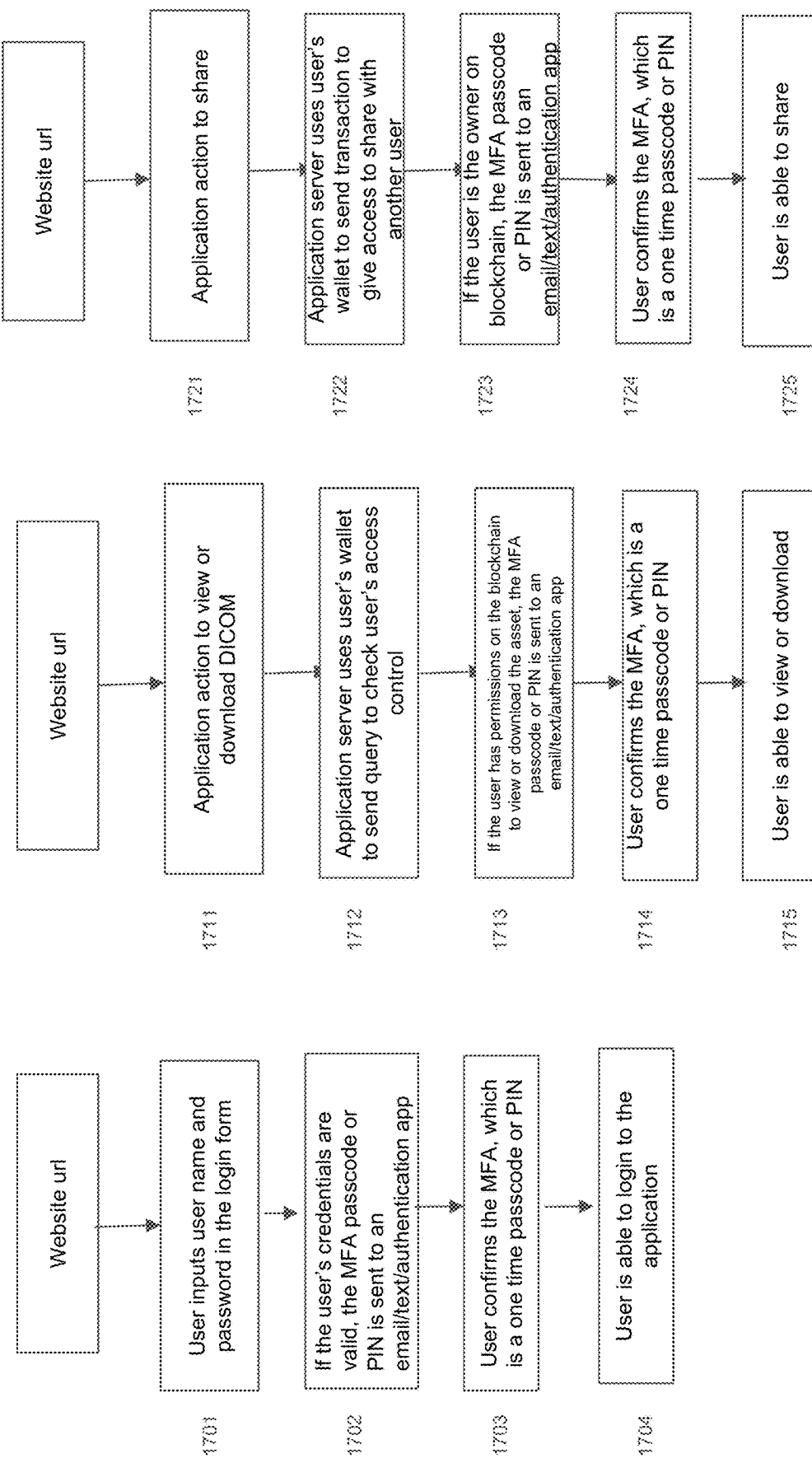
Fig 14 - Multi Factor Authentication

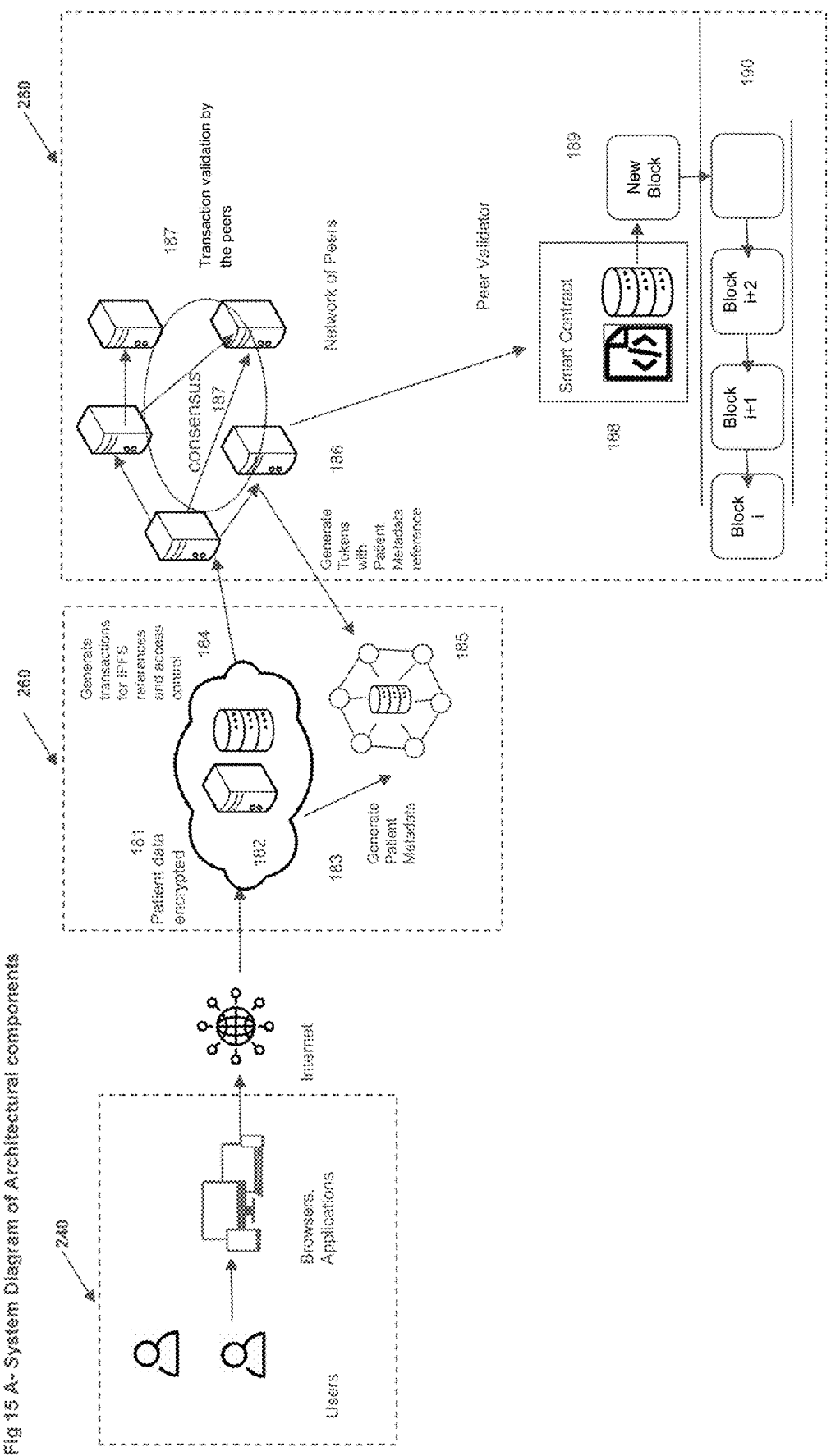
Fig 15 A - System Diagram of Architectural components

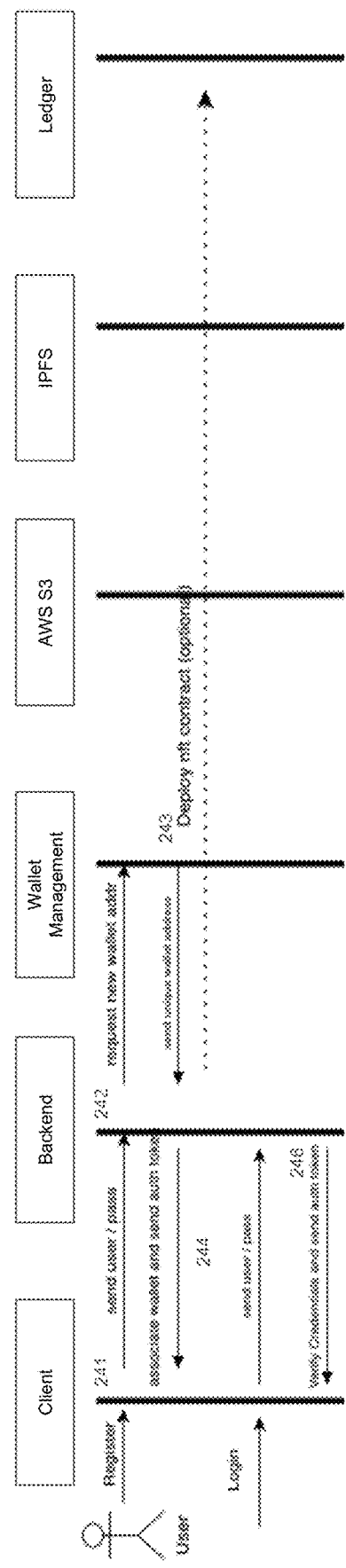

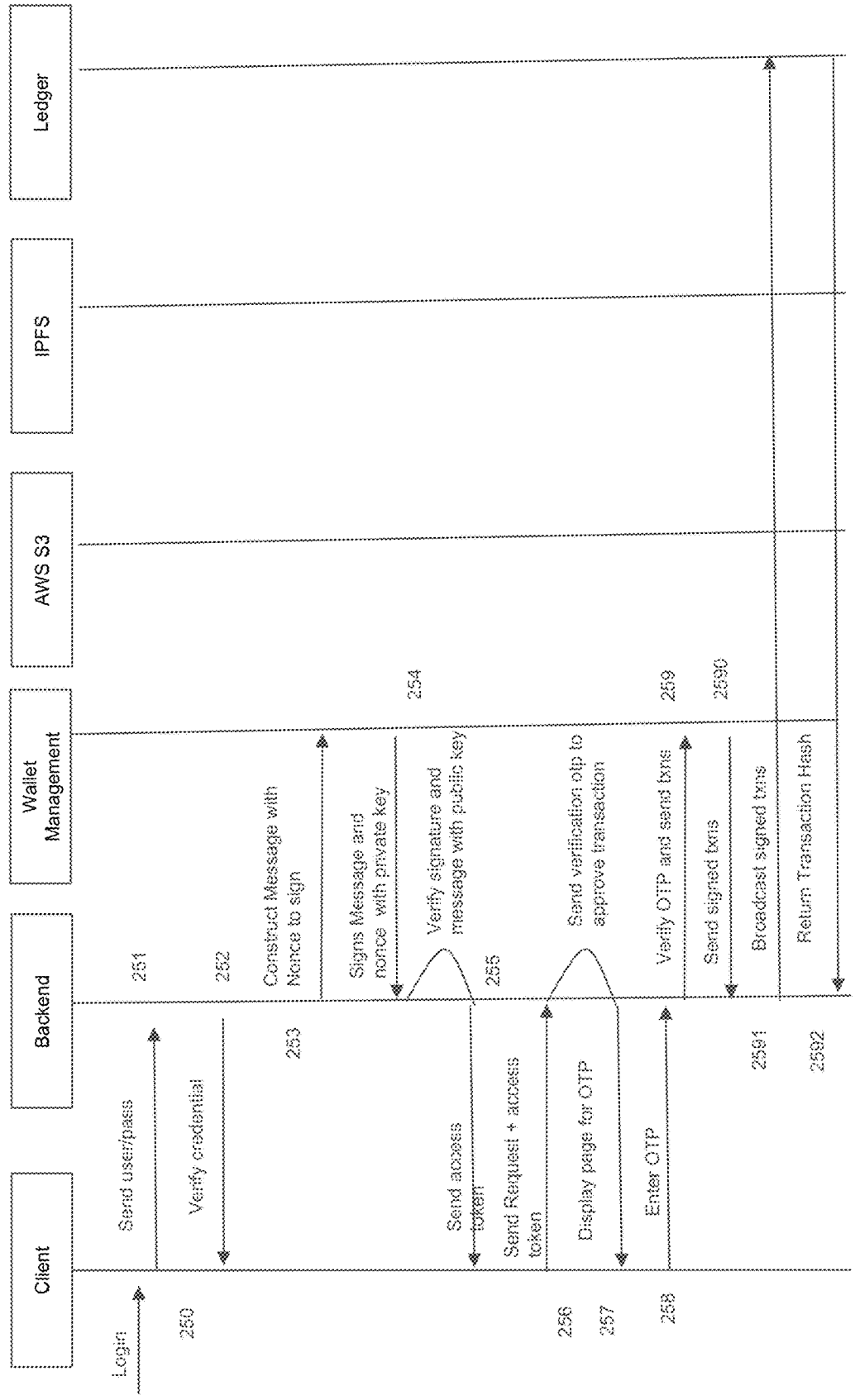

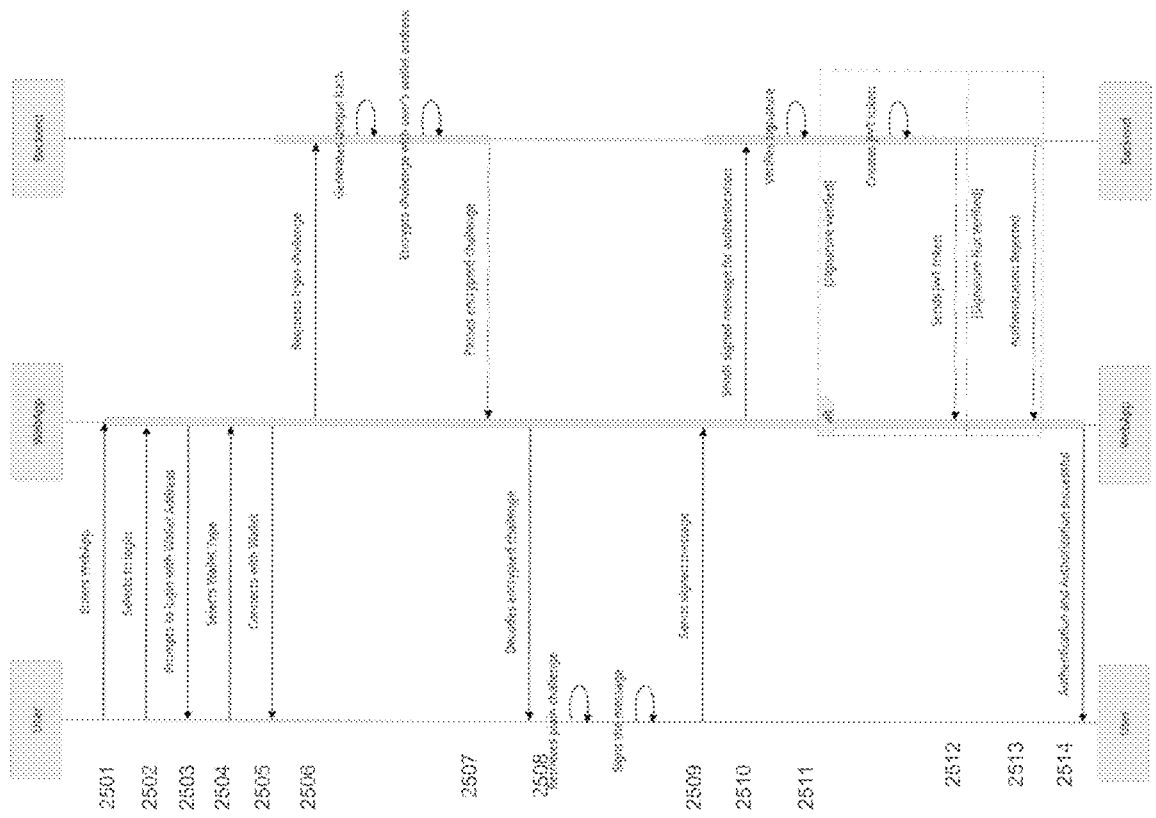
Fig 17a - Wallet Authentication

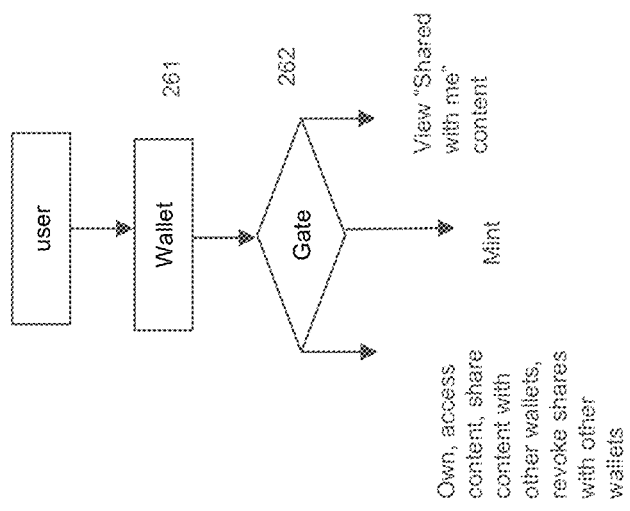
Fig 18- Wallet Gating

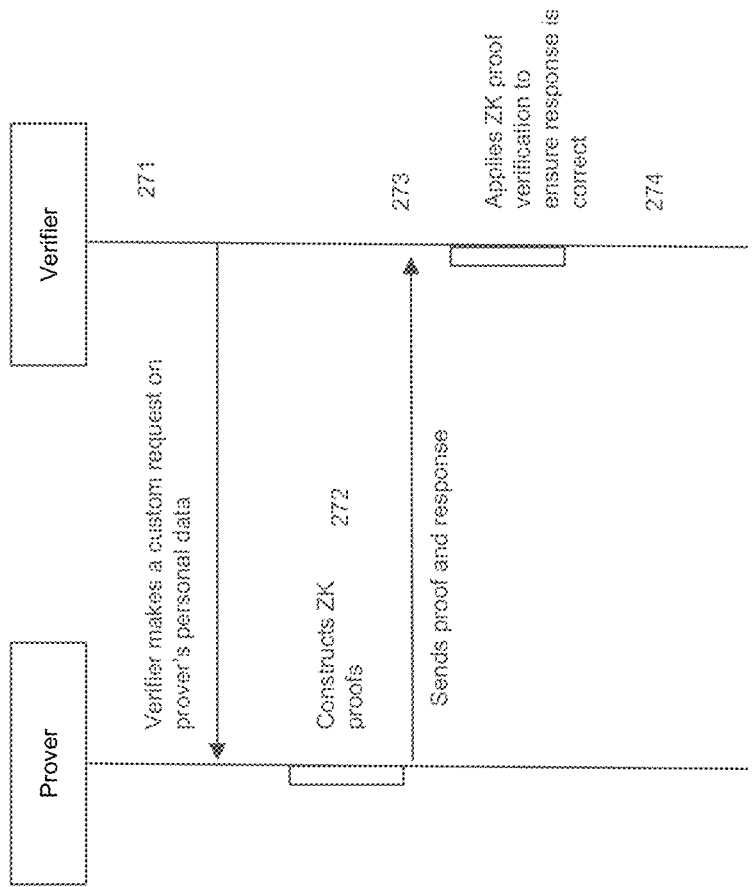

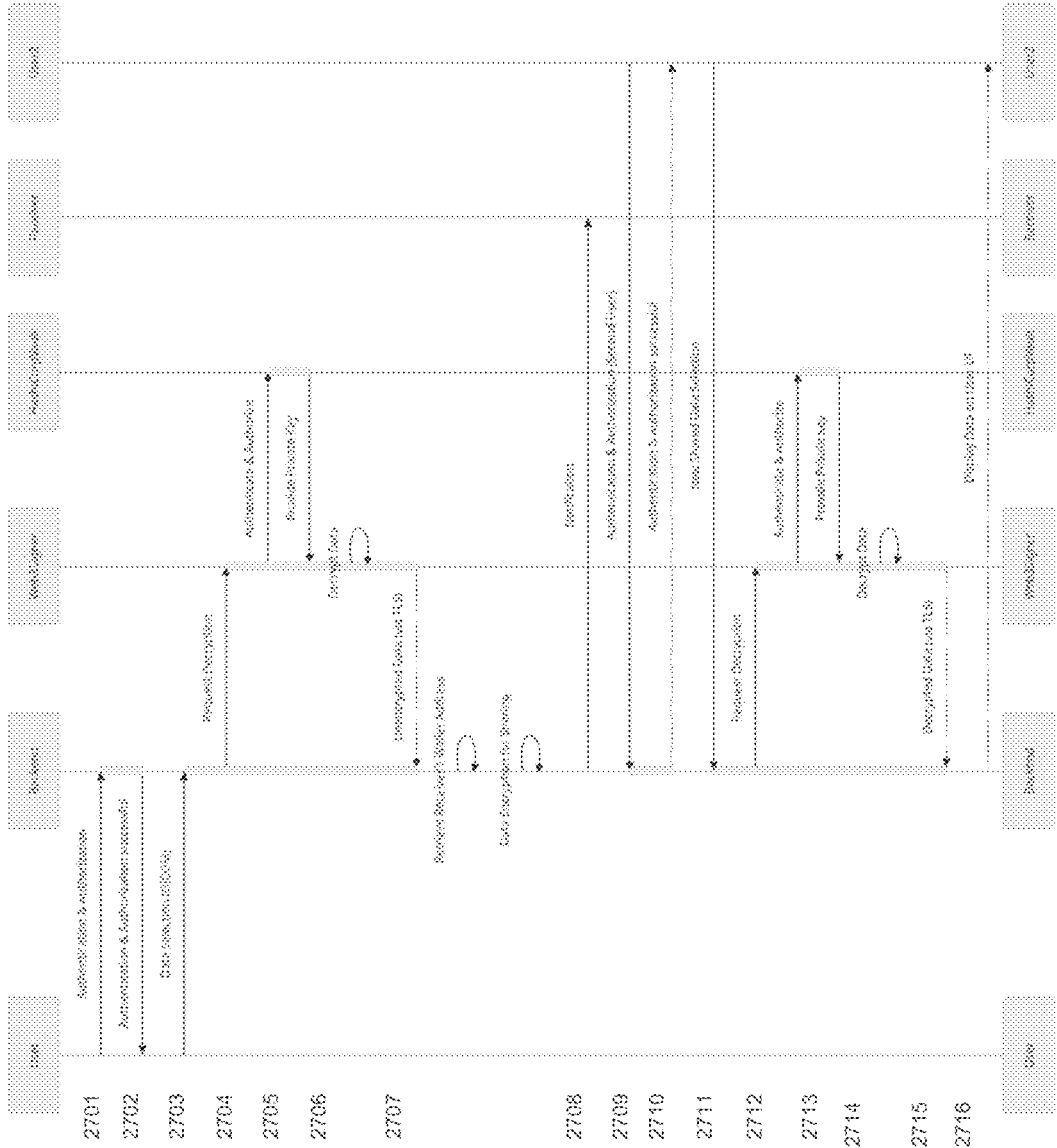
Fig 19a - Zero Knowledge Proofs

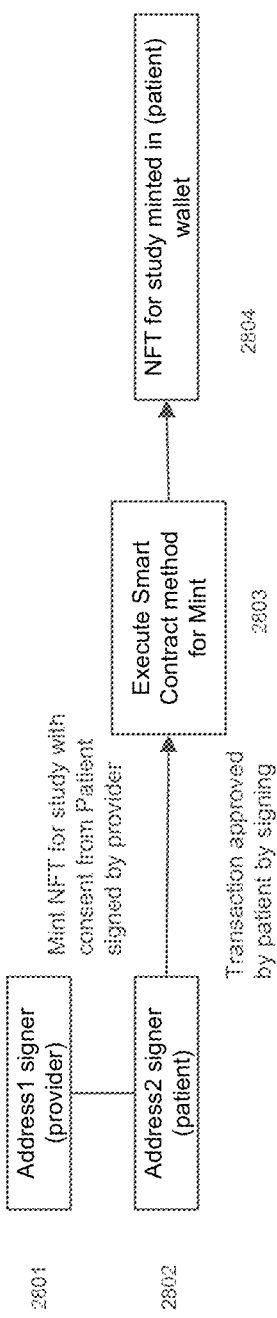
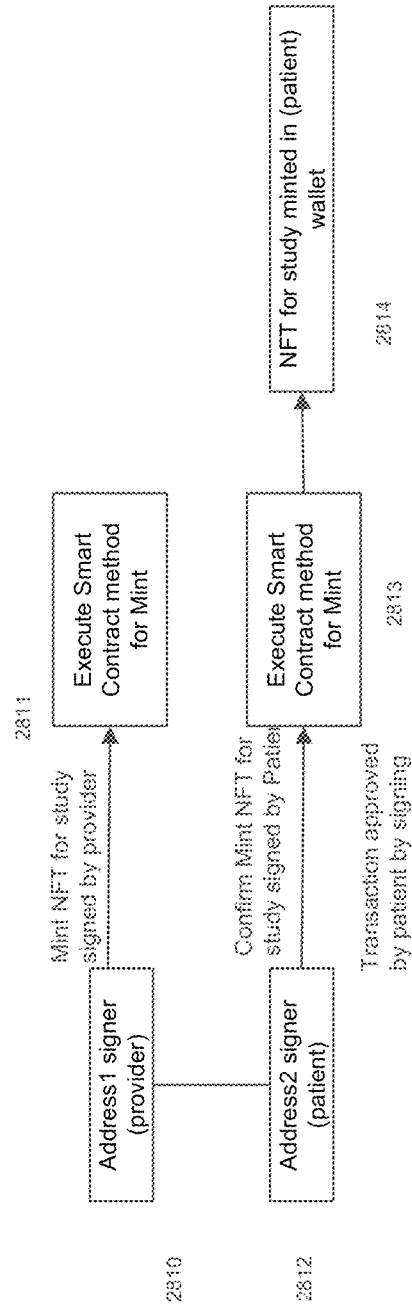

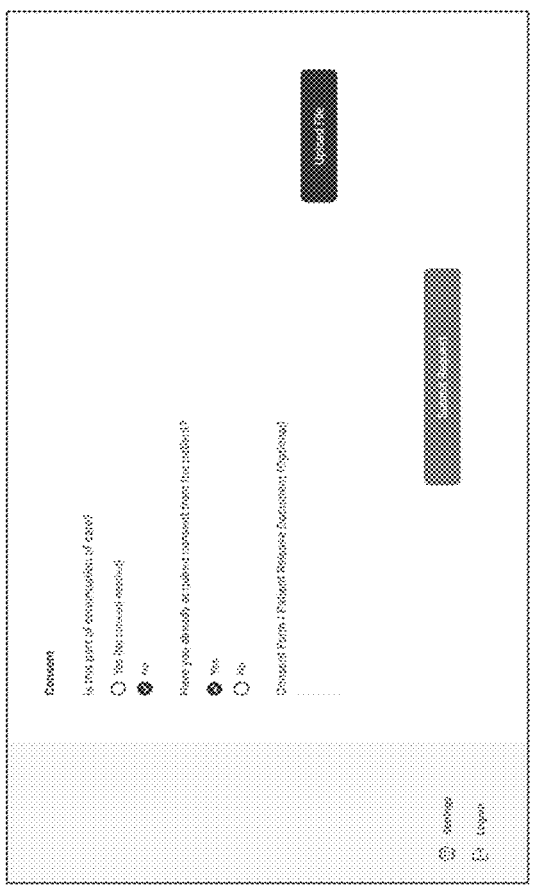
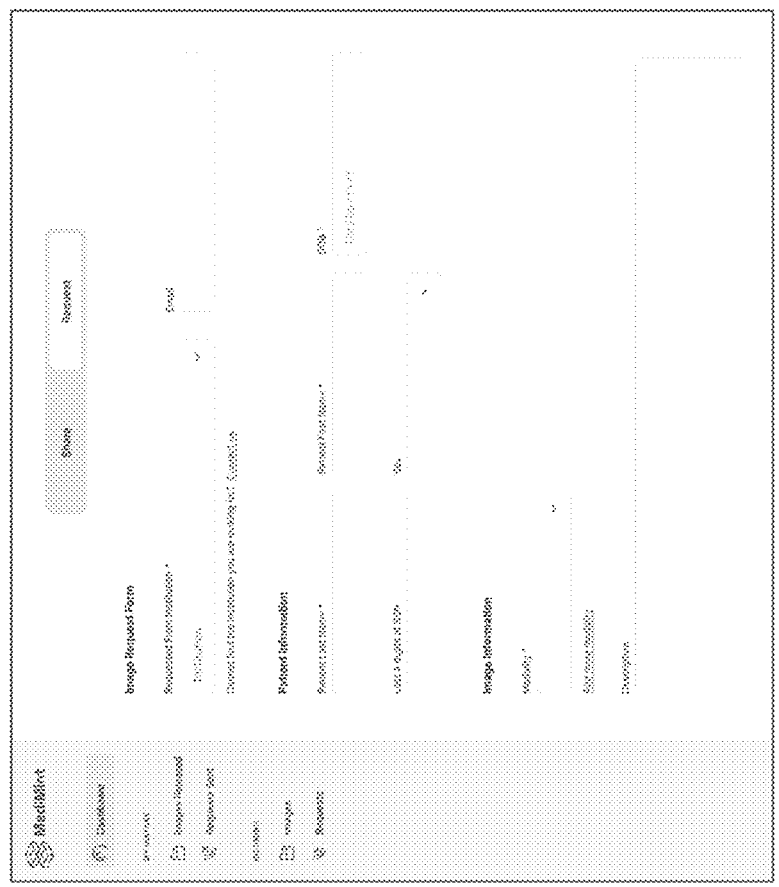
Fig 21 - Request Medical Images

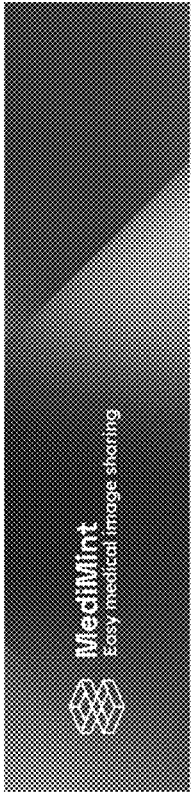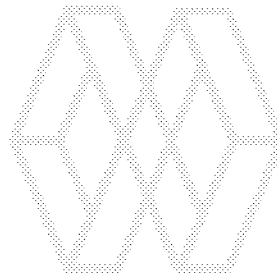
Fig 22 - Fulfill Request of Images

Fig 23 - View History of Transactions

| Study date | Study name | Patient | Date of birth | Physician | Uploaded date | Status | |
|---|---|---|---|---|---|---|---|
| March 25, 2024 12:24 AM | Lung CT | Michael John | June 15, 1998 | John Doe | March 25, 2024 12:24 AM | Processing | View study |
| March 25, 2024 12:24 AM | Lung CT | Michael John | June 15, 1998 | John Doe | March 25, 2024 12:24 AM | Error | View study |
| March 25, 2024 12:24 AM | Lung CT | Michael John | June 15, 1998 | John Doe | March 25, 2024 12:24 AM | Success | View study |
| March 25, 2024 12:24 AM | Lung CT | Michael John | June 15, 1998 | John Doe | March 25, 2024 12:24 AM | Success | View study |
| March 25, 2024 12:24 AM | Lung CT | Michael John | June 15, 1998 | John Doe | March 25, 2024 12:24 AM | Success | View study |
| March 25, 2024 12:24 AM | Lung CT | Michael John | June 15, 1998 | John Doe | March 25, 2024 12:24 AM | Success | View study |
| March 25, 2024 12:24 AM | Lung CT | Michael John | June 15, 1998 | John Doe | March 25, 2024 12:24 AM | Success | View study |
| March 25, 2024 12:24 AM | Lung CT | Michael John | June 15, 1998 | John Doe | March 25, 2024 12:24 AM | Success | View study |

1 2 3 ... 8 Next page

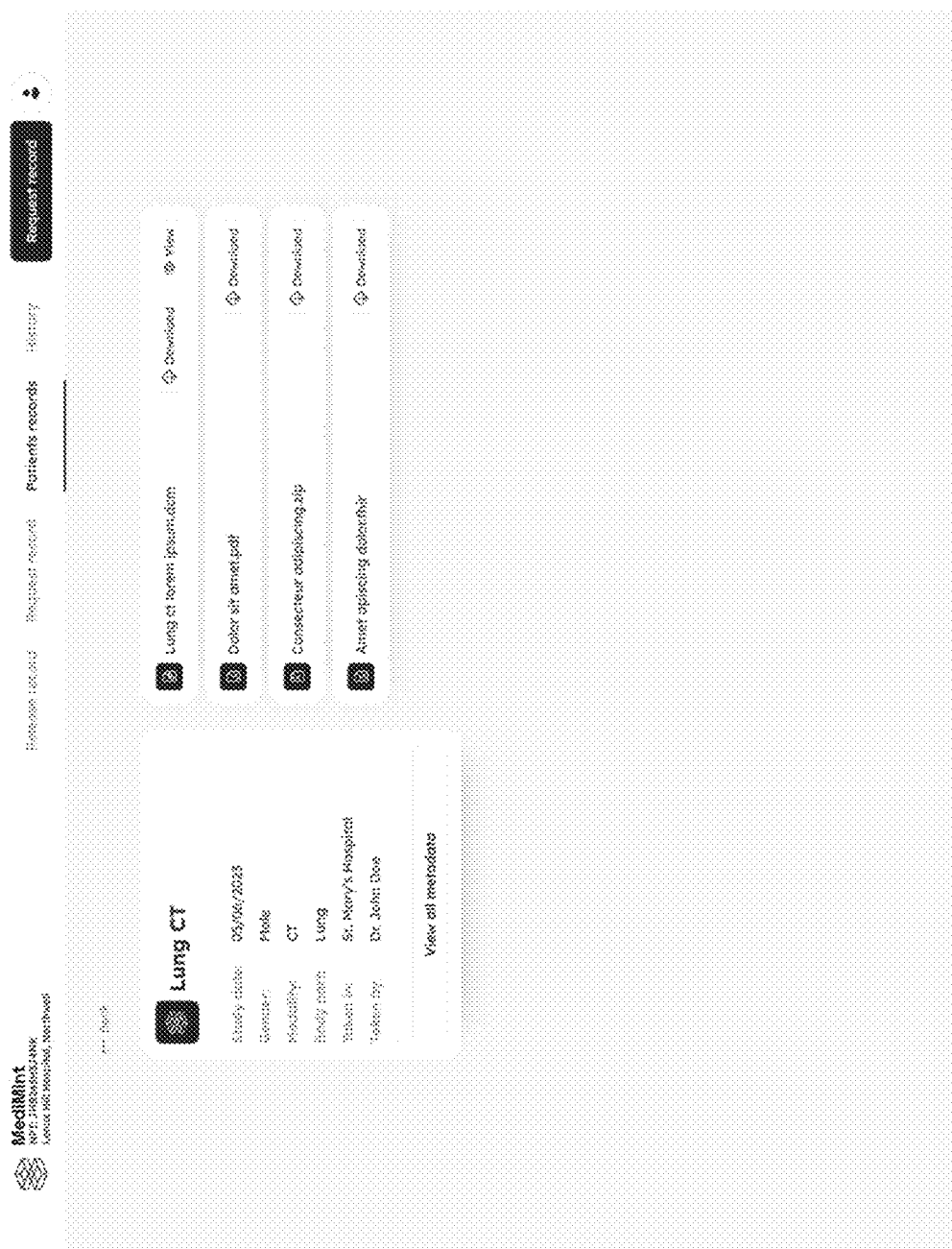
Fig 24 - View Study

Fig. 25 - Patient Records

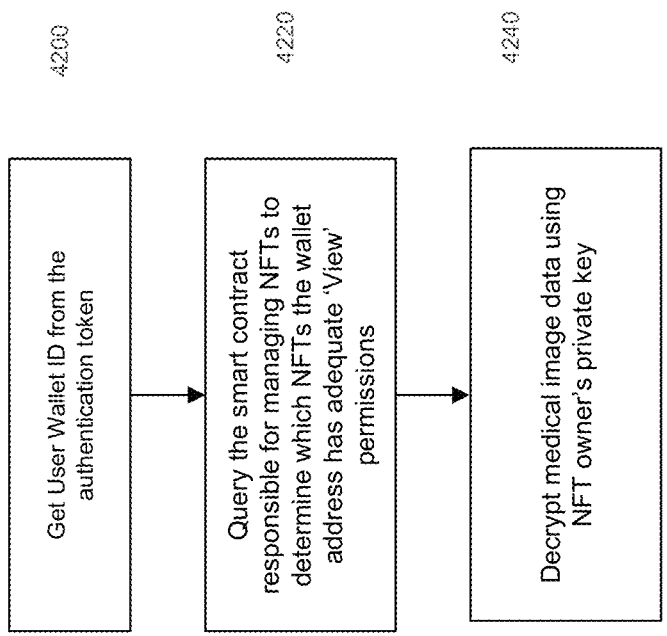

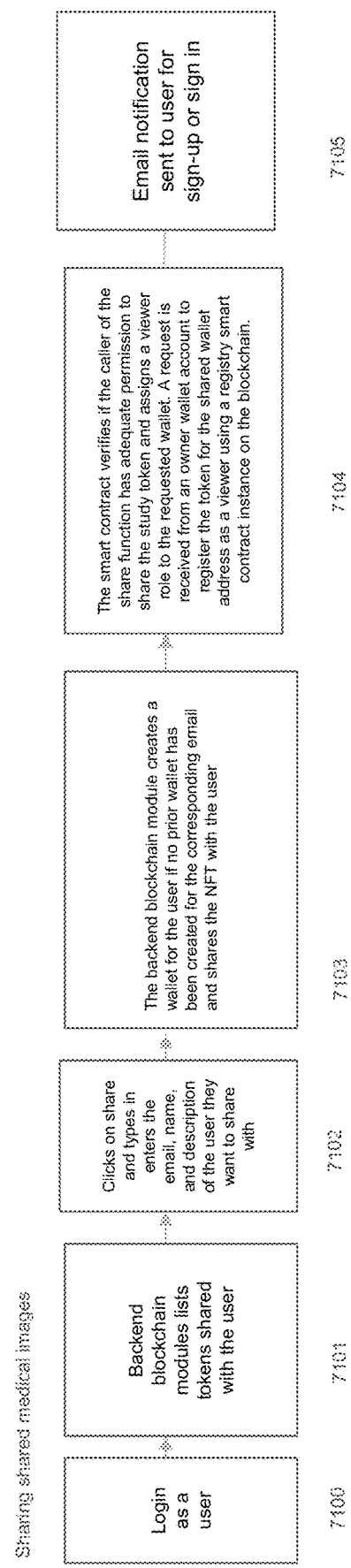

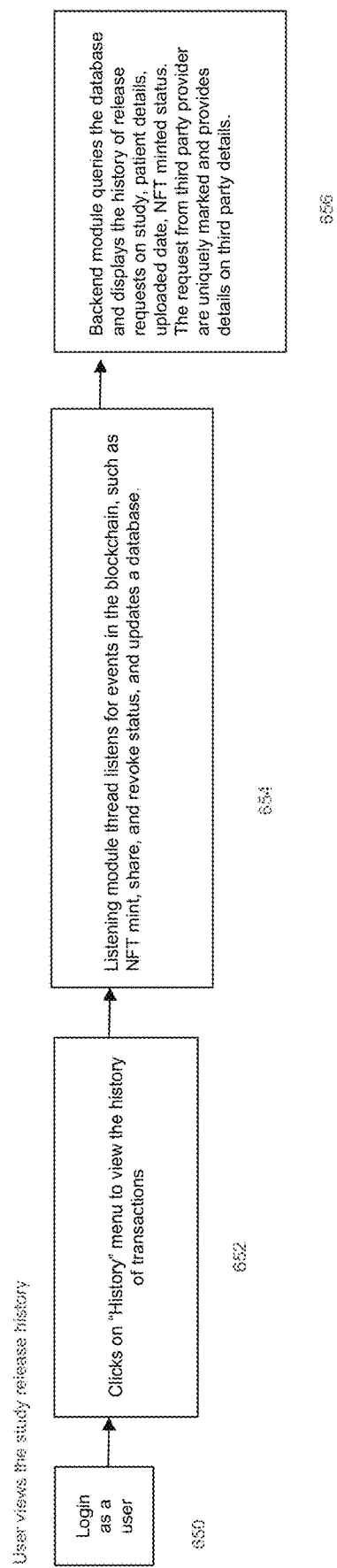
Fig 28 - Sample Implementation for User journeys

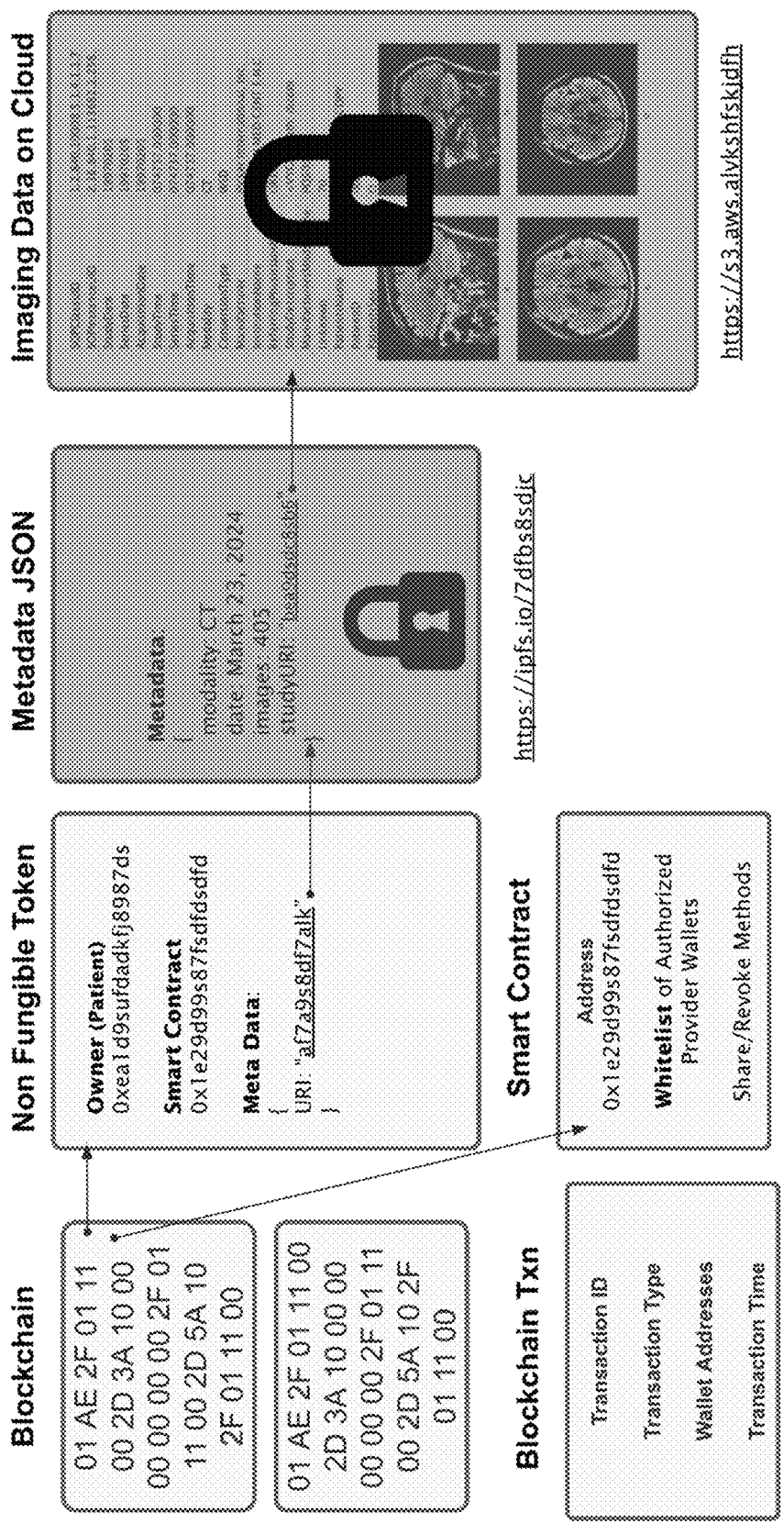
Fig 29 - Sample representation of Non Fungible Token on Blockchain

PATIENT-EMPOWERED DATA MANAGEMENT: A SECURE BLOCKCHAIN ARCHITECTURE WITH DECENTRALIZED OWNERSHIP

RELATED APPLICATION

This application claims the benefit of U.S. Provisional Application No. 63/469,730, filed May 30, 2023, the entire contents of which are incorporated herein by reference.

BACKGROUND

Background of the Related Art

For several decades, managing and transmitting medical data has faced several significant challenges. Traditionally, medical data resided in individual hospitals or healthcare providers, often stored on physical servers within their own facilities. This local storage approach made it difficult for patients to access their own information and for authorized providers from different institutions to collaborate efficiently. The need for efficient data exchange spurred the migration from isolated, local storage within individual healthcare institutions to cloud-based solutions.

While cloud storage offered improvements in accessibility and scalability, it fell short in crucial areas. Different healthcare providers often utilized incompatible EHR systems, hindering data exchange and creating interoperability issues. This siloed approach hampered collaboration and efficient care coordination across institutions. Furthermore, cloud storage often functioned as a "black box," with patients lacking control and transparency over how their data was used or shared. The centralized nature of cloud systems meant a single entity-controlled access, potentially limiting patients' ability to access their own information. These limitations, coupled with lingering security concerns about data breaches and privacy, underscored the need for a more decentralized and patient-centric approach to medical data management.

Limitations of Cloud Storage include:

Limited Control: Healthcare providers still ceded some control over their data to cloud service providers.

Potential Downtime: System outages or disruptions at the cloud provider could hinder access to critical medical records.

While cloud technology offered a significant leap forward in medical data management, its centralized architecture introduced a critical vulnerability-a single point of failure-which can exacerbate security breaches:

Centralized Access Management: Cloud storage systems rely on a centralized access control mechanism. If a hacker gains access to this system, they could potentially steal a vast amount of sensitive medical data in one fell swoop. This poses a significant risk, as medical records often contain highly confidential information like diagnoses, medications, and financial details.

Vendor Dependence: Healthcare providers trusting cloud storage become reliant on the security practices of the cloud service provider. A security breach within the cloud provider's infrastructure can expose a vast amount of sensitive data. While cloud providers invest heavily in security, even the most robust systems can be compromised.

Insider Threats: Malicious actors within the cloud service provider, with authorized access, could potentially steal or misuse patient data. Centralized access control systems don't eliminate this insider threat entirely. The consequences of such breaches can be devastating:

Patient Privacy Violations: Exposed medical data can be used for identity theft, targeted advertising, or even blackmail. Patients can suffer emotional distress and reputational damage due to such privacy violations.

Financial Losses: Medical identity theft can lead to fraudulent charges on patients' health insurance or even attempts to obtain medical care under a stolen identity.

Regulatory Fines: Healthcare providers face hefty fines and reputational damage if they fail to comply with data privacy regulations like HIPAA.

Overall, this siloed approach made it difficult for patients to access their own data or for authorized providers to obtain records from other institutions efficiently, resulting in delays in patient care, inability to access their records ahead of appointments in a timely fashion, and even lost medical records, resulting in misdiagnosis.

These limitations led to inefficiencies in healthcare delivery, hindered collaboration between providers, and restricted patients' ability to manage their own health information. Sharing medical data between different healthcare providers was often a cumbersome and time-consuming process. Manual requests, faxed documents, and compatibility issues between different electronic health record and picture archiving and communication systems created significant hurdles.

Blockchain offers a decentralized and secure alternative for managing medical records, potentially addressing the remaining concerns about data privacy, control, and security. For instance, "A Novel Secure Blockchain Framework for Accessing Electronic Health Records Using Multiple Certificate Authority" (2020) by Wang et al., proposes a framework for accessing Electronic Health Records (EHRs) using a private blockchain with multiple Certificate Authorities (CAs). It highlights the security and privacy benefits of private blockchains in healthcare.

"How a private blockchain for healthcare could revolutionize the industry" by Solix Technologies, discusses the potential of private blockchains to improve the healthcare industry by addressing issues like fragmented EHR systems. It mentions the limitations of private blockchains, including cost and scalability. "IRJET-Transaction of Healthcare Records using Blockchain" (2019) by Kavitha et al., explores the use of blockchain technology for secure and transparent healthcare record management. It mentions the advantages of private blockchains, such as controlled access and regulatory compliance, while acknowledging the potential downsides like cost and scalability challenges.

While blockchain technology has been generating excitement for its potential to revolutionize healthcare data management, traditional implementations often relied on a specific design with inherent limitations. These earlier solutions typically utilized private or permissioned blockchains. Here, a limited group of authorized participants, like healthcare providers or institutions, controlled access to the network. While this approach offered advantages like ensuring privacy and meeting regulatory requirements, it came at a significant cost. Building and maintaining a private blockchain infrastructure requires substantial investment from healthcare organizations.

Permissioned and private blockchains operate in a more controlled environment, with restricted membership. Access to the network and participation in consensus mechanisms are granted solely to pre-authorized members, typically defined by a central authority or consortium. This introduces a single point of failure and reduces the inherent security and trust associated with a decentralized public ledger.

Unlike private and permissioned blockchains, which are closed networks designed for speed and control within a limited group, public blockchains are open to anyone. This openness fosters transparency and security in public chains like Ethereum and Polygon. These "enterprise-ready" blockchains are addressing scalability concerns through innovative solutions, making them suitable for high-performance and secure business applications.

Furthermore, traditional approaches often involved storing the actual medical data directly on the blockchain ledger itself. Blockchain transactions inherently have associated costs, and storing large volumes of medical data on-chain can make these transactions very expensive. Additionally, the sheer size of the data can significantly slow down transaction processing times, hindering the overall efficiency of the system.

These limitations, coupled with the fact that private chains require users to specifically opt-in can create interoperability issues when bridging data between different chains, have spurred the need for an alternative approach that is more cost-effective and scalable for mass data exchange in industries like healthcare and unlock the full potential for secure and efficient data management that centers around the owners of the data.

SUMMARY OF THE DISCLOSURE

A novel, secure, and scalable framework and unique architecture is provided for managing user data on a hybrid blockchain and cloud platform. The architecture prioritizes user centricity by granting individual users control over their data through a unique key management system. Unlike traditional data storage models where a single entity holds the key, this approach empowers data owners to act as custodians of their own records.

This secure "highway" leverages blockchain technology to provide tamper-proof data storage and transparent access control. The framework employs innovative techniques for user-friendly private key management, ensuring data security without compromising usability.

The framework is chain-agnostic, supporting any private, permissioned, or public chain. Independent of the type of blockchain leveraged, the digital record on the blockchain, in the form of a non-fungible token, is designated ownership by the patient user account, and only stores a reference to a file on a decentralized storage platform, such as IPFS, of which file contains non-PHI metadata about the imaging study along with a unique identifier which references the location of the patient's specific medical data. When the patient wants to share their medical data, they can do so without compromising their true unique identifier or going through a central entity. The patient enjoys complete transparency, overseeing who has access to their medical data and the ability to revoke access at any time. Further, the patient becomes the manager of their own data from any healthcare institution, without having to be at the mercy of healthcare institutions. They can manage their records from a single pane of glass and have the records available at their fingertips, rather than having to manage several passwords and logins to portals, or deal with disparate types of mediums, and go through arduous medical record requests processes.

For physicians and healthcare institutions, a host of inherent advantages emerges. Sharing medical data with patients and requesting the prior medical data becomes easy. The arduous task of searching for a patient's medical data location is replaced with instant access, requiring only approval from the account owner (the patient). This not only saves valuable time but also streamlines workflows, enhances diagnostic accuracy, and ultimately elevates the quality of patient care. Each patient user account security is fortified by the collective strength of the blockchain network, making the entire system resilient to unauthorized access. Every transaction is recorded on an immutable ledger, and can be verified by multiple stewards, without compromising the identity of each patient user account owner, which is anonymized. In this scenario, physicians, healthcare institutions, and patients all benefit.

The present approach differs from cloud solutions, which have failed to gain market traction as over 85% of medical institutions still rely on physical mediums of data exchange as these solutions suffer from security vulnerabilities, slow processing speeds, system downtimes, and high implementation costs due to their architecture. Unlike the decentralized nature of the present system (where each patient user account represents an individual's ownership of their data), in the cloud, the patient user account itself is owned by a single entity. Sharing medical data becomes cumbersome, as every user seeking access must first seek approval from the single entity, hindering interoperability. Attempting to share medical data with a user that the single entity does not approve leads to denial. Gaining access to the patient data is prohibitively costly, and every user seeking access must surrender ownership of their patient user account to the single entity, a process that compromises autonomy. Maintenance and security measures for the patient user account are centralized and costly, in stark contrast to the autonomous and cost-effective approach enabled by auto-executing smart contracts of the present system. Critical issues arise in the absence of an automatic record of transactions, and the single entity possesses comprehensive knowledge of all identities, sparking concerns regarding privacy and data misuse. This single entity can be attacked from a security standpoint, and hence requires tight controls from a middleman. Most critically, if the single entity is compromised, then all patient user accounts and data become vulnerable, underscoring the fragility of this centralized system.

Beyond the focus of the examples in this disclosure on healthcare for managing medical imaging data, this framework offers a generalizable solution for any record storage and sharing system. The architecture can be readily adapted to protect various types of data across diverse industries. It empowers users with data ownership and facilitates secure, transparent data access across various domains.

Accordingly, this architecture provides several advantages, including but not limited to:

Enhanced Scalability and Cost-Effectiveness: By leveraging off-chain data storage with blockchain-based hashing or integrating decentralized storage solutions like IPFS, the system avoids storing large amounts of data directly on the blockchain. This significantly reduces transaction costs and improves processing speeds compared to traditional on-chain storage methods. This makes the system more scalable and cost-effective for wider adoption within the healthcare industry.

Improved Interoperability: Unlike private blockchains with limited access, this approach can potentially foster better interoperability within the healthcare ecosystem. By utilizing mechanisms like public blockchains for specific data elements or integrating with existing healthcare data standards, the system can facilitate smoother data exchange between different healthcare providers and institutions. This improved interoperability can enhance collaboration and improve patient care coordination.

Increased User Privacy: The architecture promotes user privacy by allowing patients to prove they possess certain medical credentials without revealing the actual data itself or their identity. This "zero-knowledge proof" approach protects sensitive medical information while still enabling authorized access for legitimate purposes. For instance, a patient could prove they have received a specific vaccination without revealing their entire medical history.

Reduced Reliance on Private Chains: The proposed architecture moves away from the high costs associated with creating and maintaining private blockchains. This makes the system more accessible to smaller healthcare providers or organizations that might not have the resources to invest in a private network infrastructure. Thus, the system is built in a chain-agnostic manner such that institutions that prefer to use a private network, can still do so.

Decentralized Access Control and Enhanced Security: The present architecture strengthens security by decentralizing access controls. Unlike centralized systems with a single point of failure, data access is controlled through individual user wallets and private keys. Even if a hacker were to gain access to the cloud storage where the data resides, they would be unable to decrypt or steal the information. Each patient's private key would be needed to unlock their data, each key which is a 256 character long binary code that is programmatically derived--making it near-impossible feat for large-scale data breaches. This decentralized approach significantly reduces the attack surface and enhances the overall security of the system.

Another key differentiator of the present system lies in its approach to consent management. The system utilizes multi-signature (multi-sig) methods through a smart contract to automate the process, addressing a significant technical challenge in healthcare data sharing.

Traditional Consent Management: Current healthcare data sharing often relies on manual processes like obtaining physical HIPAA release forms signed by patients. This approach is Time-consuming and Inefficient: Manual consent gathering can delay access to critical medical information, hindering timely care decisions. It is also Prone to Errors: Paper-based forms are susceptible to errors and inconsistencies, potentially leading to data access issues or privacy violations. And it has Limited Audit Trails: Manual methods often lack robust audit trails, making it difficult to track and verify consent history for data access requests.

In contrast, the Multi-Sig Advantage of the present system leverages multi-sig technology to automate consent management, offering several advantages:

Automated and Streamlined: The system can automatically enforce pre-defined consent parameters, ensuring data is only released or transmitted after approval from all authorized parties. This significantly reduces processing time and streamlines data sharing.

Enhanced Security and Traceability: Multi-sig transactions require digital signatures from all relevant parties, creating an immutable and tamper-proof audit trail. This ensures clear and verifiable consent records, simplifying compliance with regulations like HIPAA.

Reduced Reliance on Manual Processes: Eliminating the need for paper forms reduces administrative burden on healthcare providers and streamlines the entire data sharing process.

By automating consent management with multi-sig technology, this system offers a unique and technically superior solution compared to traditional methods. It promotes secure, efficient, and auditable data sharing while ensuring patient control over their medical information.

BRIEF DESCRIPTION OF THE DRAWINGS

The included drawings are for illustrative purposes and serve only to provide examples of possible structures and operations for the disclosed inventive systems, apparatus, methods and computer program products for database system digital asset creation and transfer. These drawings in no way limit any changes in form and detail that may be made by one skilled in the art without departing from the spirit and scope of the disclosed implementations.

FIG. 1 illustrates an overall architecture diagram and components interaction.

FIG. 1A illustrates adding a provider of medical data/images as a trusted entity.

FIGS. 2A, 2B illustrate the provider user flows (which can be generalized to any institution).

FIG. 3 illustrates the patient user flows (which can be generalized to any patient).

FIG. 4 illustrates the system components interaction.

FIG. 5 illustrates a sample implementation for a provider user journeys.

FIG. 6A illustrates a sample implementation for the patient user journey of sharing medical images with other users.

FIG. 6B illustrates a sample implementation for the patient user journey of revoking access.

FIG. 7 illustrates a sample implementation for viewing owned medical images.

FIG. 7A illustrates a sample implementation for viewing medical images shared with a user.

FIG. 8 illustrates a sample implementation for consent flows.

FIG. 8A illustrates a sample implementation for recording consent on blockchain.

FIG. 8B illustrates a sample implementation for querying the consent status on blockchain.

FIG. 9 illustrates minting a token method using a smart contract.

FIG. 10 illustrates granting the view role to a token by the owner of the token.

FIG. 11 illustrates revoking the view role to a token by the owner of the token.

FIG. 12 illustrates querying for a list of tokens that belongs to a smart contract.

FIG. 13 illustrates the implementation of the gasless transaction with a sample user flow.

FIG. 13A illustrates the implementation of the gasless transaction.

FIG. 14 illustrates a sample implementation of the Multi-Factor-Authentication (MFA).

FIG. 15 illustrates the system diagram for architectural components.

FIG. 16 illustrates a sample implementation for wallet setup.

FIG. 17 illustrates a sample implementation for wallet authentication.

FIG. 17A illustrates a sample implementation for wallet authentication.

FIG. 18 illustrates a sample implementation for wallet gating.

FIG. 19 illustrates a sample implementation for zero-knowledge proofs.

FIG. 19A illustrates a sample implementation for zero-knowledge proofs.

FIG. 20A illustrates a sample implementation for multi signatures within a single transaction.

FIG. 20B illustrates a sample implementation for multi signatures within multiple transactions.

FIG. 21 Includes a novel interface that illustrates how medical studies are requested.

FIG. 22 Includes a novel interface that illustrates one way how the requests are fulfilled.

FIG. 23 Includes a novel interface that illustrates the history of transactions.

FIG. 24 Includes a novel interface that illustrates the viewing of medical image studies.

Figure 25:
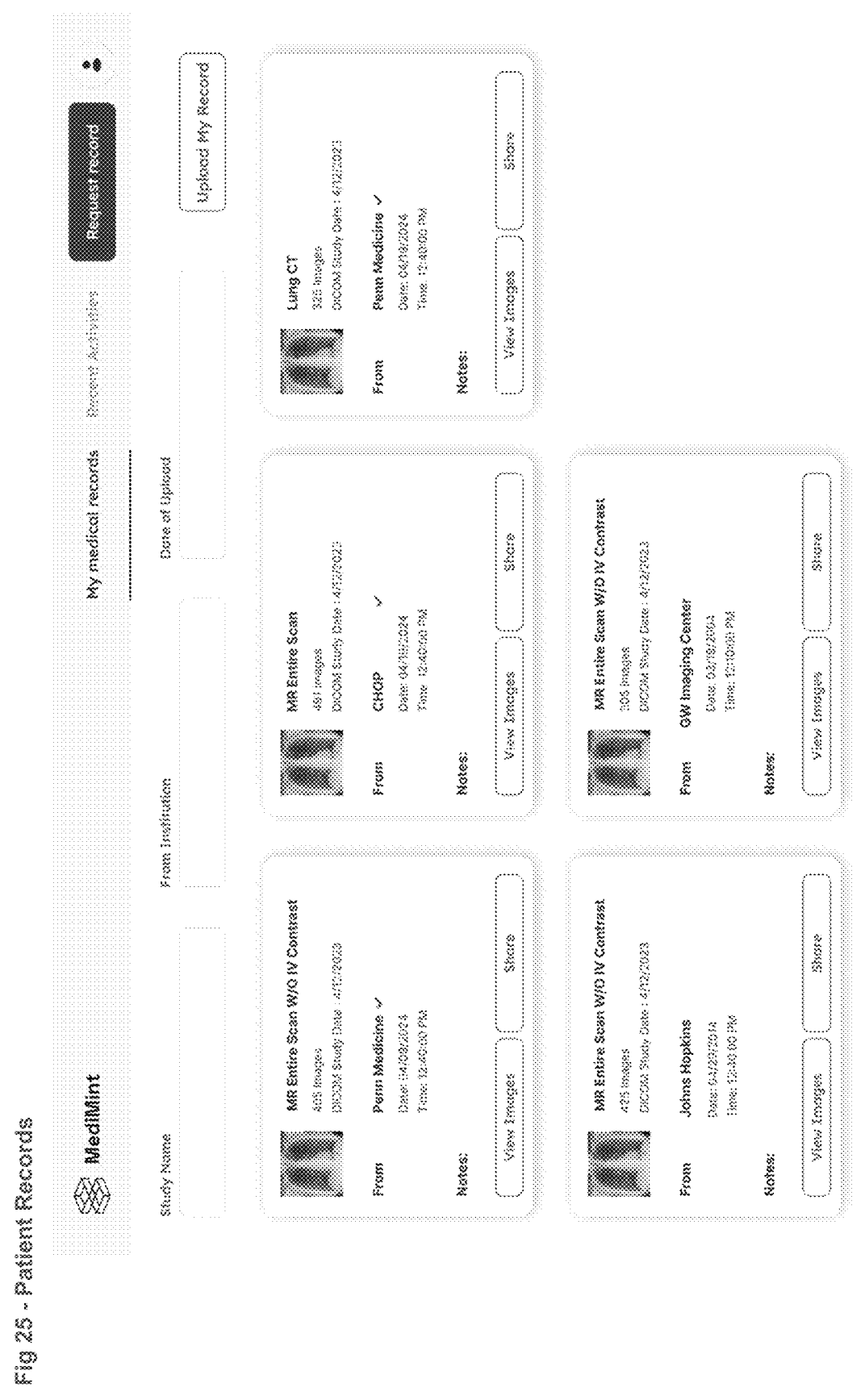

FIG. 25 Includes a novel interface that illustrates the dashboard of patient records.

FIG. 26 illustrates a sample implementation for verifying 'view' access on the blockchain.

FIG. 27 illustrates a sample implementation for sharing shared medical images.

FIG. 28 illustrates a sample implementation for viewing history of transactions.

FIG. 29 illustrates a sample representation of a non-fungible token generated from the system.

DETAILED DESCRIPTION

In describing the illustrative, non-limiting preferred embodiments of the disclosure illustrated in the drawings, specific terminology will be resorted to for the sake of clarity. However, the disclosure is not intended to be limited to the specific terms so selected, and it is to be understood that each specific term includes all technical equivalents that operate in similar manner to accomplish a similar purpose. Several embodiments of the disclosure are described for illustrative purposes, it being understood that the system may be embodied in other forms not specifically shown in the drawings.

A. Overview

The overall architecture diagram of the system (5) is shown in FIGS. 1, 15. As depicted, the system (5) is represented by the user layer (240), application layer (260), and blockchain layer (280). The system (5) includes a user who accesses a user device, interacts with a user interface layer (240) to create or read data. As shown in FIG. 15, the user layer (240), the application layer (260), and the blockchain layer (280) can be implemented, for example, by one or more processing devices such as a computer or smart phone. Each layer (240), (260), (280) can have its own one or more processing devices, or the layers (240), (260), (280) can share integrated one or more processing devices. This user can be a provider user who uploads data to the system, a patient user who owns data on the system with rights to manage and revoke access to the data, and both users can view and share images on the system.

The application layer (260) intakes user email addresses to generate cryptographic wallets. The application layer (260) also intakes DICOM images that are securely uploaded (310) and validated (340) to: (i) extract metadata from the raw image files; (ii) securely store the metadata in a decentralized storage module and encrypt the metadata with the public key of the patient user, who is the study owner; (iii) securely store the images in a cloud storage module and encrypt the images with the public key of the patient user, who is the study owner; and (iv) create a digital record of the imaging study by minting a Non Fungible token on the blockchain layer (280) that contains a URI to the metadata on the decentralized module, which contains a URI to the images on the cloud.

The user layer (240) represents the interface through which medical professionals (e.g., healthcare provider users), patients, and other stakeholders interact with the system. This includes the ability of medical imaging providers to utilize a user interface (such as web portals, mobile applications, and desktop clients) to manage medical imaging records, for example to release medical imaging records, request medical imaging records, view the transaction history (sharing and request history) for specific patients' records, and view or download a patient's medical image studies (FIG. 2A). A user is also able to, depending on their access permissions, view, download, share, and/or revoke access to their medical imaging studies (FIG. 3). As used here, the term study can be, for example, a collection of one or more medical images, and a patient can have studies ranging from 1-5000 images depending on modality.

The user layer (240) serves as the entry point for the implementation of medical provider workflows (FIG. 5) and user/non-provider workflows (FIGS. 6A, 6B). It facilitates tasks such as accessing medical images (FIG. 7), securely downloading medical images (FIG. 7A), managing consent (FIG. 8), sharing medical image studies (FIG. 10), revoking access to medical image studies (FIG. 11), and managing authorizations (FIG. 14).

The application layer (260) serves as the backbone of the system (5), encompassing various modules and services responsible for login/authentication (300), uploading medical image studies (310), encryption and decryption (320), storage and retrieval of data (330), registration of trusted issuers (340), wallet modules (350), IPFS (Inter Planetary File System) which is a distributed ledger module for data storage and retrieval (360), blockchain listener modules (370), managing non-fungible tokens (NFTs) (380), and a dedicated relayer module (390).

The trusted issuer registration module (340) enables administrators of the system to designate medical providers as trusted issuers (FIG. 1A). First, a healthcare provider user will register into the system through their credentials like their NPI and generate a healthcare provider user account via the Login ad Authentication module (300). Subsequently, a hierarchical deterministic cryptographic wallet will be created for that healthcare provider user account, and the wallet address will be appended to a trusted issuer whitelist stored on the smart contract through the Truster Issuer Registration module (340). This designation grants specific permissions to the hierarchical deterministic cryptographic wallet addresses associated with trusted issuers. These permissions include the ability to (1) release medical image studies to patients and (2) to request medical image studies from other providers or institutions on behalf of patients.

Healthcare providers serve as trusted authorities for uploading medical imaging studies to the system and distributing them to the correct patient user owner. In the backend, the upload module (310) is able to process the uploaded study from a healthcare provider user, and subsequently trigger the smart contract (420) to create a non-fungible token, which is a digital representation of the study on the distributed ledger, and assign it to the patient user's cryptographic wallet-a process known as minting (FIG. 1A). A smart contract, which is essentially a self-executing digital agreement stored on a blockchain network, is executed to validate transactions for adding a trusted healthcare provider user, which must be initiated by the administrative wallet of the system, or a super user of the system (10). The smart contract then whitelists the provider user's wallet address, granting them approval to upload medical data for patients

(20) and request medical images on behalf of patients from other providers. All transactions initiated by the healthcare provider user, who is also a trusted issuer, are verified and executed by the smart contract (420) securely recorded on the blockchain ledger (430) for transparency and accountability (30). A first smart contract can be provided to verify patient users and a second smart contract can be provided to verify healthcare provider users, or a single smart contract can verify both patient users and healthcare provider users.

The login/authentication module (300) encompasses a multi-factor authentication implementation (FIG. 14). The authentication module authenticates the user into their digital wallet, allowing users to securely access their accounts using cryptographic keys and zero-knowledge proofs (FIGS. 19, 19A), which allows users to prove possession of credentials without revealing actual data or their identity itself. In particular, the system (5) prioritizes user security and control through a decentralized access system. Public/private wallet key pairs are generated deterministically using a master private key derived from a randomly generated seed phrase, known as the master seed phrase (350). This master seed phrase is then secured within a dedicated system vault such as the HashiCorp Vault, ensuring its isolation and protection. The HashiCorp Vault enforces strict access controls for master seed phrases by authenticating identities against trusted sources and cloud platform authentication modules. The system-managed wallet key pairs are derived as child keys programmatically from the secured master private key to enhance security within the blockchain-based system.

This disclosure is not limited to the use of Hierarchical Deterministic (HD) wallets for key generation. Other cryptographic protocols, such as Multi-Party Computation (MPC), can also be employed to achieve a distributed key generation (DKG) process. In an MPC protocol like Shamir's Secret Sharing (SSS) or its variants (e.g., LIT protocol), a group of nodes collaboratively generate a key pair where no single node possesses the entire private key. Instead, each node holds a secret key share. These key shares can then be used for signing and decrypting data. Importantly, cryptographic operations like signing or decryption are performed in parallel by the nodes, and the individual results are aggregated to form the final output (signature or decryption key) without ever revealing the underlying private key itself. This distributed approach significantly enhances the security of the key management system. The term "authentication method" refers to the specific credential used to control access to the underlying key pair. This credential can be a programmatically linked identifier, such as a wallet address, a social login like Google OAuth, or even a Discord account. The choice of authentication method depends on the specific application and desired security posture.

The system leverages a zero-knowledge proof scheme, such as Schnorr signatures, to allow users to prove possession of specific credentials (e.g., age verification) without revealing the underlying data itself. This cryptographic technique enables users to generate a mathematical proof that demonstrates knowledge of a secret value (like a private key) without disclosing the value itself. The system verifies this proof using a corresponding public key, ensuring user authentication without compromising data privacy.

The system derives a specific child key pair using the hierarchical deterministic framework, dedicated to generating zero-knowledge proofs for user credentials. This derived key pair functions similarly to the standard key pair generation process described earlier (350). Specific user credentials, such as age verification, are translated into a mathematical representation suitable for zero-knowledge proofs. This representation could involve hashing the credential data. The user, in possession of the private key, utilizes a Schnorr signature scheme to generate a zero-knowledge proof.

This proof mathematically demonstrates that the user knows the credential (represented mathematically) without revealing the actual credential data. The proof generation leverages the relationship between the private key and the public key (350). The generated zero-knowledge proof, along with the user's public key, is submitted to the system for verification.

The system utilizes the user's public key and the Schnorr signature verification algorithm to validate the proof. This verification process confirms if the proof was generated using the corresponding private key, without revealing the credential data itself.

The upload module (310) facilitates secure creation and sharing of medical image studies through direct integration into Picture Archival and Communication Systems (PACS) for interoperability with existing medical infrastructure or a user-friendly file upload front-end UI for straightforward manual uploads (FIGS. 2B, 7). Alternatively the DICOM files can be directly transferred or pulled from a VNA or PACS through secure transfer protocols. The upload module facilitates the collection of medical images on the cloud, serving as the initial step in the data processing pipeline (FIG. 5).

Medical imaging data, such as X-rays, CT scans, and MRIs, are typically stored in a standardized format called Digital Imaging and Communications in Medicine (DICOM). This format ensures compatibility and interoperability across different medical imaging devices and software systems. A DICOM file encapsulates two key components:

Medical Image: This is the core visual data representing the patient's anatomy or internal structures.

Metadata: This associated data provides contextual information about the image, such as patient demographics (name, ID), date of acquisition, modality (X-ray, CT scan, etc.), and other relevant details for accurate interpretation.

The initial processing step within this system (5) involves parsing and decoding the uploaded DICOM file. This process separates the encapsulated medical image data from the associated metadata. That is, the system essentially "unpacks" the DICOM file, extracting the visual image and its corresponding information label. This separation allows for independent processing and utilization of both the image data and the metadata within the system's functionalities.

The storage/retrieval module (330) encrypts the images in the study using public key of the patient user, who is the owner of the study, and stores the 'medical images' on a cloud system and encrypts the associated 'metadata' with the patient user's public key and stores the metadata in a decentralized storage system like IPFS (FIG. 9, 111). The upload (310) and storage/retrieval (330) modules work together to also upload and store the metadata of the study (which contains a reference to the 'medical image study' on the cloud system) on IPFS (inter planetary file system or an off-chain decentralized storage) (FIG. 9) through the IPFS/Distributed Storage Module (360). These data storage modules also facilitate retrieval and decryption of the appropriate medical image study from the cloud server when users view or download medical image studies (FIGS. 7, 7A).

The wallet module (350) links the application layer (260) and the blockchain layer (280), enabling the creation and management of cryptographic wallets specific to individual users (as these wallets contain public and private keys specific to the user). Before a patient user registers with the system, as soon as the file is validated and uploaded to the system, a patient user wallet is created for the patient's indicated email. A secure cryptographic wallet is generated for that patient user using a hierarchical-deterministic (HD) approach. This HD wallet is derived from a master key stored in a secure vault, ensuring a vast pool of unique child keys, including a public and private key for the user. The HD wallet has a cryptographic address to be located on the blockchain, a public key, and a private key. The generated cryptographic wallet is then linked to the patient user account using their email address. Later on, when the patient user accesses their studies, the patient user will register for an account through a dedicated user interface, providing their credentials (such as email and password). This information establishes a patient user account. The system generates and leverages cryptographic wallets with public and private keys for user authentication on blockchains, and uses them to encrypt patient health data with the patient's public key using a hierarchical-deterministic derivation approach and account abstraction. Furthermore, the system (5) leverages wallets for a novel approach to consent management. Patients can use their wallets to digitally sign consent for data release and access, creating an immutable and auditable trail within the system. This streamlines the consent process, eliminates reliance on paper forms, and simplifies compliance with regulations like HIPAA and others that require verifiable consent for data sharing.

This functionality extends to various interactions within the system, including implementation where a medical imaging provider shares medical images with a patient, initiating the minting of a non-fungible token (NFT) to the patient's wallet for the specific study (FIG. 9). The wallet module (350) facilitates handling of medical image studies among different users (FIG. 10), as well as the revocation of access for specific users (FIG. 11), and retrieval of non-fungible tokens categorized as 'owned' and/or 'shared' by a particular user (FIG. 12). The wallet module oversees processes such as wallet setup (FIG. 16), authentication (FIGS. 17, 25), wallet gating (FIG. 18), and implementation of zero-knowledge proofs (FIGS. 19, 19A). The wallet module also facilitates patient consent, as it enables patients to provide authorization and consent for their records to be released by signing a transaction with the wallet, before creating an NFT for the medical study by a trusted provider through multi-party signing (FIG. 20A, 20B). The wallet module also enables gasless transactions (FIG. 13), ensuring that users can interact with the platform without incurring gas fees with each transaction.

The listener module (370) works closely with the blockchain layer in order to facilitate the logging/syncing of blockchain data when healthcare providers interact with the platform (FIG. 5), patient users interact with the platform (FIG. 6), and when any users access and/or download medical images (FIG. 9), and when patient users, when they are the study owners, provide consent (FIG. 8).

Similarly, the 'manage NFT module' (380) also works closely with the blockchain layer to ensure that all actions involving NFT tokens, such as creation (FIG. 9), sharing (FIG. 10), and revoking (FIG. 11) are appropriately handled.

The relayer module (390) acts as an intermediary or facilitator for transactions and interactions between users and the blockchain network. It is involved in all implementations for user journeys (FIGS. 7, 8, 9, 10) as well as all interactions with the blockchain (FIGS. 11, 12, 13, 14, 16, 20A, 20B).

The blockchain layer (280) leverages distributed ledger technology to handle all transactions involving the blockchain. The blockchain layer (280) includes a cryptography module (27), consensus module (410), smart contract module (420), and ledger module (430).

The cryptography module (27) and the consensus module (410) (FIG. 15) are utilized to secure transactions and to achieve agreement among network participants regarding the validity and chronology of transactions.

Smart contract modules (420) are employed when adding trusted issuers (FIG. 1A), creating NFT tokens for medical image studies (FIG. 9), sharing tokens with other users (FIG. 10), revoking access to NFT tokens (FIG. 11), querying a list of tokens that belongs to a wallet address (FIG. 12), facilitating gasless transactions (FIGS. 16, 16A), implementing wallet gating (FIG. 18), and enabling multi-signature transactions for automated patient consent (FIGS. 20A, 20B). Similarly, the ledger (430) modules within the blockchain layer are responsible for managing and maintaining the distributed ledger, which serves as the immutable record of all transactions occurring within the blockchain network. This includes all previously mentioned actions for the smart contract module.

The component interactions between each client is further described below with respect to FIG. 4.

The blockchain layer (280) and application layer (260), though working together, serve distinct purposes with technical differences. The blockchain layer (280) acts as a secure and tamper-proof vault for data. It utilizes cryptography and a consensus mechanism to ensure data integrity and agreement among participants. This layer also executes smart contracts, self-enforcing programs that automate tasks. Data on the blockchain layer (280) is distributed across a network of computers, making it highly resistant to modification. In contrast, the application layer (260) provides user interfaces and functionalities for interacting with the blockchain. It translates user requests into transactions and manages user wallets. This layer also handles encryption, decryption, user authentication, and authorization. Data management in the application layer is flexible and depends on the specific application.

This separation offers several benefits. The blockchain layer's security strengthens the overall system, even if the application layer faces challenges. Additionally, the application layer can be scaled independently to accommodate more users without impacting the core blockchain. This separation also promotes innovation by allowing diverse applications to be built on the same blockchain foundation. Finally, the core functionality remains decentralized, fostering trust and transparency in the system. In conclusion, this layered approach creates a secure, scalable, and flexible system for various applications.

B. Medical Provider Workflows

Referring to FIG. 2A, medical providers, authorized as trusted issuers (FIG. 1A), are able to release medical images 2001, request medical images 2011 from a third-party provider, view the history 2021 of released and requested records, and view patient medical images 2031 using the system. When the provider chooses the release option (2001), the medical provider enters the pertinent patient details (including patient email, DOB, etc.) and clicks on upload to find the medical image files, in Digital Imaging and Communications in Medicine (DICOM) format, and other related records to be released to the patient, or the relevant medical image files can be found in the Picture Archiving and Communications Systems (PACS) integrated with the system (2002). They can also drag and drop the files from their local storage to the medical image uploader (2002). Once the files are uploaded in the user interface layer, the application layer of the system extracts metadata from the files (250) during the upload module (310) and stores the metadata on IPFS, while the medical data in the cloud, and encrypts the data with the patient's public key (250).

The system uniquely follows a novel verification and validation step before any data is produced on chain. It not only verifies that the provider user who uploaded the data is a trusted issuer with a whitelisted wallet address on the smart contract (380) but the system also validates that the correct data is being sent to the correct patient through a novel validation mechanism in the upload process (310). Finally, the system is able to compare the hash of the file at various points in time to ensure it is not corrupted or tampered with.

This novel validation system of comparing the patient details with the extracted DICOM metadata ensures compliance with privacy regulations and guarantees the correct data reaches the correct end user, since in traditional workflows, many times healthcare providers are prone to human error and mistakenly provide the wrong patient's data to the wrong recipient, which leads to errors in medical treatment and diagnosis. This novel validation system also flags errors at the source of imaging in case the imaging was performed on the incorrect patient. Once the system compares the patient data against the extracted data for patient name and date of birth (250), the system showcases the errors in the UI of the user layer (240), and the medical provider has the ability to fix validation issues, such as patient name mismatch, study ID mismatch, DOB mismatch, and wrong file formats (2003). The provider then releases the medical image study (2004) to the patient through the file upload interface. Alternatively, a secured file transfer can be initiated directly from PACS or the imaging source in a manual or automated manner (through direct file transfer protocols).

When the medical provider wants to request the release of records from a third-party provider (2011), they enter the third-party provider and the patient details (2012). The software generates a temporary access code and a URL (2013), which can be shared with the third-party provider (2014). The third-party provider is able to use the URL and the temporary code to upload the patient's relevant medical image files (310). A sample interface for initiating a request for medical data from a provider is included in FIG. 21. The novelty of this 'request for records' interface lies in the ability to electronically collect patient user consent for the release of medical records within the flow of the request, which is then logged in an immutable distributed ledger audit trail (430), verified by the smart contract (420), and passed to the healthcare provider who will fulfill the request in a HIPAA compliant manner by ensuring that the patient has consented to the release of records (420), before releasing the images to the patient user. A sample interface for fulfilling the request through a URL and temporary code is included in FIG. 22. This novel interface provides a simple and intuitive UI for any healthcare provider or patient to upload their medical studies through a secure link with an expiration time.

The provider can also use their credentials to login to the system and choose "History" to view the release and request history (2021). They are able to filter the history, such as by using the patient's DOB, to look for specific records (2022). The medical provider is able to view the status of each record and has an option to click on 'View Studies' to view or download the medical image study (2023). A sample interface for viewing the history of transactions is included in FIG. 23. This is a novel interface as this is the first time complete, fool proof transparency is provided to a healthcare provider user and patient about the history of transactions with a live status of the data sharing transaction so that every party has visibility into the status of the transaction. A sample interface for viewing the studies and downloading the studies is included in FIG. 24. This novel interface provides a patient and provider-friendly experience of viewing, downloading, and sharing the images in the application with the ability to adjust contrast, scroll through frames, zoom, and add measurements while viewing the study.

The system offers a novel approach to accessing and visualizing medical records. Unlike traditional systems where users download entire encrypted files, the system allows for programmatic decryption using the patient's private key. This ensures that only authorized users can access the data while maintaining its confidentiality in transit and at rest. Furthermore, the system provides flexibility in viewing options. Downloaded records can be viewed using a general-purpose viewer or DICOM viewer for exploration. Alternatively, for medical professionals like radiologists, a specialized diagnostic viewer can be integrated, enabling them to analyze the records with advanced tools and functionalities. This tailored approach empowers patients with control over their data while catering to the specific needs of healthcare professionals.

The medical provider logs into the System and chooses "Patient Records" to view the released and requested patient records (380, 2031). The medical provider can view a list of patients to view all their studies (2032) and choose a study to view or download (2033). A sample interface for viewing all patient studies is in FIG. 25 along with the view of a specific record (FIG. 24).

C. Patient Workflows

Patient users are empowered to access their medical images through the system platform (5). By utilizing their cryptographic digital wallet and leveraging the power of zero-knowledge proofs, patients can securely validate their identity and authenticate into their wallet, ensuring seamless and privacy-preserving access to their medical imaging data. Wallet gating is employed and refers to a system where access or permissions are granted based on ownership or control of a specific digital wallet. Zero-knowledge proofs are used to demonstrate that the user has the required ownership of the wallet and data without disclosing any specific details about the wallet's contents or transaction history. In essence, zero-knowledge proofs enable secure and privacy-preserving authentication in scenarios where trust is required but revealing personal information is undesirable.

When a patient user, is authenticated into the system (5) by the Login and Authentication Module (300) (FIG. 1), the user can connect to their digital wallet (310), FIG. 3. Their digital wallet contains non-fungible tokens that are owned by the patient user wallet, and the list of tokens in the wallet is abstracted and represented in a user-friendly interface through a dashboard of medical study records (FIG. 25). Within their user account, patient users can see representations of NFTs, which are the digital medical image study records, minted by trusted issuers/medical providers, signifying the ownership of these digital medical image studies by the patient user (330). Further, the patient can also view NFTs that other users in the system have specifically shared with them, even if said patient is not the owner of the study. These NFTs contain a Uniform Resource Identifier (URI) to encrypted metadata stored on the decentralized storage (360) which in turn contains a URI to encrypted medical images on a secured cloud server (182). Patient users can view or download these medical image studies owned by them (330) and also share the studies by granting view access to other users (330). Another type of access called "view and share" allows certain non-patient users, such as specialists, ordering physicians, or family members, to view the patient's medical images as well as share the medical images with other users (350). Patient users can also authorize healthcare providers to perform actions, such as viewing or downloading their medical image data. Patient users can revoke access at any time to their owned medical images. The users who have received access to the patient user's images are able to view and download (depending on permissions) the medical images shared with them (340) by patient users.

D. User Flow Implementations Exclusive to Medical Providers:

Releasing Medical Records:

An automated process is triggered as soon as an image file is detected in the designated local computer file storage location (at 220) either through direct integration with Picture Archiving and Communication Systems (PACs) or after a manual upload of the files through a simple drag & drop UI interface by trusted issuers (220) (FIG. 2B). Once the upload of images is performed, the system (250) extracts from the DICOM header pertinent fields to generate patient metadata, such as the patient's name, DOB, medical record number, social security number, institution name, and provider name. Then, the email address of the recipients of the data are manually entered. These recipients include the patient, along with the provider, ordering physician, or any specialists. When recipient email(s) are provided, a hierarchical-deterministic cryptographic wallet for each recipient is subsequently generated through a hierarchical-deterministic wallet generation algorithm, only if no prior wallets have been previously created for these recipients.

This hierarchical deterministic algorithm for wallet generation (350) starts with randomly generating a master seed phrase. From this seed phrase, a master public key and private key are derived. This master public key and private key pair acts as a parent key that can produce child and grandchildren keys, ultimately providing an infinite supply of wallets. This eliminates the need to store the private and public keys in a centralized system as the keys are derived programmatically in real time. This algorithm is employed when generating new cryptographic wallets for patient and provider users upon registration (350).

Once the images are released, or sent, to the recipient, the raw DICOM file is processed into 'medical image files' (containing the medical images) and 'metadata' (containing information from the DICOM header). The raw DICOM file, 'medical images', and 'metadata' are encrypted with the patient's hierarchical-deterministic cryptographic wallet public key, and stored securely (250) on a cloud storage. The software stores the encrypted non-PHI metadata and a URI to the encrypted medical images and raw DICOM located on the secure cloud storage on a decentralized storage system (Interplanetary File System). The metadata may include details such as the study location, hash values of the DICOM files, and other pertinent study-related information. The DICOM file hashes serve to safeguard against tampering.

A smart contract ERC721 method for minting tokens verifies if the release of the records is from a trusted issuer, who would only be a verified and licensed healthcare provider, and if so, mints a digital token (Non Fungible Token (NFT)) to the patient's hierarchical-deterministic cryptographic wallet address, designating the patient as the owner of the asset (260). NFTs are minted to the patient's wallet, with the token URI pointing to encrypted metadata stored in the decentralized storage system (IPFS). The NFT is transferred to the patient's cryptographic digital wallet, providing the patient access to their off-chain medical image data. Wallet gated access requires authentication through cryptographic signing and zero-knowledge proofs (ZKPs) (270). Access to view the NFT is granted to both the provider and the physicians associated with the provider (280). The patient is notified via email or text.

The system addresses a critical challenge in healthcare data security: ensuring the authenticity and integrity of medical images (DICOM files) after potential cyberattacks. Traditional healthcare systems often lack robust mechanisms to verify if ransomed data has been tampered with. The system addresses this gap by employing checksums, a cryptographic technique that generates a unique fingerprint for each DICOM file.

Pre-attack Checksums: During upload, the system calculates a checksum for each DICOM file. This checksum is securely stored alongside the corresponding medical record.

Post-attack Verification: If a healthcare provider recovers data after a ransomware attack, they can utilize the system to recalculate the checksum for each recovered DICOM file. By comparing the newly generated checksums with the pre-attack versions stored in the system, healthcare providers can definitively determine if the recovered data has been manipulated or altered by attackers.

Thus, this functionality empowers healthcare providers to make informed decisions about the authenticity of ransomed data, potentially saving them from paying for tampered or useless information.

When a provider releases a medical image study to a patient, a secure and transparent record of a medical study is created on the blockchain. The use of a blockchain ensures that the data cannot be tampered with, and the assignment of roles restricts access to the study to authorized individuals. The steps involved in the minting of the token to the owner's wallet involves the following (FIG. 9). The off-chain metadata entries are uploaded in JSON format to the IPFS (111). A smart contract is executed to mint the token to the wallet address of the patient who owns the study (112).

This system (5) utilizes smart contracts (420) in a novel manner to manage the issuance and control of Non-Fungible Tokens (NFTs) within a healthcare ecosystem. Unlike traditional NFT applications, the present system ensures exclusive minting authority by trusted issuers, preventing unauthorized creation. Furthermore, the smart contract guarantees that patients retain sole ownership of their data. Consent is demonstrably obtained before releasing any study data to the patient, with the ability to share or revoke access at any time. The system also incorporates a multi-signature function for secure and verifiable consent collection, and automatically generates auditable token records for enhanced transparency. This unique combination of features empowers patients with complete control over their healthcare data while streamlining data management and transfer.

The smart contract mints a study token for the study owner's wallet address if the request is from a trusted issuer. Only a patient user can be a study owner, and only a healthcare provider user can be a trusted issuer. A token ID is then assigned to the token, and its URI references the metadata stored in IPFS (113). The smart contract assigns the role of 'owner' to the patient user who is the owner of the study by mapping their wallet address to an owner role (114). The wallet address of the trusted issuer, or healthcare provider user, is granted the role to view the study (114).

FIG. 9 shows the process of minting a token for a medical study. At step 110, the trusted issuer generates metadata entries in JSON format. Here, the trusted issuer is the party that uploads the medical data from their local PACS or file storage to the system and initiates the minting of the digital record (NFT) on the blockchain through the upload module (310). The user can be a verified healthcare institution, who serves as a trusted issuer, or a patient owner of their own data. Upon upload, the system creates metadata entries in JSON format that describe the specific medical data or imaging study, such as the study date, location, physician. At step 111, the system uploads the JSON formatted metadata file to the IPFS network. The IPFS (Inter Planetary File System) is the decentralized storage network that stores the JSON formatted metadata. The IPFS network assigns a unique Content Identifier (CID) to the uploaded data. This CID acts as a reference point for retrieving the data later.

At step 112, the system executes a smart contract function. The Smart Contract is a program stored on the blockchain that automates the minting process and assigns roles. The system initiates a transaction with the smart contract on the blockchain. This transaction includes the CID retrieved from step 111 and identifies the trusted issuer. The smart contract receives the transaction data and validates it. At step 113, the smart contract verifies if the request originates from a trusted issuer. If valid, the contract mints a new token for the study, and assigns a token ID. A URI (Uniform Resource Identifier) is created that references the location of the metadata in IPFS using the CID obtained in step 111. A new token is created on the blockchain and assigned to the patient user's wallet address. The URI referencing the metadata is stored within the token itself.

At step 114, the smart contract retrieves the wallet addresses for the patient user and the trusted issuer (the healthcare provider user) from the transaction data. The smart contract assigns roles to the wallet addresses, including an owner role to the patient user's wallet address, and a view role to the wallet address of the trusted issuer, which is a healthcare provider user. This allows both the patient user and healthcare provider user to view the study data.

Requesting Records from Third-Party Institutions on Behalf of Patients:

Trusted issuers/healthcare providers have authority to request records from third-party institutions on behalf of patient users (FIG. 5). In a sample implementation, the healthcare provider will login with their credentials (720), click on the request records menu (722) and populate relevant information (such as patient name, date, and other relevant request details). The backend module generates a temporary URL and a unique and secure access code that is valid for a specified duration. This URL is dynamically associated with both the trusted issuer, third-party provider, and the patient's data. The backend system ensures that the URL is uniquely generated for each specific study request, linking it to the relevant patient information and the requesting provider (724). After successful upload and release by the third-party institution using the URL and access code (726), the smart contract ERC721 method for minting tokens verifies if the transaction is requested from a trusted issuer by mapping to the original trusted issuer's wallet address that requested medical images (728). If so, the NFT is minted to the patient user's wallet (730) using the previously described mechanisms.

E. User Flow Implementations Exclusive to Patients Viewing Owned Medical Images:

Patient users are able to view the study NFTs that are owned by them in a user-friendly patient dashboard interface as depicted in (FIG. 25). In the sample implementation for viewing the images owned by patient users (FIG. 7), when the patient user is authenticated (910) into the system, the backend blockchain module lists the tokens owned by the user. The tokens contain an encrypted URI to the IPFS metadata (which contains a URI to the medical image study) (911).

To obtain a list of NFTs representing imaging studies (the tokens) for a wallet address, the client sends a request to a backend module to retrieve all non fungible tokens assigned to the wallet address as an owner or a viewer (FIG. 12). The backend then sends a request to query the smart contract responsible for minting and managing NFTs by calling specific functions in the smart contract that provide information about the NFTs minted for the given wallet address (141). Subsequently, the backend receives a response containing the list of NFTs owned by the specified wallet address (142).

The patient user views the list of owned tokens under the "Owned by Me" menu item (913). The user finds a medical study by name, and clicks on "View" for the required study to see a list of medical images within the medical study (914). The content of the NFT and IPFS URIs are fetched and decrypted by the patient owner's private key to get the study location and metadata (915). The patient is now able to see the medical images associated with the study (915). The user clicks on the listed images and can view the images that are part of the study through a user-friendly DICOM viewer (916).

User Layer (240): The patient user must interact with the system at the user layer in order to manage their tokens in the digital wallet. The patient dashboard interface (FIG. 25) is where the user interacts with the system to view their medical records (380). It displays a list of study NFTs owned by the user under the "My medical records" menu 913 (FIGS. 7, 25). Clicking on a specific study allows the user to view a list of images associated with it 914 (FIG. 24). Clicking on an image triggers the retrieval and decryption process (320).

Application Layer (260): Authentication module (910): This module verifies the user's login credentials before allowing access to the patient dashboard.

Backend blockchain module (280) (FIG. 7; 911, 915). This module handles interactions with the blockchain layer on the user's behalf. It performs the following actions:

Retrieves a list of tokens owned by the user's wallet address (911) by communicating with the wallet module and the relayer module (390) (FIGS. 11, 12, 13, 14, 16, 20A, 20B).

Decrypts the URI to the IPFS metadata using the user's private key (320) and (915) when authenticated into the system.

Retrieves the metadata and potentially the URI to the medical image study from IPFS using the storage and retrieval module (915).

Blockchain Layer: Smart Contract (141, 142) (FIG. 12): The backend module interacts with the smart contract responsible for managing NFTs (FIGS. 7, 11, 12, 13, 14, 20A, 20B). This smart contract has functions that allow retrieving information about NFTs minted for a specific wallet address (141). The response from the smart contract includes a list of relevant NFTs (142).

Sharing Owned Medical Images:

Patients are able to share the study NFTs that are owned by them (FIG. 6A). In the sample implementation for patients sharing images with other users (doctors/specialists/radiologists/family or others), the patient authenticates into the system (800). The backend blockchain module lists the tokens owned by the patient (801) using the previously described mechanism (FIG. 12). The patient views the dashboard of medical image study NFTs they own (802). A sample interface for this dashboard view is provided in (FIG. 25). This is a novel interface as it provides an aggregate view of data from virtually any healthcare provider from which the patient received imaging data, wherein the patient is able to share access to the data with additional recipients such as specialists, ordering physicians, and family members. The patient user clicks on the share button and enters the email, name, and description of the user they want to share with (803). The patient user can also indicate aliases for the email or the public key of the recipient based on the system design. The backend blockchain module creates a wallet for the user (using the user's email) if no prior wallet has been created for the corresponding email and shares the NFT with the user (804). Granting the view role requires a smart contract method to be executed on the blockchain to share the study token with another wallet (FIG. 10, 121). The smart contract verifies if the caller of the share function is the owner of the study token and assigns a viewer role to the requested wallet (122). A request is received from an owner wallet account to register the token for the shared wallet address as a viewer using a registry smart contract instance on the blockchain (123). An email notification is sent to the shared user for sign-up or sign-in (804).

More concretely, when a study owner wishes to grant "share" access to another user (viewer), the following steps occur:

Verification and Role Assignment: The smart contract first verifies if the function caller (initiating the share action) is the legitimate owner of the study token using the ownerOf (tokenId) function. If ownership is confirmed, the smart contract assigns a "viewer" role to the requested wallet address.

The owner's wallet initiates a request to a registry smart contract instance deployed on the blockchain. This request uses a smart contract method addRecordPermission (uint tokenId, address account) to map the study token (identified by tokenId) with the shared user's wallet address (account). Internally, the method utilizes a data structure called a mapping. A mapping acts like a dynamic associative array within the smart contract. It allows for associating a unique identifier (key) with a corresponding value. In this case, the key is a combination of the tokenId (identifying the study) and the user account wallet address (representing the shared user). The value associated with this key is set to true, indicating that the shared user has viewer access.

Code Snippet in Solidity
```
function addRecordPermission (uint tokenId, address
    account) external {
  require (ownerOf (tokenId)==msg.sender, "Not
      Owner");
  tokenShareMetadata [tokenId] [account]=true;
  emit RecordPermissionAdded (tokenId, account);
}
```
This code snippet demonstrates the addRecordPermission function. It performs the following actions:
  Verifies ownership of the tokenId using require statement.
  Updates the tokenShareMetadata mapping, setting the value for the key (tokenId, account) to true.
  Emits an event (RecordPermissionAdded) to record the access grant on the blockchain.
Email Notification: Following successful access mapping, the system triggers an email notification (804) to be sent to the shared user. This email typically includes instructions for signing up or signing in to access the study data with their designated viewer role. Other types of notification methods like SMS, push notification etc. can also be utilized.

Revoking Access to Owned Medical Images

Patients are able to revoke access to the study NFTs that are owned by them (FIG. 6B). In the sample implementation for patients revoking previously assigned shares with other users, the patient authenticates into the system (810). The backend blockchain module lists the tokens owned by the patient (811) using the previously described mechanism (FIG. 12). The patient views the dashboard of study NFTs they own (812). A novel user interface for this dashboard view is provided in (FIG. 25). The patient selects the user they have shared the image with and clicks "revoke" (813). The blockchain module removes the share of the study NFT with the user by changing the access permissions for the study NFT (814). Revoking the view role requires a smart contract method to be executed on the blockchain to revoke the study token that was previously shared with another wallet (FIG. 11, 131). The smart contract verifies if the caller of the revoke function is the owner of the study token, revokes the viewer role for the requested user account, which maps to a wallet (132), and maps the token role for the study token as revoked for that specific user account wallet address using a mapping that stores access permissions for each token (133).

Providing Consent for Release of Medical Images

In a sample implementation for automating patient consent (FIG. 8), the user authenticates into the system (1007). The NFTs owned by patients initially appear under "Pending Authorization" (1008). The patient clicks on the NFT of the study to provide consent for the provider to share their medical images with them (1009). An authorization form is displayed (1010), and the user has the option to agree or disagree to consent (1011). If the user agrees, the NFTs appear under the "Owned by me" section of the dashboard, while the ones yet to be agreed upon remain in "Pending Authorization", and the patient is unable to view the medical image studies represented by these NFTs. The consented information is also recorded as an immutable transaction in the blockchain (1012).

A patient, through the platform, is able to authorize and provide consent before the minting of an NFT for the patient's medical image study by a trusted provider using a multisig approach. Multisig, which is short for multi-signature, refers to a security feature for transactions. It adds an extra layer of protection by requiring one or more signatures to authorize a transaction on the blockchain. To initiate a transaction, a proposal is created within the wallet. Each person with a private key needs to sign the transaction with their key for it to be approved and executed. Using the multi-signature within a single transaction implementation (FIG. 20A), the provider creates a transaction with an operation id and signs the transaction (2801). Each transaction typically has only one sender or signer. The patient's signature is sent in the data field of a smart contract method (2802). To implement the multi-signature functionality in a contract, the 'ecrecover' assembly operation is used. This 'ecrecover' operation relies on a cryptographic technique called Elliptic Curve Digital Signature Algorithm (ECDSA) which mathematically links a message to a private key and creates a unique signature. Thus, the 'ecrecover' operation verifies the address associated with a signature in the transaction's data field. The multi-signature contract's code generates an operation ID based on factors, such as the destination, data, etc. The operation then verifies that this operation ID is signed by the signature(s) in the data field (2803). Within a single transaction, one signer is typically considered to be the sender of the message. Other signers' signatures are validated in the data field. The Patient's signature is sent as part of the data field and the signature is verified. If the signature is valid, ecrecover will attempt to recover the public key that was used to create the signature. An NFT for the study is minted after verification of both the provider's and patient's signature (2804).

Using the multi-signature within a multiple transaction implementation (FIG. 20B), the wallet contract is initially deployed on the blockchain. During deployment, the contract registers the addresses of users who are authorized to sign transactions. First, the multi-signature wallet contract is deployed, registering the 'signing addresses' provided by authorized users (2811). To mint an NFT representing medical data, a provider initiates a proposal by sending a transaction containing the NFT minting request to the contract (2810). This request includes details, such as the patient's medical image data and a unique operation ID derived from the NFT metadata.

Then, the patient, as the second user on the wallet contract, must confirm the operation ID by sending a separate confirmation transaction to the contract, providing their approval signature (2812). Both the proposal and confirmation transactions must be published on the chain before the resulting operation (NFT minting) (2814) can execute.

In the sample implementation for recording the consent on blockchain (FIG. 8A), the user triggers the giveConsent function on a smart contract (1001). The smart contact verifies if the caller is the owner of the token. If not the owner, an error message is returned and the function ends (1002). If the smart contract verifies the caller is the owner, the consent status of the token is marked as true (1003). In the sample implementation for getting the consent on blockchain (FIG. 8B), the user triggers the getConsentStatus function on a smart contract (1004). The token ID for which consent status is requested is provided (1005). The consent status is retrieved from the smart contract and returned status to the user (1006).

F. User Flow Implementations Available for all Users
Viewing and Downloading Shared Medical Image Studies:

All users are able to view medical images that are shared with their respective wallet addresses (FIG. 7A). When the user is first authenticated (900), the backend blockchain module lists the tokens that are shared with the user (901).

The blockchain module (FIG. 26) will get the user's wallet address from the authentication token used in the request (4200). The smart contract responsible for managing NTFs with view permissions will be queried to determine which tokens the wallet address has adequate 'View' permissions for (4220).

The user views the list of shared tokens under the "Shared With Me" menu item (902). The user can filter the studies associated with the patient using DOB, patient first and last name, and/or email (903). The user finds and clicks on "View" for the required study to see a list of images associated with the study (904).

To view the content of a medical image study, the URI contained on the NFT is used to access encrypted metadata stored on decentralized storage (IPFS). This metadata contains a URI to encrypted medical images on the cloud. The user's digital wallet utilizes the patient's private key to decrypt the metadata (4240), revealing the URI to the encrypted medical images. Subsequently, the private key is used again to decrypt the encrypted medical images, rendering the medical image information and images accessible for viewing. The user clicks on the listed images to view the images that are part of the study (905). Additionally, with the decrypted URI to the medical images, the digital wallet can allow downloading of the medical image files.

Sharing Shared Medical Image Studies Based on Permissions:

Any user in the system has the ability to share medical image studies that were shared with them if the patient user, who is the owner of the NFT representing the medical study, has granted said user special permissions to solely view, or view and share, the study NFT. In the sample implementation for users sharing images with other users (FIG. 27), the user authenticates into the system (7100). The backend blockchain module lists the tokens shared with the user (7101). The user clicks on the share button and enters the email, name, and description of the user they want to share with (7102). The backend blockchain module creates a wallet for the user if no prior wallet has been created for the corresponding email and shares the NFT with the user (7103). Granting the view role requires a smart contract method to be executed on the blockchain to share the study token with another wallet. The smart contract verifies if the caller of the share function has adequate permission to share the study token and assigns a viewer role to the requested wallet (7104). A request is received from an owner wallet account to register the shared wallet address as a viewer using a mapping on the smart contract with user account wallet addresses and their respective roles. An email notification is sent to the shared user for sign-up or sign-in (7105). A notification other than email, such as SMS, push, or other methods, can be utilized.

Viewing History:

Trusted issuers and any user of the platform is able to view the history of transaction, which may include release status, request status, share status, and revoke status (FIG. 28). Once a user authenticates into the system (28), they can click on the "history" menu to view the history of transactions (652). The listener module thread listens for events in the blockchain, such as NFT mint, share, and revoke status, and updates a database (654). The backend module queries the database and displays the history of release requests on study, patient details, uploaded date, NFT minted status (656). The requests from third party providers are uniquely marked and details on the third party are provided.

G. Wallet Set-Up and Authentication Protocols

As part of the system, robust hierarchical deterministic cryptographic wallet setup and authentication protocols are implemented in order to enhance security. Upon registration, where a user enters the login credentials to register with the system (241), the client requests are processed by the system to autonomously generate a hierarchical deterministic cryptographic wallet on the user's behalf (242). During the cryptographic wallet setup process (FIG. 16), each user is provided with a unique cryptographic wallet, comprising a public key and a private key. The private key is not stored by the system, and instead, securely derived, while the public key serves as their identifier on the blockchain.

Once the cryptographic wallet is assigned to a user, it transparently handles all associated processes without requiring user intervention. This wallet confers a unique cryptographic identity for the user within the system, thereby safeguarding the security and privacy of transactions. Notably, users are not directly engaged in interactions with the blockchain or the wallet itself. The user email address is associated with a cryptographic wallet address and an authorization token is sent (246). This is sent by the user for subsequent client requests regarding accessing the medical data. An NFT contract can be deployed (243) if the design requires one contract per NFT token.

When accessing the medical imaging data (FIG. 17), users need to authenticate themselves using their cryptographic wallet. This authentication process involves signing a challenge (253) or providing proof of ownership using their private key (254). The authentication flow can be part of user login (250), where the user sends the credentials (251) and subsequent verification by the backend system (252) followed by authenticating the wallet.

Upon initiating an action (256), users will receive a message via email or text prompting them to confirm the transaction (257). Once confirmed (258), the system manages the remainder of the process, ensuring the secure recording of the document transaction on the blockchain. This streamlines the process and enhances user-friendliness. Upon confirming the transaction, similar to entering the OTP (258), the system sends a transaction (259) to be signed using the user's private key (2590) and broadcasts the transaction to blockchain (2591). The transaction hash is returned to the system (2592). The signup process entails registering with an email, akin to conventional platforms. Subsequently, whenever users wish to share or receive a document, they will receive a message notification via email or text or using any MFA method. With a simple click to confirm the action, the system provides users with the benefits of blockchain security without the associated complexities.

If the wallet is managed by the user, the sample implementation (FIG. 17A) shows where the user enters the webapp (2501) and selects to login (2502). The webapp prompts for login with the wallet address (2503). The user selects the wallet type (2504) and connects with the wallet (2505). The webapp requests a challenge message to the backend system (2506). The backend sends a unique hash encrypted with the user's wallet address to the webapp (2507). The webapp forwards the hash to the user, which is decrypted, and a plain challenge is extracted (2508). The user signs the message with their private key (2509) and is forwarded to the backend through the webapp (2510). The backend verifies the signature using the wallet address (2511). If the signature is verified a JWT token is sent to the web app (2512) and if it fails, (2513) the authentication is rejected. Upon successful JWT (2514), the user's wallet is authenticated.

Once the user's wallet is verified, access permissions are granted based on their role and authorization level. This includes determining the specific medical imaging data they are allowed to access and any associated restrictions. By implementing wallet gating (FIG. 18), users can leverage their cryptographic wallets and associated private keys to authenticate themselves (261) and gain access to the tokens (262) that represent medical imaging data. This approach provides an additional layer of security and control, as users' access privileges (263) are tied directly to their individual wallets and the associated private keys.

Zero knowledge proofs (ZKPs) can be utilized to demonstrate that a user possesses the necessary credentials or entitlements without disclosing the actual medical images or sensitive patient information (FIG. 19). The verifier makes a custom request to verify the prover's personal data (271). The prover constructs a ZK proof (272) and sends the proof and response (273). The verifier applies ZK proof verification to ensure the response is correct (274). ZK proof is utilized when a wallet, assigned to a trusted issuer, signs a message indicating that a trusted issuer has conducted an imaging study (for example, an MRI). In this scenario, ZK proof allows other users to view the signed message and cryptographically verify that the action was indeed the imaging study (an MRI) performed by a hospital. This verification occurs without revealing any personal or sensitive information about either the hospital or the user.

In a sample implementation of ZKPs using HashiCorp Vault to store the master seed phrase (FIG. 19A), the user initiates the authentication and authorization (2701). The backend system validates the credentials (2702) and authenticates and authorizes the user. In the case that the 'User' wants to share a DICOM file with 'User2'. The User sends the share request to the backend (2703). The backend (2704) routes the request to decrypt the encrypted DICOM to the Web3 signer app. The signer app (2705) authenticates itself with the Hashicorp vault and derives the private key of the master the seed phrase (2706). The Web3 signer app derives the private key of the user and decrypts the data and sends it to the backend (2702). The backend retrieves the wallet address and encrypts the data (2708) and notifies the receiver module. The 'User2' initiates authentication and authorization with the backend module (2709) and the backend validates and authenticates (2710) the 'User2'. The 'User2' sends a request for the shared data (2711) to the backend. The backend requests the Web3 signer app to decrypt the data (2712). The Web3 signer app authenticates and authorizes itself with the Hashicorp vault (2713) and retrieves the private key of the master. The Web3 signer app derives 'User2's private key and decrypts the data and sends the decrypted data (2715) to the backend. The backend renders the decrypted data to 'User2' (2716).

Multi-factor-authentication (MFA) enhances security by requiring users to provide multiple forms of verification before granting access to an account or system (FIG. 14). In a sample implementation of MFA for login, the user inputs their username and password in the login form (1701). If the user's credentials are valid, an MFA passcode or PIN is sent to as an email/text/authentication app (1702). The user confirms the MFA which is a one-time passcode or PIN (1703). The user is able to login into the application (1704).

In a sample implementation for MFA before viewing or downloading the DICOM files, the user selects the action to view or download the DICOM (1711) and the application server uses the user's wallet to send a query to check the user's access control (1712). If the user has permissions on the blockchain to view or download the asset (1713), the MFA passcode or PIN is sent by either email/text/authentication app. The user confirms the MFA, which is a one-time passcode or PIN (1714), and the user is able to view or download the DICOM files (1715).

In a sample implementation for MFA before sharing an NFT, the application checks the action to share (1721). The Application server uses the user's wallet to send a transaction to give access to share with another user (1722). If the user is the owner on blockchain, the MFA passcode or PIN is sent to by email/text/authentication app (1723). The user confirms the MFA, which is a one-time passcode or PIN (1724), and the user is able to share (1725).

H. Gasless Transaction Implementation

In gasless transactions (FIG. 13), a spender, called relayer, pays for the transaction fee on behalf of the user. In the realm of blockchain technology, "gas" represents the computational cost required to execute transactions. Gasless transactions enable users to perform actions on the blockchain without paying transaction fees, simplifying the user experience. In a sample implementation, the backend module executes a smart contract method with the Spender wallet address on behalf of the owner wallet address using a permit function (161). This permit function has the spender's wallet address, token id, and split signatures of the owner's wallet address (161). The permit function verifies the transaction is for the owner by extracting the owner's address from the owner's wallet signatures (162). The permit functionality verifies the off-chain signature and executes the requested action, such as mint, share, and/or revoke (163). The function checks if the signer wallet address is defined in the Trusted Issuers smart contract (164). For revoke and share, the function checks if the signer wallet is the NFT owner (164). The smart contract updates the states and events in the blockchain (165).

The relayer wallet pays the gas fees on behalf of all the users (FIG. 13A). The transactions from different users (1601) are processed by the relayer module (1602), which executes a function on the smart contract that allows the relayer to execute transactions on behalf of the user. The function verifies the signature of the user's transaction to ensure that it is authenticated (1603). The user's transaction is executed, and the gas fees are paid using the relayer's account (1603).

I. Architectural Component Interaction (FIGS. 4, 15)

In a sample implementation, the different components of the interaction are shown (FIG. 4). The client requests (500) are processed by the app server and the wallet server sends signed transactions (501) to a relayer module (390), which will verify the user and create a payload with user desired actions and broadcast to the blockchain on behalf of the user for gasless transactions (502). Smart contact functions are invoked based on user actions (503) and the transactions are recorded on the blockchain (504). The blockchain listener module listens to events on the blockchain and queries the transactions from the blockchain (505) and stores them on the server. The client requests (500) to get a list of tokens are processed by the wallet module (507). The Smart contract queries to get the list of tokens associated with the wallet account (508).

To store medical imaging data off-chain and on-chain, while utilizing zero knowledge proofs (ZKPs) and wallet gating with asymmetric key encryption, the following technical frameworks will be leveraged (FIG. 15).

The patient data is uploaded and encrypted to a secure cloud storage (182). The data may include the patient imaging study for a radiology study or any other relevant information pertaining to the patient study. The DICOM file undergoes processing to extract both the medical image data and metadata information (183). Subsequently, both components are encrypted to ensure security (181). The encrypted data is then stored in a secure storage system and a secured database (182). This process safeguards the confidentiality and integrity of medical imaging data, protecting it from unauthorized access or breaches while enabling efficient management and retrieval. Off-chain storage (182) may be set up on a secure cloud server, such as AWS S3, or a similar centralized or decentralized storage system like IPFS (185), where the actual medical imaging data and metadata (183) will be stored respectively. In the sample implementation, a centralized data storage is shown (182). This off-chain storage ensures compliance with privacy regulations, such as HIPAA, and provides scalability for large image files. Strong cryptographic protocols are established to store the data on cloud, including customer managed keys or using the user's public key.

An encrypted reference (184) to the medical image study data and encrypted metadata are stored on a decentralized storage, such as IPFS (185). This metadata can include information such as patient details (public key, non-PII information), imaging modality, timestamps, and references to the medical image storage location. In some configurations, the on-chain metadata includes a token URI (184) or an identifier information referencing the encrypted metadata information and reference stored on the decentralized storage, such as the Interplanetary File System. Storing a locator on the blockchain ensures cost-effective and responsive blockchain systems and provides transparency, immutability, and easy access to essential information.

The system initiates transactions for minting, sharing, and revoking access to patient data (186). Smart contract methods (188) handle these transactions, and their execution results are recorded on the blockchain. In a blockchain network, smart contract execution on individual peer nodes can result in the addition of a new block (189) to the blockchain when certain conditions are met.

In the case that the user initiates a transaction (181), the user sends a transaction request, which may involve interacting with a smart contract deployed on the blockchain network. The transaction request specifies the intended action, parameters, and any associated data. The transaction request is broadcasted to the network of nodes (peers) in the blockchain network (187). Each node in the network validates the transaction, including verifying digital signatures, ensuring the user has sufficient funds or permissions, and confirming the integrity of the smart contract code. If the transaction involves interacting with a smart contract, the node checks the validity of the interaction and the parameters passed to the contract. If the transaction involves interacting with a smart contract, the node executes the code of the smart contract to process the transaction. The smart contract's logic is executed deterministically, and its state may be updated based on the outcome of the transaction (188).

Valid transactions, including interactions with smart contracts, are grouped together into a block by miners (or mining nodes) through the process of mining. Upon receiving a new block, each node validates its contents, including the transactions involving smart contracts. This validation process ensures that the transactions and associated smart contract interactions adhere to the rules of the blockchain protocol (190).

The addition of the new block (189) is confirmed through the consensus mechanism of the blockchain network (187). Nodes must agree on the validity of the block and the smart contract interactions before it is permanently added to the blockchain (190). The newly added block (189), containing validated transactions and smart contract interactions, is propagated to all other nodes in the network (187), ensuring consensus and synchronicity across the blockchain ledger (190). If nodes produce varying results, the consensus mechanism resolves conflicts by favoring the majority opinion, ensuring integrity.

Blockchain

Referring to FIG. 29, an example of a blockchain in accordance with a non-limiting embodiment of the disclosure is shown. The blockchain serves as a decentralized ledger that records transactions related to the creation, sharing, and access of medical images. This ensures that data integrity is maintained and that all interactions with the data are transparent and traceable.

Information Stored on the Blockchain:

NFT of Imaging Study: NFT (Non fungible token)—a unique cryptographic token that represents ownership of a specific digital asset. In this case, the NFT represents a medical imaging study, and the owner is the patient (in FIG. 29, the Owner (Patient) data in the NFT comprises the patient cryptographic wallet address) for whom the study was conducted. The NFT includes the owner information, smart contract and metadata, and references the patient medical data stored on the cloud.

Reference to Metadata of Medical Study: The blockchain itself does not store the actual medical data (the medical study metadata or images). Instead, it stores a URI (Uniform Resource Identifier) (e.g., the link in FIG. 29) that points to the location where the asset's metadata and content are stored, often on a decentralized storage system like IPFS (InterPlanetary File System), that uniquely identifies the NFT's metadata file on IPFS. In the system's implementation, each NFT on the blockchain contains an encrypted universal resource identifier which references a .json file on a decentralized server like IPFS information such as the type of scan (e.g., MRI, CT), the date and time of creation, the healthcare provider's details, and the patient's anonymized ID. This metadata file itself contains a field that references an encrypted address of the images of the medical study stored on a cloud storage. The medical study metadata JSON on IPFS and Imaging Data on the cloud are encrypted with the patient's public key.

By storing only the URI on the blockchain and keeping the larger media files off-chain on IPFS and Cloud Storage, the NFTs can leverage the immutability and decentralization of the blockchain while avoiding the high costs of on-chain storage. The IPFS network ensures that the NFT data remains accessible and tamper-proof, as the content is identified by its unique CID and can be replicated across multiple nodes.

Access Control Information: Details of who has ownership and access to specific images, including healthcare providers and the patient, as provided in the Non Fungible Token.

Transaction Logs: Records of all actions taken on the images, such as uploads, access requests, and sharing permissions granted or revoked. The Blockchain Transaction (Txn) log includes, for example, a transaction ID, transaction type, wallet addresses (patient and/or healthcare provider), and transaction time.

Smart Contracts: These self-implementing programs secure and automate the process of validating trusted issuers, minting NFTs, granting and revoking access, managing consent, and verifying the integrity of the data. The Smart Contract in FIG. 29 includes, for example, whitelist of verified or authorized hierarchical-deterministic healthcare provider cryptographic wallets.

In operation, a $1^{st}$ step is for the Authorized Provider to Upload a Medical Study. Here, an authorized healthcare provider or institution uploads a medical study, such as imaging scans or test results, to the system.

A $2^{nd}$ step is for the Study to be Split into Metadata and Data (Images). Here, the medical study is split into two parts: metadata (patient information, study details, etc.) and the actual data (medical images, test results, etc.). See, for example, step (183) of FIG. 15, by the server (182).

At a 3rd step, Medical Images are Uploaded to the Cloud Storage, Encrypted with Patient Public Key, and Generate the URI. Here, the medical images or data files are uploaded to a secure cloud storage system. Each file is encrypted using the patient's public key to ensure privacy and confidentiality. See, for example, server (182) of FIG. 15. A Uniform Resource Identifier (URI) is generated for each encrypted file, which serves as a pointer to its location in the cloud storage. See, for example, step (184) of FIG. 15, by the server (182).

At a $4^{th}$ step, the JSON File is Created with Metadata+ Cloud Storage URI, Encrypt with Patient Public Key, Generate URI. Here, a JSON (JavaScript Object Notation) file is created, containing the metadata of the medical study and the URIs of the encrypted data files in the cloud storage. This JSON file is then encrypted using the patient's public key. A URI is generated for this encrypted JSON file. See, for example, the IPFS/decentralized storage (185) of FIG. 15, by the server (182).

A $5^{th}$ step is to Create Transaction with NFT on Blockchain Containing URI, the owning Patient Wallet, Access Rules, and Digital Signature. A transaction is created on the blockchain to mint a new Non-Fungible Token (NFT). This NFT contains the URI of the encrypted JSON file, the patient's wallet address (to assign ownership), access rules (specifying who can access the data), and a digital signature from the authorized provider or institution. The blockchain transaction includes but is not limited to including a unique transaction id, transaction type, sending and receiving wallet addresses, and a time stamp, for example, step (186) of FIG. 15, at the nodes (187) of the blockchain layer (280).

The transaction ID is a unique identifier generated for each transaction on the blockchain. It serves as a fingerprint that distinguishes one transaction from another. When a new transaction is initiated, it is assigned a transaction ID, which is then broadcasted to the network for validation and inclusion in the next block. The transaction type specifies the nature of the transaction, such as a transfer of cryptocurrency, a smart contract execution, or a token issuance. This information is essential for the nodes (participants) in the network to process the transaction correctly and update the blockchain accordingly. Every transaction on the blockchain involves at least one sender address and one recipient address. These cryptographic wallet addresses are derived from the users' public keys and are used to identify the parties involved in the transaction. The timestamp records the precise time when the transaction was initiated. It helps establish the chronological order of transactions within a block and across the entire blockchain. Timestamps are crucial for maintaining the integrity and immutability of the blockchain.

A $6^{th}$ step is for the Nodes to Validate the Transaction Using Consensus Mechanisms. The transaction is broadcasted to the blockchain network, and the nodes (participants) in the network validate the transaction using consensus mechanisms, such as Proof-of-Work or Proof-of-Stake, to ensure its legitimacy and integrity. See, for example, FIG. 15 by the blockchain nodes (187).

A $7^{th}$ step is that the Validated Transaction is Added to a New Block. Once the transaction is validated by the consensus mechanisms, it is included in a new block on the blockchain. See, for example, step (189) of FIG. 15, by the blockchain nodes (187).

An $8^{th}$ step is to Update the Blockchain: The New Block is Added to the Blockchain, and All Nodes Update Their Copies. The new block containing the validated transaction is added to the blockchain, and all nodes in the network update their copies of the blockchain to reflect this addition. See, for example, step (190) of FIG. 15, by the blockchain nodes (187). The nodes can include, for example, the cloud storage, healthcare provider system and patient computer.

A $9^{th}$ step is to Manage Access: Smart Contracts Manage and Log Access to the NFT. Smart contracts on the blockchain manage and log access to the NFT (and consequently, the medical data) based on the predefined access rules. Only authorized parties (for example, verified healthcare providers and the owner patient) with the correct permissions can access and decrypt the data using their private keys. See, for example, step (188) of FIG. 15, by the blockchain nodes (187).

CONCLUSION

This system (5) proposes a novel technical architecture designed to revolutionize data management across industries. This system prioritizes security, interoperability, integration, user-friendliness, flexibility, and scalability, making it adaptable to a wide range of applications and data types.

The system (5) has a number of advantages, including but not limited to:

Enhanced Security and Decentralized Access Control: The system leverages blockchain technology to decentralize access control, eliminating single points of failure and bolstering security against cyberattacks. Data access is controlled through individual user wallets and private keys, empowering users with control over their information.

On the blockchain, a reference to a decentralized storage Uniform Resource Identifier (URI) is stored. This IPFS link is encrypted and contains metadata about the imaging study, specifically extracted DICOM metadata, and a URI of the imaging studies themselves. The differentiating aspect of this system lies in its unique approach to data storage and security, achieved through the use of a blockchain wallet.

This system offers unparalleled security by protecting each piece of data with an individual ownership key, significantly mitigating the risk of breaches. Additionally, the system ensures interoperability and immutability of transactions, providing transparency throughout the data lifecycle. By transferring the liability of data ownership and sharing to the patient, the system further enhances accountability and security. This multi-layered security approach ensures that medical imaging data is securely stored and shared, maintaining data integrity and patient confidentiality at all times.

Improved Scalability and Cost-Effectiveness: The architecture utilizes off-chain data storage with blockchain-based hashing or integrates decentralized storage solutions. This avoids storing large amounts of data directly on the blockchain, significantly reducing transaction costs and improving processing speeds, making the system highly scalable and cost-effective for widespread adoption.

Increased Interoperability: Unlike traditional private blockchains, this approach fosters better interoperability within various ecosystems. By utilizing mechanisms like public blockchains for specific data elements, the system facilitates smoother data exchange between different institutions and organizations. This improved interoperability can enhance collaboration and efficiency.

Streamlined Consent Management with Multi-Sig Technology: The system automates consent management through multi-signature methods. This ensures data is only released or transmitted after obtaining approval from all authorized parties, streamlining data sharing and reducing reliance on manual processes. Additionally, multi-sig transactions create tamper-proof audit trails, simplifying compliance with data privacy regulations.

Increased User Privacy: The architecture promotes user privacy by allowing users to prove they possess certain credentials without revealing the actual data itself or their identity. This approach protects sensitive information while still enabling authorized access for legitimate purposes.

User-Friendly and Flexible Design: The system is designed to be user-friendly and adaptable. It can integrate with existing digital wallet modules and offers modular components, allowing for customization to specific industry needs.

Beyond Healthcare: While this disclosure focuses on healthcare data management, the core architecture extends far beyond this single industry. Its flexibility and security make it applicable to any industry and any form of data, from financial records and supply chain management to intellectual property and academic research. This system (5) has the potential to create a more secure, interoperable, and user-centric data management landscape across the globe.

This novel technical architecture offers a glimpse into a future where data security, interoperability, and user control are paramount. It lays the foundation for a more efficient, collaborative, and privacy-preserving approach to data management across all industries.

The disclosure provides a number of embodiments, including:

A. A system and method for establishing authorized trusted issuers within a blockchain-based system for data management. The system created a framework to identify and verify healthcare providers who can issue medical data and imaging studies. For this application, trusted issuers are authenticated entities responsible for conducting imaging studies or other medical procedures, such as doctors, radiologists, or technicians. The smart contracts validate transactions initiated by trusted issuers to mint NFTs representing medical data on the blockchain. Minting creates a new digital record (NFT) on the blockchain. NFTs are unique and non-fungible tokens, meaning each NFT represents a specific piece of medical data and cannot be replicated or replaced by another NFT.

B. A system and method that automatically triggers the post-processing and extraction of medical image studies into 'medical images' and 'metadata' upon detection of medical imaging study files in a designated local location (such as a Picture Archiving and Communication Systems) or upon upload into a system after verification that the origination of the image is from a trusted issuer. Medical Images are the actual image data itself. Metadata is the additional data about the image, such as patient information, date of acquisition, and type of study.

C. A system and method for autonomously generating a secure digital wallet for the patient associated with a specific medical image study, wherein the patient's identity is verified and authenticated within the blockchain-based system, eliminating the need for separate verification steps, and wherein a hierarchical deterministic wallet is generated on behalf of the patient without requiring direct intervention from the patient. The system automatically generates a wallet for the patient, and secures a patient's medical scans by splitting the image from their personal details and storing these details safely on a trusted digital network. Hierarchical Deterministic Wallet can be, for example, a special type of cryptographic wallet that works like a keychain with a master key. The system will own a single master seed phrase, stored in a secure vault, from which an infinite quantity of child keys can be automatically and mathematically derived for each user in the system without having to be stored in the system for enhanced security.

D. A system and method for wallet setup and multi-factor authentication within a blockchain-based system comprising generating wallet key pairs programmatically utilizing a master private key derived from a seed phrase, securing the master private key derived from the seed phrase within a vault, utilizing system-managed wallet key pairs derived as child keys programmatically from the secured master private key, implementing multi-factor authentication mechanisms to authenticate users accessing the system, integrating the generated wallet key pairs with the multi-factor authentication process to enhance security and user authentication within the blockchain-based system. This sets up secure wallets and logins within a blockchain system. The system creates and verifies the existence of user wallets in the system, making the management of medical data on a blockchain system secure and convenient. The wallet key pairs can be, for example, a combination of private and public keys used to access your data on the blockchain. The private key is like the master key, kept secret, while the public key can be shared for specific purposes. The seed phrase can be, for example, a set of random characters used to generate wallet keys, as a secret code for creating all keys. The multi-factor authentication can be, for example, a security method requiring multiple steps to login, beyond only a password.

E. A system and method for securely storing medical image studies in a cloud storage solution, wherein an automated process triggers the upload of the original file, 'medical images' and 'metadata' to the cloud after processing, and wherein the files are encrypted with the patient's public key before storage. This system automatically uploads medical scans to a secure cloud storage and encrypts them with a special code, unique to each owner of the record, for maximum protection, so that only the owner of the record can access the images. The Medical Images can include, for example, the actual picture of the scan (X-ray, MRI, etc.). The metadata is additional information about the scan, like name, date, and type of scan. Encryption is a process that secures data with a special code (key) so only authorized users can access it. The Patient's Private Key is a unique code used to decrypt the patient's medical using keys generated from and the HD algorithm.

F. A system and method for autonomously storing encrypted metadata with a reference to the medical images stored on the secure cloud system on a distributed storage network, such as the Interplanetary File System, through an encrypted URI. The system and method for autonomously storing encrypted, non-image data (metadata) related to medical scans on a separate network. This network, like the Interplanetary File System (IPFS), is a decentralized storage system that offers increased security and redundancy for the metadata. Additionally, the system creates a secure link within the original storage location (cloud) that points to the location of the metadata on the distributed network, allowing users to access both parts of the medical data package. The Metadata is, for example, additional information about the medical image, such as patient name, date, and type of scan. Encrypted is data that has been secured with a special code (key) for security purposes. Distributed Storage Network can be, for example, a network where data is stored across multiple locations, offering redundancy and improved security. The Interplanetary File System (IPFS) can be, for example, a specific example of a distributed storage network. A Secure Reference can be, for example, a mechanism within the cloud storage system that points to the location of the encrypted metadata on the distributed network through an encrypted URI. An Encrypted URI Reference is where the system creates an encrypted Uniform Resource Identifier (URI) within the cloud storage system. This encrypted URI acts as a secure pointer that references the location of the encrypted metadata on the distributed network.

G. A system and method for minting Non-Fungible Tokens (NFTs) representing medical image studies on a blockchain, wherein a smart contract verifies transactions from trusted providers and mints NFTs with patients as owners, and wherein the NFTs contain encrypted references to metadata stored in a decentralized storage system. The system and method creates a unique digital certificates (NFTs) on a blockchain network to represent ownership of medical scans. A secure program on the blockchain (smart contract) verifies that healthcare providers submitting the data are authorized. Once verified, the system creates a unique NFT for each scan, with the patient listed as the owner. These certificates contain encrypted references, like a secure code, that point to where additional details about the scan (images, metadata) are stored on a separate, secure network. Non-Fungible Token (NFT) can be, for example, unique digital certificate on a blockchain that represents ownership of a digital asset. A Medical Image Study can be, for example, a collection of medical images, such as X-rays or MRIs, related to a specific patient and procedure. Blockchain can be, for example, a secure digital ledger that records transactions transparently. Smart Contract can be, for example, a self-executing program on a blockchain that can automatically execute predefined actions. Trusted Provider can be, for example, an authorized healthcare provider (doctor, hospital) verified to submit medical data. An Encrypted Reference can be, for example, a scrambled code pointing to the location of the metadata stored on a separate network. Decentralized Storage System can be, for example, a network where data is stored across multiple locations, offering improved security and redundancy.

H. An authentication mechanism for validating patients' identities and verifying their consent to access the released medical images. The system and method can incorporate multi-signature wallets, which require the patient to provide authorization and consent before minting an NFT by a trusted provider. Each transaction is timestamped and cryptographically secured, providing a transparent and auditable trail of patient consent actions for regulatory compliance and accountability. The system and method can, for example, confirm a patient's identity and obtain their permission before creating a digital ownership certificate (NFT) for their medical scans on a blockchain network. First, the system verifies the patient's identity using secure methods. Second, the patient receives clear information about the NFT and then grants permission to receive it through a special digital wallet signature that requires multiple approvals (multi-signature wallet). One approval comes from the patient to allow the release of their records on the blockchain, while another comes from a trusted healthcare provider confirming the data's validity. Importantly, all actions, including the time and digital signatures, are recorded permanently on the blockchain, creating a clear and verifiable record of patient consent for regulatory purposes and accountability. Authentication Mechanism can be, for example, a method for verifying a user's identity. Multi-Signature Wallet can be, for example, a digital wallet requiring multiple approvals to authorize transactions. NFT (Non-Fungible Token) can be, for example, a unique digital certificate on a blockchain that represents ownership of a digital asset. Consent can be, for example, permission granted by the patient to release their medical data. Cryptographic Signature can be, for example, a digital signature that verifies the authenticity and integrity of a transaction. Audit Trail can be, for example, a chronological record of actions and approvals.

I. An access control system for granting view access to medical image NFTs by other parties, wherein access is gated by authentication through cryptographic signing and zero-knowledge proofs (ZKPs). This provides a secure access control system for granting controlled viewing access to medical image NFTs on a blockchain network. The secure system for controlling access to digital ownership certificates (NFTs) representing medical scans on a blockchain network. This system acts like a secure gatekeeper, requiring authorized users (like doctors or researchers) to prove their identity and qualifications before viewing the medical images. Users prove their identity using a secure method like a digital signature. Then a special cryptographic technique (zero-knowledge proofs) is used to demonstrate they have the necessary qualifications (e.g., doctor's license) without revealing the details of those qualifications. Based on these steps, the system grants specific viewing access to the medical image NFT. This access might be limited, allowing users to only view the images for a specific purpose or timeframe. This approach ensures patient privacy while allowing authorized personnel to access the medical data when necessary. Access Control System can be, for example, a system that regulates access to resources based on user permissions. The Medical Image NFT can be, for example, a unique digital certificate on a blockchain representing ownership of a medical scan. Authentication can be, for example, verifying a user's identity. Cryptographic Signing can be, for example, using a private key to verify the identity of the sender and the integrity of a message. Zero-Knowledge Proofs (ZKPs) can be, for example, a cryptographic technique allowing users to prove they possess certain information without revealing the information itself.

J. A system and method for facilitating secure and auditable sharing of medical data between patients and authorized recipients, wherein patients initiate share requests through their cryptographic wallets, and wherein smart contracts automatically and autonomously enforce access permissions and record sharing transactions on the blockchain ledger for transparency and accountability. This describes a secure and auditable system for patients to share their medical data with authorized recipients on a blockchain network. This proposes a secure and traceable system and method for patients to share their medical information on a blockchain network. Patients use their secure digital wallets to initiate requests to share their medical data (represented by digital ownership certificates-NFTs) with authorized individuals (like doctors). The system relies on smart contracts, which act like pre-programmed agreements on the blockchain. These agreements define who can access the data and under what limitations (e.g., view-only access for a specific timeframe). Every time a patient shares their data, a record of this event is permanently stored on the blockchain. This record details who shared with whom and what permissions were granted. This transparency helps ensure patient privacy is respected and promotes accountability. Smart Contract can be, for example, a self-executing program on a blockchain that can automatically manage agreements and transactions. Access Permissions can be, for example, a Rules defining who can access data and under what conditions (e.g., view-only, time-limited).

K. An authorization framework for validating share requests and enforcing access permissions, wherein authorized recipients are required to authenticate their identities and provide proof of authorization before gaining access to shared medical data, and wherein smart contracts govern the execution of share transactions based on predefined rules. This can be, for example, a comprehensive authorization system for securely sharing medical information on a blockchain network. This system goes beyond simply granting access; it verifies who is trying to access the data and ensures they have the right to do so. Authorized recipients (like doctors or researchers) need to prove their identity using secure system and methods. They then need to demonstrate they have permission to access the specific data being shared. This permission might come directly from the patient or be based on predefined rules within the system (e.g., a doctor's license for a specific hospital). Smart contracts, which act like pre-programmed agreements on the blockchain, control access. These agreements define the rules for sharing (e.g., view-only access for a specific timeframe) and only grant access when all verification steps are complete. This approach ensures that only authorized individuals with the proper permissions can access shared medical data, providing an extra layer of security and control. Authorization Framework can be, for example, a system for managing access permissions and verifying user entitlements. Share Requests can be, for example, requests from patients to share their medical data with specific recipients. Access Permissions can be, for example, Rules defining who can access data and under what conditions (e.g., view-only, time-limited). Smart Contract can be, for example, a self-executing program on a blockchain that can automatically manage agreements and transactions. Cryptographic Signing can be, for example, a system and method using a private key to verify the identity of the sender and the integrity of a message.

L. A secure and auditable revocation mechanism integrated into the platform, enabling patients to revoke access permissions by updating the state of the smart contract and cryptographic authentication and verification processes, ensuring the integrity and confidentiality of the revocation request. This proposes a secure and traceable method for patients to take back control of their shared medical data on a blockchain network. Even after granting access to users like doctors, researchers, or family, patients can revoke those permissions at any time. Patients initiate the revocation process through the system. This updates the pre-defined agreements on the blockchain (smart contracts) associated with the shared data, essentially revoking access for the recipient. Secure system and methods using digital signatures (cryptographic authentication and verification) ensure the integrity of the request and confirm the patient's identity as the data owner. Importantly, the entire event, including the time of revocation and the patient who revoked access, is permanently recorded on the blockchain. This record provides transparency and accountability within the system. Revocation Mechanism can be, for example, a process for withdrawing previously granted access permissions. Smart Contract can be, for example, a self-executing program on a blockchain that can automatically manage agreements and transactions. Cryptographic Authentication and Verification can be, for example, a system and methods using digital signatures to ensure the integrity and authenticity of information. Immutable Audit Trail can be, for example, a permanent and unchangeable record of all events within the system.

M. A secure and auditable request mechanism integrated into the medical data management system, allowing trusted issuers to submit requests for medical images from other healthcare institutions, agnostic of their enrollment in the system, by providing relevant patient details, such as name, date of birth, and other personal identifiers, along with appropriate authorization credentials. This proposes a secure and traceable method for authorized healthcare providers (like doctors) to request medical scans from other hospitals, regardless of whether they are current users of the system. Authorized providers can submit secure requests for specific medical images through the platform. The request includes details about the patient (name, date of birth) to ensure they are requesting the correct information. To validate their access rights, providers need to demonstrate they have permission to access the data. This permission could come directly from the patient (their consent) or from agreements between healthcare institutions allowing data sharing for specific purposes. Importantly, every request, including details about the patient, the authorization used, and the time of the request, is permanently recorded on the blockchain network. This record provides transparency and accountability within the system. Trusted Issuer can be, for example, an authorized healthcare provider with permission to request medical data. Institutional Agreements can be, for example, Agreements between healthcare institutions allowing authorized personnel to request medical data for specific purposes. Authorization Credentials can be, for example, proof that the issuer has the right to request the data (patient consent or institutional agreements).

N. A system and method for automating patient consent using NFTs, wherein patients provide consent for sharing medical images by interacting with NFTs representing their studies, and wherein consented information is recorded as immutable transactions on the blockchain. This proposes a new way for patients to grant permission for sharing their medical scans using a system built on a blockchain network. Medical scans are represented by unique digital certificates called NFTs. Patients can directly grant permission to share their scans by interacting with these certificates within the system. This interaction might involve approving a request or digitally signing a consent form linked to a smart contract that controls the issuance of the NFT. Once a patient grants permission, this information is permanently recorded on the blockchain, similar to a secure and unchangeable ledger. This ensures a clear and verifiable record of patient consent, which is important for regulations and keeping track of permissions. NFT (Non-Fungible Token) can be, for example, a unique digital certificate on a blockchain that represents ownership of a digital asset. Immutable Transaction can be, for example, a record on the blockchain that cannot be altered or deleted. Digital Signing can be, for example, a method using a private key to verify the identity of the sender and their approval of an action.

O. A system and method for enabling gasless transactions on a blockchain, wherein a relayer module pays for transaction fees on behalf of users, allowing users to perform actions on the blockchain without paying fees and abstracting the concept of blockchain from the user. This proposes a method for users to interact with a blockchain network without needing to pay transaction fees directly, let alone knowing they are interacting with the blockchain. A module called a relayer acts as a middleman with a wallet, covering the transaction fees (also referred to as gas fees) on behalf of users. Users initiate actions on the blockchain (like creating digital certificates or sharing data). The relayer then pays the gas fee and broadcasts the user's transaction to the network for processing.

P. A custom, integrated blockchain explorer tool for viewing transactions recorded on a blockchain in real-time, providing a user-friendly interface for searching specific transactions, addresses, or relevant details, and wherein users can view and analyze blockchain transactions in real-time. This proposes a new blockchain explorer tool that goes beyond simply viewing past transactions. This tool allows users to see transactions happening in real-time: Witness data being added to the blockchain as it occurs; search for specific transactions: find transactions based on unique identifiers, wallet addresses, or keywords within the data; analyze transactions in detail: Go beyond basic information and explore data visualizations, block details, and even view transactions waiting to be processed on the network. This comprehensive approach offers greater transparency and facilitates data-driven decision making within the blockchain ecosystem. Blockchain Explorer can be, for example, a web-based tool for searching, viewing, and analyzing transactions on a blockchain network. Transaction can be, for example, a record of data transfer or interaction on a blockchain network. Transaction Hash can be, for example, a unique identifier for each transaction on the blockchain. Mempool can be, for example, a temporary pool of transactions waiting to be included in a block on the blockchain.

Q. A system and method for auditing and monitoring the activities of authorized trusted issuers within the medical data management system, wherein blockchain-based transaction logs and smart contract events are used to track the actions and interactions of trusted issuers, ensuring compliance with regulations and standards. This proposes a method for monitoring the activities of authorized healthcare providers (like doctors in hospitals) within a medical data sharing system built on a blockchain network. Every time a doctor requests medical scans, shares data, views or downloads data, this activity is permanently recorded on the blockchain. This record acts like a tamper-proof log of their actions. Trusted Issuer can be, for example, an authorized healthcare provider with permission to request medical data. Transaction Logs can be, for example, Records of all transactions on the blockchain network. Smart Contract Events can be, for example, a Specific data points recorded within smart contract executions. HIPAA is the Health Insurance Portability and Accountability Act. Data Sharing Protocols can be, for example, established procedures for securely sharing sensitive medical data.

R. An authentication mechanism for verifying the credentials and accreditation of authorized trusted issuers before granting them access to the medical data management system. This proposes a secure login system for authorized healthcare providers before they can access the medical data sharing system. Doctors need to go through a multi-step login process, potentially involving a password, a temporary code sent to their phone or email. Beyond simply logging in, the system also verifies that the doctor is who they say they are and has the proper qualifications. This verification might involve checking with official licensing boards or using special blockchain technology to confirm their credentials securely. This two-pronged approach ensures that only authorized and qualified healthcare providers can access patient data within the system. Trusted Issuer can be, for example, an authorized healthcare provider with permission to request medical data. Multi-Factor Authentication (MFA) can be, for example, a security method requiring multiple verification steps to confirm a user's identity. One-Time Passcode (OTP) can be, for example, a temporary code used for authentication, often sent via SMS or generated by an app. Decentralized Identity Management can be, for example, a blockchain-based system for storing and verifying credentials securely.

S. A system and method for tracking and auditing shared medical data transactions on the blockchain ledger, wherein all share requests, approvals, access, and revoke activities are recorded as immutable and transparent entries on the blockchain, providing patients with visibility into the usage and dissemination of their healthcare information. This proposes a method for keeping a detailed record of everything that happens to shared medical data within this system.

Imagine a secure and unchangeable logbook on a blockchain network that tracks all activity including without limitation: when a patient allows someone to see their scans; when someone with permission actually accesses those scans or downloads the data; when a patient decides to revoke access from someone; when a patient requests access to scans; when a patient's request of scans is viewed, processing, or fulfilled. Patients can then access this logbook and see exactly who has seen their data and when. This transparency helps patients feel more in control of their medical information. Share Requests can be, for example, requests from patients to share their data with specific recipients. Access Events can be, for example, recording instances where authorized users access the shared data.

T. Flexibility of the modular framework to make it adaptable to use externally managed wallet services, if required. This emphasizes that the system is built to be flexible. The different parts of the system (like login and data access) are designed to work with different digital wallet services. Patients wouldn't be limited to using a specific wallet built into this platform. They could use their existing wallets or wallets from other companies.

Further example embodiments include:

A) A module for managing medical data on a blockchain by ensuring only authorized healthcare providers can create new digital records. The process starts with healthcare providers registering through a dedicated user interface, providing their credentials (username, password, email). This information establishes a user account linked to a unique cryptographic wallet address. Next, a trusted issuer registration module verifies the provider's identity by checking their National Provider Identifier (NPI) and validating their email address. Based on this verification, the system determines if the provider is authorized to create medical data records on the blockchain. If authorized, a secure cryptographic wallet is generated for the provider using a hierarchical-deterministic (HD) approach. This HD wallet is derived from a master key stored in a secure vault, ensuring a vast pool of unique child keys, including a public and private key for the provider. The generated wallet is then linked to the provider's user account using their email address. Finally, the system interacts with a smart contract on the blockchain layer. This smart contract maintains a whitelist of authorized provider wallet addresses. Upon successful verification by the trusted issuer module, the provider's wallet address is added to this whitelist. Additionally, the smart contract ensures that only whitelisted wallet addresses can create new digital records (NFTs) representing medical data on the blockchain. This approach ensures secure and controlled management of medical data by verifying and granting access only to authorized healthcare providers.

B) A method for automatically processing and extracting data from medical image studies within a system, comprising: a. Medical Imaging Data Monitoring: The system utilizes a data monitoring module residing within the application layer. This module is configured to continuously monitor a designated local storage location, such as a Picture Archiving and Communication Systems (PACS), for the presence of new medical imaging study files. Alternatively, the data monitoring module can be configured to monitor a designated upload interface within the system for incoming medical imaging study files. b. Image Origin Verification: An origin verification module, also residing within the application layer, is employed to verify the origin of a newly detected medical imaging study file. This verification process ensures that the file originates from a trusted issuer healthcare provider user account. Trusted issuers are identified by unique cryptographic wallet addresses included in a whitelist maintained by a smart contract on a blockchain layer. c. Automated Image Processing and Data Extraction: Upon successful origin verification of the new medical imaging study file, a medical image processing module is triggered. This module is configured to automatically perform post-processing tasks on the verified file. Subsequently, the medical image processing module extracts two key pieces of data: Medical Images: This refers to the actual image data itself. Metadata: This encompasses additional data about the image, such as patient information, date of acquisition, and the type of study. By employing this automated method, the system ensures secure and efficient handling of medical image studies. The system only processes files originating from authorized sources and extracts relevant medical data for further use. This method leverages blockchain technology through the use of whitelists and smart contracts to ensure the integrity and security of the image origin verification process.

C) A system for autonomously generating a secure digital wallet for the patient associated with a specific medical image study, comprising: an identity verification module configured to verify and authenticate the patient's identity within the blockchain-based system, eliminating the need for separate verification steps; a hierarchical deterministic wallet generation module configured to automatically generate a hierarchical deterministic wallet on behalf of the patient, wherein said hierarchical deterministic wallet is generated without requiring direct intervention from the patient; a secure vault module configured to store a master private key derived from a seed phrase, wherein the master private key is used to programmatically generate an infinite number of child keys; a key management module configured to derive child keys for each patient using the master private key, ensuring that each patient's hierarchical deterministic wallet includes a unique wallet key pair, having a private key and a public key; a multi-factor authentication module configured to implement multi-factor authentication mechanisms to authenticate users accessing the system, integrating the generated wallet key pairs with the multi-factor authentication process to enhance security and user authentication within the blockchain-based system; and a data storage module configured to securely store the medical image studies and associated patient details, ensuring that the medical images and personal information are split and stored securely on a trusted digital network.

D) A method for securely storing medical image studies in a cloud storage solution, comprising: Automated Upload Process: An automated process configured to trigger the upload of original medical image files and associated metadata to a cloud storage solution after initial processing. Medical Images: Include various types of scans such as X-rays, MRIs, CT scans, etc. Metadata: Includes supplementary information about the scans such as the patient's name, date of the scan, type of scan, and other relevant details. Encryption Mechanism: The method includes encrypting the medical images and metadata using the patient's hierarchical-deterministic cryptographic wallet public key prior to storage in the cloud. Patient's Hierarchical-Deterministic Cryptographic Wallet: A hierarchical-deterministic cryptographic wallet associated with the patient. Private Key: A unique cryptographic key used for encryption, ensuring that only the patient (or an authorized entity) can decrypt and access the medical images and metadata.

Automated Trigger Mechanism: An automated trigger mechanism configured to initiate the upload process upon the completion of processing the medical images and metadata. Encryption Process: The encryption process utilizes the private key from the patient's hierarchical-deterministic cryptographic wallet, ensuring that: Data Security: Medical images and metadata are securely encrypted before being uploaded to the cloud. Access Control: Only the owner of the cryptographic wallet (the patient) or an authorized entity can decrypt and access the stored data. Cloud Storage Solution: The cloud storage solution is configured to store the encrypted medical images and metadata securely, providing scalable and reliable storage while maintaining high standards of data security and privacy. Validation and Verification: The method includes validation and verification processes to ensure that: Data Integrity: The uploaded medical images and metadata maintain their integrity and are not altered during the encryption and upload process. Access Verification: Only authorized access to the encrypted data is permitted, based on the cryptographic wallet's access controls. Redundancy and Backup: The cloud storage solution includes redundancy and backup mechanisms to ensure that the encrypted medical images and metadata are preserved and can be recovered in case of data loss or corruption.

E) A system for autonomously storing encrypted metadata with a reference to medical images stored on a secure cloud system on a distributed storage network, such as the Interplanetary File System (IPFS), through an encrypted Uniform Resource Identifier (URI), comprising: an automated metadata encryption module configured to encrypt metadata associated with medical images, wherein said metadata includes patient information, date, type of scan, and other relevant details; an upload module configured to autonomously upload the encrypted metadata to a distributed storage network, such as IPFS, wherein said distributed storage network provides enhanced security and redundancy by storing data across multiple locations; a reference generation module configured to create an encrypted URI within the secure cloud system, wherein said encrypted URI serves as a secure pointer that references the location of the encrypted metadata on the distributed storage network; wherein said secure cloud system stores the original medical images and maintains the encrypted URI reference to ensure seamless access to both the medical images and the associated metadata, enabling authorized users to retrieve and decrypt the metadata from the distributed storage network using the encrypted URI; and a verification module configured to validate the integrity and authenticity of the encrypted metadata and the encrypted URI reference, ensuring that only authorized access to the encrypted metadata is permitted.

F) A system for minting Non-Fungible Tokens (NFTs) representing medical image studies on a blockchain, comprising: a smart contract module configured to verify transactions from trusted providers, wherein said trusted providers include authorized healthcare entities such as doctors and hospitals verified to submit medical data; a minting module configured to mint NFTs upon successful verification by the smart contract module of the trusted issuer, wherein each NFT represents a specific medical image study and includes the patient as the owner of the NFT; a metadata encryption module configured to generate encrypted references to metadata associated with the medical image studies, wherein said metadata includes patient information, date of the scan, type of scan, and other relevant details; a decentralized storage module configured to store the encrypted metadata on a decentralized storage system, providing enhanced security and redundancy by distributing data across multiple locations; wherein the NFTs contain the encrypted references generated by the metadata encryption module, said encrypted references acting as secure pointers to the metadata stored in the decentralized storage system; and an access control module configured to ensure that only authorized users can access and decrypt the metadata referenced by the NFTs, maintaining the security and integrity of the medical image studies and their associated metadata.

G) A system for an authentication mechanism for validating patients' identities and verifying their consent to access released medical images, comprising: an identity verification module configured to authenticate a patient's identity using secure methods, ensuring that the patient is correctly identified before any further actions are taken; a consent verification module configured to provide clear information about the Non-Fungible Token (NFT) to the patient, wherein the NFT represents ownership of the patient's medical image studies on a blockchain; a multi-signature wallet mechanism configured to require multiple approvals for authorizing transactions, wherein one approval is provided by the patient to grant consent for releasing their medical records on the blockchain and another approval is provided by a trusted healthcare provider to confirm the validity of the medical data; a timestamping module configured to timestamp each transaction, ensuring that all actions are recorded with precise time information; a cryptographic security module configured to cryptographically secure each transaction, providing a transparent and auditable trail of patient consent actions; wherein said audit trail includes all actions, approvals, timestamps, and cryptographic signatures, ensuring regulatory compliance and accountability by maintaining a clear and verifiable record of patient consent. H) A method for granting view access to medical image NFTs by other parties, comprising: an access control module configured to gate access through authentication using cryptographic signing and zero-knowledge proofs (ZKPs); a user layer interface configured to authenticate users, wherein said user layer interface utilizes an application layer authentication module; an application layer configured to retrieve a list of tokens owned by the authenticated user's wallet address, wherein the application layer communicates with a wallet module to obtain the user's wallet address and utilizes a relayer module to interact with the blockchain layer; a smart contract on the blockchain layer, designed for managing NFTs, configured to query and obtain a response containing a list of NFTs minted for the user's wallet address; a presentation module within the user layer interface configured to present the retrieved list of tokens to the user; a decryption module within the application layer configured to decrypt a URI stored within the selected token using the user's private key; a retrieval module configured to retrieve metadata associated with the medical record from a decentralized storage system using the decrypted URI; an optional presentation module configured to present the retrieved metadata to the user within the user layer interface; wherein the access control module for granting view access to medical image NFTs by other parties includes: a smart contract configured to generate a cryptographic challenge for the recipient, ensuring the recipient possesses the necessary credentials for viewing the medical image; a proof generation module configured to allow the recipient to utilize their private key and the medical image NFT information to generate a Zero Knowledge Proof, wherein the proof demonstrates the recipient has the required access rights without revealing any sensitive medical information; a verification module within the smart contract configured to verify the ZKP using the public key associated with the recipient, and upon successful verification, grant temporary access to the medical image data.

I) A method for facilitating secure and auditable sharing of medical data between patients and authorized recipients, comprising: a cryptographic wallet module configured to allow patients to initiate share requests through their cryptographic wallets; a smart contract module configured to automatically and autonomously enforce access permissions; a blockchain ledger module configured to record sharing transactions for transparency and accountability; an authorization module within the cryptographic wallet module configured to enable patients to generate and sign share requests, specifying the medical data to be shared and the authorized recipients; a permissions definition module within the smart contract module configured to define access permissions, including conditions such as view-only access and time-limited access; a transaction recording module within the blockchain ledger module configured to record each sharing event, detailing the patient initiating the share, the authorized recipient, and the access permissions granted. The method involves patients utilizing their secure digital wallets to initiate requests to share their medical data, represented by digital ownership certificates (NFTs), with authorized individuals such as doctors. Upon initiation, the smart contracts on the blockchain act as pre-programmed agreements, automatically managing and enforcing the defined access permissions. Each sharing event, including the specifics of who shared with whom and under what permissions, is permanently and transparently recorded on the blockchain ledger. This approach ensures patient privacy while promoting accountability and traceability.

J) An authorization framework for validating share requests and enforcing access permissions, wherein said framework comprises: an identity verification module configured to authenticate the identities of authorized recipients using cryptographic methods; a proof of authorization module configured to require said recipients to provide evidence of their authorization to access specific medical data; a smart contract module configured to govern the execution of share transactions based on predefined rules; an access control module configured to manage and enforce access permissions defined by said smart contract module; and a blockchain ledger module configured to record all share transactions for transparency and accountability. The method comprises the steps of: Authenticating, wherein said authorized recipients such as doctors or researchers authenticate their identity through secure cryptographic methods. Providing proof of authorization, wherein said recipients demonstrate they have the necessary permissions to access specific medical data being shared, said permissions being granted directly by the patient or predefined within the system, such as a doctor's license tied to a specific hospital. Controlling access, wherein said smart contracts serve as pre-programmed agreements on the blockchain, controlling access to medical data by enforcing rules such as view-only access for a specified duration. Enforcing verification, wherein said system ensures that access is granted only when all verification steps are complete, thereby maintaining a high level of security and control over shared medical data. Recording transactions, wherein each transaction is recorded on the blockchain ledger, providing a transparent and immutable record of access requests and permissions granted. Wherein said identity verification module is configured to authenticate the identities of recipients using cryptographic methods to ensure they are who they claim to be. Wherein said proof of authorization module is configured to require recipients to provide evidence of their authorization to access specific medical data, such as a license or patient consent. Wherein said access control module is configured to manage and enforce the access permissions defined by said smart contract, ensuring that only authorized recipients can access the data under the specified conditions. Wherein said blockchain ledger module is configured to record all share transactions on the blockchain, ensuring transparency, immutability, and accountability.

K) A method for securely revoking access to medical data on a distributed ledger, comprising: A patient user interface configured to interface with a patient; An application layer configured to collect data from said patient user interface and maintain a patient user account associated with the patient, said patient user account including a patient user name, patient user password, and patient user email address, and said patient user account associated with a cryptographic wallet address; Said application layer having a trusted patient registration module configured to determine if a patient user account is authorized to revoke access permissions on the distributed ledger based on biometric authentication and validation of the patient user email address; A cryptographic wallet module configured to: Instantiate an authorized patient hierarchical-deterministic cryptographic wallet for said patient user account in response to said trusted patient registration module determining that said patient user account is authorized, wherein said authorized patient hierarchical-deterministic cryptographic wallet is associated with said authorized patient user account based on said patient email address, Wherein said patient hierarchical-deterministic cryptographic wallet includes an authorized patient wallet address, an authorized patient public key, and an authorized patient private key for said authorized patient user account, Wherein said authorized patient hierarchical-deterministic cryptographic wallet is generated from a master key retrieved from a secure vault that automatically and mathematically generates an infinite number of child keys including the authorized patient public key and the authorized patient private key of the patient hierarchical-deterministic cryptographic wallet; A revocation mechanism module configured to: Enable said authorized patient to initiate a revocation process to revoke previously granted access permissions to medical data by updating a state of a smart contract associated with the medical data on the distributed ledger, Wherein said revocation process utilizes cryptographic authentication and verification processes to ensure integrity and confidentiality of the revocation request using the authorized patient private key, Wherein an immutable audit trail of the revocation event is recorded on the distributed ledger, said audit trail comprising a timestamp and identification of the authorized patient initiating the revocation.

L) A system for securely requesting medical imaging data, comprising: A healthcare provider user interface configured to interface with a healthcare provider; An application layer configured to collect data from said healthcare provider user interface and maintain a healthcare provider user account associated with the healthcare provider, said healthcare provider user account including a healthcare provider user name, healthcare provider user password, and healthcare provider user email address, and said healthcare provider user account associated with a cryptographic wallet address; Said application layer having a trusted issuer registration module configured to determine if a healthcare provider user account is authorized to submit requests for medical imaging data on a distributed ledger based on verification of healthcare provider credentials and validation of the healthcare provider user email address; A request mechanism module configured to: Enable said authorized healthcare provider to submit a request for medical imaging data from other healthcare institutions not enrolled in the system, by providing relevant patient details including patient name, date of birth, and other personal identifiers, along with appropriate authorization credentials, Wherein said authorization credentials comprise at least one of: patient consent allowing the authorized healthcare provider access to the requested medical imaging data, and an institutional agreement between the healthcare institution of the authorized healthcare provider and the healthcare institution hosting the requested medical imaging data; Wherein said request for medical imaging data utilizes cryptographic processes to ensure integrity and confidentiality of the request; Wherein an immutable audit trail of the request event is recorded on the distributed ledger, said audit trail comprising the patient details, authorization credentials utilized, a timestamp, and identification of the authorized healthcare provider submitting the request.

M) A method for automating patient consent for sharing medical imaging data using non-fungible tokens (NFTs) on a distributed ledger, comprising: Representing medical imaging data as NFTs on the distributed ledger; A patient user interface configured to interface with a patient; An application layer configured to collect data from said patient user interface and maintain a patient user account associated with the patient, said patient user account including a patient user name, patient user password, and patient user email address, and said patient user account associated with a cryptographic wallet address; A consent mechanism module configured to: Enable said patient to provide consent for sharing the medical imaging data represented by an associated NFT through a digital signature of a consent form interaction, wherein said interaction comprises at least one of: approving a request to share the medical imaging data, and digitally signing a consent linked to a smart contract controlling the associated NFT; Wherein said consent provided by the patient is recorded as an immutable transaction on the distributed ledger, said transaction comprising at least one of: details of the consent granted, identification of the medical imaging data and associated NFT, a timestamp, and identification of the patient providing consent; Wherein the immutable transaction representing the patient's consent is cryptographically verifiable on the distributed ledger to ensure integrity and non-repudiation of the consent.

M) A method for enabling gasless transactions on a distributed ledger, comprising: A user interface configured to interface with a user; An application layer configured to collect data from said user interface and maintain a user account associated with the user; A relayer module comprising a relayer cryptographic wallet, said relayer cryptographic wallet funded with cryptocurrency for paying transaction fees on the distributed ledger; A gasless transaction mechanism configured to: Receive an instruction from the user account to perform an action on the distributed ledger; Generate a transaction request based on the received instruction; Transmit the transaction request to the relayer module; Wherein the relayer module is configured to: Receive the transaction request from the gasless transaction mechanism; Pay the transaction fee required for the transaction request using cryptocurrency from the relayer cryptographic wallet; Broadcast the transaction request to nodes on the distributed ledger for execution; Wherein the user is enabled to perform the action on the distributed ledger without directly paying the transaction fee, said transaction fee being paid by the relayer module on behalf of the user, thereby abstracting the concept of the distributed ledger from the user experience.

O) A custom, integrated blockchain explorer tool for a medical imaging data exchange system on a distributed ledger, comprising: A user interface configured to interface with a user; An explorer module configured to: Retrieve and display transactions recorded on the distributed ledger in real-time as they occur; Provide search functionality for the user to query specific transactions based on transaction hashes, cryptographic wallet addresses, or data contained within the transactions; Display detailed information about queried transactions, including block details, timestamps, and relevant metadata; Visualize a mempool of pending transactions waiting to be included in a block on the distributed ledger; Wherein the explorer module enables the user to view and analyze transactions on the distributed ledger related to the medical imaging data exchange system, providing transparency into the real-time state and activity of the system's data recorded on the distributed ledger; Wherein the user interface presents the retrieved and analyzed transaction data from the explorer module in a user-friendly format, allowing the user to monitor, search, and gain insights into the medical imaging data transactions occurring on the distributed ledger.

P) A method for auditing and monitoring the activities of authorized healthcare providers within a medical imaging data exchange system on a distributed ledger, comprising: An audit module configured to: Monitor and record transactions on the distributed ledger associated with authorized healthcare provider accounts; Monitor and record events emitted by smart contracts on the distributed ledger in response to interactions by authorized healthcare providers; Wherein the recorded transactions and smart contract events capture actions performed by authorized healthcare providers, including but not limited to: Requesting medical imaging data from other healthcare institutions; Accessing and viewing medical imaging data; Sharing or transmitting medical imaging data; Wherein the audit module analyzes the recorded transactions and events to ensure compliance of the authorized healthcare providers with applicable regulations, standards, and data sharing protocols; Wherein the recorded transactions and events provide an immutable audit trail on the distributed ledger, enabling verification of the authorized healthcare providers' activities and facilitating oversight within the medical imaging data exchange system.

Q) An authentication mechanism for verifying credentials and accreditation of healthcare providers before granting access to a medical imaging data exchange system, comprising: An authentication module configured to: Implement multi-factor authentication for healthcare providers attempting to access the system, wherein authentication factors include at least one of: a username and password, a one-time passcode sent to a registered device, biometric authentication; Verify healthcare provider credentials by cross-checking provided information against authoritative sources, including but not limited to: Querying professional licensing boards to confirm the healthcare provider's accreditation and credentials are valid and up-to-date; Utilizing a decentralized identity management system on a distributed ledger to cryptographically verify the healthcare provider's identity and credentials; Wherein the authentication module only grants the healthcare provider access to the medical imaging data exchange system if both the multi-factor authentication and credential verification steps are successfully completed; Wherein the decentralized identity management system enables healthcare providers to securely manage and control their professional credentials on the distributed ledger, facilitating secure verification while preventing unauthorized modification of credentials.

R) A method for tracking and auditing shared medical imaging data transactions on a distributed ledger, comprising: A transaction monitoring module configured to: Record transactions on the distributed ledger representing events related to sharing of medical imaging data, wherein recorded transactions include: Share request transactions, comprising details of a patient requesting to share medical imaging data and identification of intended recipients; Share approval transactions, comprising details of a patient approving or denying a share request for their medical imaging data; Access transactions, comprising details of an approved recipient accessing or downloading shared medical imaging data, including timestamps and extent of data accessed; Revocation transactions, comprising details of a patient revoking previously granted access to their medical imaging data from a recipient; Patient request transactions, comprising details of a patient requesting access to their own medical imaging data from a healthcare institution; Request processing transactions, comprising details of a healthcare institution processing, approving, or denying a patient's request for their medical imaging data; Wherein each recorded transaction is immutable and cryptographically verifiable on the distributed ledger, providing transparency into the usage, sharing, and dissemination of the medical imaging data; Wherein the transaction monitoring module enables patients to view an auditable history of all recorded transactions related to their medical imaging data, facilitating visibility and control over how their healthcare information is accessed and shared within the system.

S) The medical imaging data exchange system comprises a modular framework designed with flexibility to integrate with externally managed cryptographic wallet modules, wherein: The cryptographic wallet module is configured to interface with external cryptographic wallet providers and services; Enabling users to utilize cryptographic wallets managed by third-party providers instead of the system's built-in cryptographic wallet module; Wherein the system supports a plurality of external cryptographic wallet integration methods, including but not limited to: Importing user's existing external wallet credentials and keys into the system; Establishing secure connections with external wallet APIs to interact with and manage the user's external wallet; Implementing industry-standard cryptographic protocols and interfaces to ensure interoperability with a wide range of external wallet solutions; Wherein the modular design allows the system to adapt to changing wallet technologies and user preferences, providing flexibility for users to select their preferred wallet management approach while maintaining secure integration with the medical imaging data exchange platform.

The system and method of the present system (5) include operation by one or more processing devices, as represented by the architecture diagram of FIG. 1, and the system diagram of FIG. 15 (including, for example, the user computers, server (182), and the blockchain network (280). It is noted that the processing device can be any suitable device, such as a computer, server, mainframe, processor, microprocessor, PC, tablet, smartphone, or the like. The processing devices can be used in combination with other suitable components, such as a display device (monitor, LED screen, digital screen, etc.), memory or storage device, input device (touchscreen, keyboard, pointing device such as a mouse), wireless module (for RF, Bluetooth, infrared, WiFi, etc.). The information may be stored on a computer hard drive, on a CD ROM disk or on any other appropriate data storage device, which can be located at or in communication with the processing device. The entire process is conducted automatically by the processing device, and without any manual interaction. Accordingly, unless indicated otherwise the process can occur substantially in real-time without any delays or manual action.

The foregoing description and drawings should be considered as illustrative only of the principles of the disclosure. The system may be configured in a variety of ways and is not intended to be limited by the disclosure. Numerous applications of the system will readily occur to those skilled in the art. Therefore, it is not desired to limit the system to the specific examples disclosed or the exact construction and operation shown and described. Rather, all suitable modifications and equivalents may be resorted to, falling within the scope of the disclosure.

The invention claimed is:

1. A medical data management system, comprising:
a storage device configured to store encrypted patient medical data associated with a patient user account and a patient email address;
an application layer having a hierarchical-deterministic cryptographic wallet module, and a trusted issuer registration module;
said hierarchical-deterministic cryptographic wallet module configured to:
  generate an infinite number of child key pairs having public keys and private keys in a hierarchical fashion, wherein said child key pairs are derived from a master key, the master key randomly generated from a seed phrase stored in a highly secured vault with identity-based security to automatically authenticate and authorize access to the seed phrase;
  generate a patient cryptographic wallet for the patient user account with the patient email address, and associating the patient cryptographic wallet with the patient user account in said storage device;
said trusted issuer registration module configured to:
  collect healthcare provider data from a healthcare provider user interface;
  maintain a healthcare provider user account associated with the healthcare provider data, said healthcare provider user account includes a healthcare provider username, a healthcare provider credential, and a healthcare provider user email address;
  verify said healthcare provider user email address with authoritative sources including receiving a user verification input or comparing said healthcare provider credential, and said healthcare provider user email address with a a verified healthcare provider credential, and a verified healthcare provider user email address received from a verification source, to provide a verified healthcare provider user account;
  create a verified hierarchical-deterministic healthcare provider cryptographic wallet associated with said healthcare provider user email address for said verified healthcare provider user account, in response to said verified healthcare provider user account, wherein said verified hierarchical-deterministic healthcare provider cryptographic wallet includes a verified healthcare provider wallet address, a verified healthcare provider public key and a verified healthcare provider private key based on said generated child key pairs from said hierarchical-deterministic cryptographic wallet module; and a blockchain layer comprising a self-executing smart contract module on a blockchain, said smart contract module configured to:
maintain a whitelist of verified healthcare provider wallet addresses;
add said verified healthcare provider user wallet address associated with a verified healthcare provider user account from said trusted issuer registration module to said whitelist, in response to said trusted issuer registration module;
receive a healthcare blockchain provider request to exchange said patient medical data from a healthcare provider cryptographic wallet, said healthcare provider blockchain request including a requested patient email address, said smart contract module only allowing patient medical data to be exchanged with the received healthcare provider cryptographic wallet that is associated with a verified healthcare provider user account on the whitelist and if the requested patient email address is associated with said patient cryptographic wallet, whereby only whitelisted verified healthcare provider wallet address associated with verified healthcare provider wallet addresses can exchange patient medical data with said storage device; and
receive a patient blockchain request to access the patient medical data from a requesting patient email address and only allowing the patient medical data to be accessed if the requesting patient email address matches a patient wallet address associated with the received patient email address.

2. The system of claim 1, wherein the blockchain layer comprises a distributed public, private or permissioned blockchain ledger.

3. The system of claim 1, wherein said creation of said wallet comprises an external cryptographic wallet integration technique, including but not limited to:
importing healthcare provider or patient user's existing external wallet credentials and keys into the system;
establishing secure connections with external wallet APIs to interact with and manage the healthcare provider user's external wallet; and
implementing industry-standard cryptographic protocols and interfaces to ensure interoperability with a wide range of external wallet solutions, adapt to changing wallet technologies and user preferences, providing flexibility for users to select their preferred wallet management approach while maintaining secure integration with the medical imaging data exchange platform.

4. The system of claim 1, wherein said the patient medical data comprises a patient medical imaging study and the patient user account is the owner of the patient medical imaging study, and wherein the patient medical imaging study contains PHI and patient medical images.

5. The system of claim 1, further comprising an authentication module configured to implement multi-factor authentication for healthcare provider users and patient users attempting to access the system, wherein authentication factors include at least one of: a username and password, a one-time passcode sent to a registered device or registered application like email or application that will enhance security and/or enable passwordless authentication.

6. The system of claim 1, further comprising post-processing and extraction of the patient medical imaging studies into medical images and metadata upon detection of patient medical imaging study files in a designated local location (such as a Picture Archiving and Communication Systems) or upon upload into a the system after verification that the origination of the patient medical image is from a trusted issuer patient user account.

7. The system of claim 6, wherein said metadata includes patient information, date, type of scan, along with a URI that serves a secure pointer that references the location of the encrypted to the encrypted medical image data on the cloud and other relevant details; an upload module configured to autonomously upload the encrypted metadata to a distributed storage network, such as IPFS, wherein said distributed storage network provides enhanced security and redundancy by storing data across multiple locations.

8. The system of claim 1, wherein said storage device is configured to securely store the patient medical data and associated patient details in a secure cloud storage system after encrypting with patient's public key; and the cloud storage system includes redundancy and backup mechanisms to ensure that the encrypted medical images and metadata are preserved and can be recovered in case of data loss or corruption.

9. The system of claim 7, further comprising a verification module configured to validate the integrity and authenticity of the encrypted metadata and the encrypted URI reference, ensuring that only authorized access to the encrypted metadata is permitted; verification process ensures data integrity such that the uploaded medical images and metadata maintain their integrity and are not altered during the encryption and upload process.

10. The system of claim 1, further comprising:
a multi-signature wallet mechanism configured to require multiple approvals for authorizing transactions, wherein one approval is provided by the patient user to grant patient consent for releasing their medical records on the blockchain and another approval is provided by a trusted healthcare provider user to confirm the validity of the medical data;
automating patient consent using digital signatures, wherein the patient provides consent for sharing patient medical imaging data represented by an associated non-fungible token (NFT) through a digital signature of a consent form interaction, wherein said interaction comprises at least one of: approving a request to share the medical imaging data, and digitally signing a consent linked to a smart contract controlling the distribution of the associated NFT; and
wherein said patient consent provided by the patient is recorded as an immutable transaction on the distributed ledger, said transaction comprising at least one of: details of the consent granted, identification of the medical imaging data and associated NFT, a timestamp, and identification of the patient providing consent.

11. The system of claim 1, further comprising:
a digital record comprising a non-fungible token (NFT);
a minting module configured to mint NFTs upon successful verification by the smart contract module of the trusted issuer authorized cryptographic wallet address, wherein each NFT represents a specific medical image study and includes the patient as the owner of the NFT; and
wherein the NFTs contain the encrypted references generated by the metadata encryption module, said encrypted references acting as secure pointers to the metadata stored in the decentralized storage device.

12. The system of claim 1, further comprising modules for authentication and access control of patient medical imaging data, said modules comprising:

an authentication mechanism configured to validate patient user identities and verify their ownership of patient medical data before granting access to view released patient medical imaging data;

an identity verification module designed to securely verify and authenticate a patient's identity using secure methods, including multi-factor authentication (MFA) or other secure methods, ensuring accurate identification before any actions related to viewing, sharing, or revoking access to the data; and an access control module configured to restrict access to only authorized users who can access and decrypt the metadata referenced by non-fungible tokens (NFTs), thereby maintaining the security and integrity of the medical image studies and their associated metadata.

13. The system of claim 1, wherein said access control module for granting viewing access to medical image non-fungible tokens (NFTs) by other parties comprises:

said smart contract configured to generate a cryptographic challenge for a recipient, ensuring the recipient possesses the necessary credentials for viewing the medical image NFT;

granting view access to medical image NFTs, comprising:
the access control module configured to gate access through authentication using cryptographic signing and zero-knowledge proofs (ZKPs);

a proof generation module configured to allow the recipient to utilize their private key and the medical image NFT information to generate a zero-knowledge proof (ZKP);

wherein said ZKP demonstrates the recipient has the required access rights without revealing any sensitive medical information; and a verification module within the smart contract configured to verify the ZKP using the public key associated with the recipient, and upon successful verification, grant temporary access to the medical image data referenced by the NFT.

14. The system of claim 1, further comprising:

said application layer configured to retrieve a list of tokens owned by the authenticated user's wallet address, wherein the application layer communicates with a wallet module to obtain the user's wallet address; and a token querying module configured to:
utilize a token API service to query and retrieve token balances for the user's wallet address by calling the service's API endpoint and passing the wallet address as a parameter;

query individual token contract addresses by calling the balance of function for each token contract and passing the user's wallet address, and aggregating the results;

parse the transaction history of the user's wallet address obtained from a blockchain explorer API to determine token balances;

utilize a blockchain indexing service's API to query and retrieve the list of tokens owned by the user's wallet address;

wherein the token querying module returns the list of tokens owned by the authenticated user's wallet address to the application layer for further processing or display.

15. A system as in claim 1, further comprising:

a presentation module within the user interface layer;

a retrieval module configured to retrieve metadata associated with the medical record from a decentralized storage device using the decrypted URI;

a decryption module within the application layer configured to decrypt a Uniform Resource Identifier (URI) and other metadata information stored within a selected token using the user's private key;

wherein the presentation module is configured to present the retrieved list of tokens to the user in a user-friendly interface, aggregating the user's medical records from any healthcare provider into a centralized view.

16. The system as claim 1, wherein said system facilitates secure and auditable sharing of patient medical data between patients and authorized recipients, comprising:

said cryptographic wallet module allowing patients to initiate share requests through their cryptographic wallets;

an authorization module within the cryptographic wallet module, empowering patients to generate and sign share requests, specifying the medical data to be shared and the authorized recipients, said authorization module ensures an immutable audit trail of the revocation event is recorded on the distributed ledger, comprising a timestamp and identification of the authorized patient initiating the sharing, the destination address of the revoked address, and other relevant details.

17. The system of claim 1, wherein said smart contract module governs the execution of share transactions based on predefined rules, the rules include verifying if the initiating wallet is the owner of the NFT representing the medical study, ensuring secure and controlled access to patient medical data, wherein said smart contract module further comprises an access control module managing and enforcing access permissions defined by the smart contract module.

18. The system of claim 1, further comprising a revocation mechanism module configured to:

enable said an authorized patient to initiate a revocation process to revoke previously granted access permissions to medical data by updating a state of a smart contract associated with the medical data on the distributed ledger, wherein said revocation process utilizes cryptographic authentication and verification processes to ensure integrity and confidentiality of the revocation request using the authorized patient private key, wherein an immutable audit trail of the revocation event is recorded on the distributed ledger, said audit trail comprising a timestamp and identification of the authorized patient initiating the revocation, the address of the revoked user, and other relevant details.

19. The system in claim 1, further comprising:

a secure and auditable request mechanism integrated into the medical data management system, wherein said request mechanism enables trusted issuers to submit requests for medical images from other healthcare institutions irrespective of their enrollment in the system, said requests comprising relevant patient details including at least one of: name, date of birth, and other personal identifiers, along with appropriate authorization credentials;

a request encoding module configured to generate a QR code representing the request and its subsequent status;

wherein the request can be transmitted via at least one of: email, text message, or other secured means.

20. The system of claim 1, further comprising an audit trail recording module configured to record an immutable audit trail of the request event on the distributed ledger, said audit trail comprising at least one of: the patient details, authorization credentials utilized, a timestamp, and identification of the authorized healthcare provider submitting the request.

21. The system of claim 1, said system enabling gasless transactions on a distributed ledger, and further comprising: a relayer module comprising having a relayer cryptographic wallet, said relayer cryptographic wallet funded with cryptocurrency for paying transaction fees on the distributed ledger.

22. The system of claim 1, gasless transaction mechanism configured to, the system configured to:
   receive an instruction from the user account to perform an action on the distributed ledger;
   generate a transaction request based on the received instruction;
   transmit the transaction request to the relayer module;
   wherein said relayer module is configured to:
   receive the transaction request from the gasless transaction mechanism;
   pay the transaction fee required for the transaction request using cryptocurrency from the relayer cryptographic wallet;
   wherein the user is enabled to perform the action on the distributed ledger without directly paying the transaction fee, said transaction fee being paid by the relayer module on behalf of the user, thereby abstracting the concept of the distributed ledger from the user experience.

23. The system of claim 1, further comprising a custom, fully anonymized, integrated blockchain explorer module is configured for a medical imaging data exchange system on a distributed ledger,
   wherein said explorer module is configured to:
   retrieve and display transactions recorded on the distributed ledger in real-time as they occur;
   provide search functionality for the user to query specific transactions based on transaction hashes, cryptographic wallet addresses, or data contained within the transactions;
   display detailed information about queried transactions, including block details, timestamps, and relevant metadata;
   visualize a mempool of pending transactions waiting to be included in a block on the distributed ledger;
   wherein said explorer module comprises a user interface that enables the user to view and analyze transactions on the distributed ledger related to the medical imaging data exchange system, providing transparency into the real-time state and activity of the system's data recorded on the distributed ledger;
   wherein said user interface presents the retrieved and analyzed transaction data from the explorer module in a user-friendly format, allowing the user to monitor, search, and gain insights into the medical imaging data transactions occurring on the distributed ledger.

24. A system of claim 1 for transaction monitoring in medical imaging data sharing, comprising:
   a transaction monitoring module configured to connect to a distributed ledger network and analyze transactions representing events related to medical imaging data sharing;
   a secure and immutable storage system for logging validated transactions and metadata;
   an analytics engine for analyzing transaction data and generating alerts and notifications based on detected anomalies;
   a compliance reporting module for producing compliance reports summarizing transaction activities; and
   a feedback mechanism for iteratively refining monitoring capabilities based on stakeholder feedback and evolving requirements.

25. The system of claim 1, wherein this application, application interfaces, and the application architecture is not limited to healthcare imaging but can be extended to any modality of images, any types of medical records, and any industry both for secure and optimized data transmission but also for storage.

26. The system of claim 1, wherein said blockchain comprises said smart contract module, said patient cryptographic wallet, said verified hierarchical-deterministic healthcare provider cryptographic wallet, said whitelist, and said NFTs representing the imaging studies.

27. A medical data management system, comprising:
   a storage device configured to store encrypted patient medical data associated with a patient user account and a patient email address;
   an application layer having a hierarchical-deterministic cryptographic wallet module, and a trusted issuer registration module;
   said hierarchical-deterministic cryptographic wallet module configured to:
   generate an infinite number of child key pairs having public keys and private keys in a hierarchical fashion, wherein said child key pairs are derived from a master key, the master key randomly generated from a seed phrase stored in a highly secured vault with identity-based security to automatically authenticate and authorize access to the seed phrase;
   generate a patient cryptographic wallet for the patient user account with the patient email address, and associating the patient cryptographic wallet with the patient user account in said storage device;
   a blockchain layer comprising a smart contract module on a blockchain, said smart contract module configured to:
   receive a patient request to access the patient medical data from a requesting patient email address and only allowing the patient medical data to be exchanged if the requesting patient email address matches a patient wallet address associated with the received patient email.

28. A medical data management system, comprising:
   a storage device configured to store encrypted patient medical data associated with a patient user account and a patient email address;
   an application layer having a hierarchical-deterministic cryptographic wallet module, and a trusted issuer registration module;
   said hierarchical-deterministic cryptographic wallet module configured to:
   generate an infinite number of child key pairs having public keys and private keys in a hierarchical fashion, wherein said child key pairs are derived from a master key, the master key randomly generated from a seed phrase stored in a highly secured vault with identity-based security to automatically authenticate and authorize access to the seed phrase;
   generate a patient cryptographic wallet for the patient user account with the patient email address, and associating the patient cryptographic wallet with the patient user account in said storage device;
   said trusted issuer registration module configured to:
   collect healthcare provider data from a healthcare provider user interface;

maintain a healthcare provider user account associated with the healthcare provider data, said healthcare provider user account includes a healthcare provider username, a healthcare provider credential, and a healthcare provider user email address;

verify said healthcare provider username and said healthcare provider user email address with authoritative sources including receiving a user verification input or comparing said healthcare provider username, said healthcare provider credential, and said healthcare provider user email address with a verified healthcare provider username, a verified healthcare provider credential, and a verified healthcare provider user email address received from a verification source, to provide a verified healthcare provider user account;

create an verified hierarchical-deterministic healthcare provider cryptographic wallet associated with said healthcare provider user email address for said verified healthcare provider user account, in response to said verified healthcare provider user account, wherein said verified hierarchical-deterministic healthcare provider cryptographic wallet includes a verified healthcare provider wallet address, a verified healthcare provider public key and a verified healthcare provider private key based on said generated child key pairs from said hierarchical-deterministic cryptographic wallet module; and a blockchain layer comprising a smart contract module on a blockchain, said smart contract module configured to:

maintain a whitelist of verified healthcare provider wallet addresses;

add said verified healthcare provider user account from said trusted issuer registration module to said whitelist, in response to said trusted issuer registration module;

receive a healthcare provider request to exchange said patient medical data from a healthcare provider cryptographic wallet and only allowing patient medical data to be exchanged with the received healthcare provider cryptographic wallet that is associated with a verified healthcare provider user account on the whitelist, whereby only whitelisted verified healthcare provider wallet address associated with verified healthcare provider wallet addresses can exchange patient medical data with said storage device.

* * * * *